(12) United States Patent
He et al.

(10) Patent No.: US 12,173,045 B2
(45) Date of Patent: Dec. 24, 2024

(54) HUMAN ALPHA FETOPROTEIN-SPECIFIC T CELL RECEPTORS AND USES THEREOF

(71) Applicant: Augusta University Research Institute, Inc., Augusta, GA (US)

(72) Inventors: Yukai He, Martinez, GA (US); Wei Zhu, Augusta, GA (US); Esteban Celis, Augusta, GA (US); Yibing Peng, Augusta, GA (US); Lan Wang, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 552 days.

(21) Appl. No.: 17/353,409

(22) Filed: Jun. 21, 2021

(65) Prior Publication Data

US 2022/0048971 A1    Feb. 17, 2022

Related U.S. Application Data

(62) Division of application No. 15/969,211, filed on May 2, 2018, now Pat. No. 11,041,011.

(60) Provisional application No. 62/625,051, filed on Feb. 1, 2018, provisional application No. 62/609,614, filed on Dec. 22, 2017, provisional application No. 62/505,406, filed on May 12, 2017.

(51) Int. Cl.
| | | |
|---|---|---|
| C07K 14/725 | (2006.01) | |
| A61K 35/17 | (2015.01) | |
| A61P 35/00 | (2006.01) | |
| A61K 38/00 | (2006.01) | |
| C07K 16/46 | (2006.01) | |

(52) U.S. Cl.
CPC .......... *C07K 14/7051* (2013.01); *A61K 35/17* (2013.01); *A61P 35/00* (2018.01); *A61K 38/00* (2013.01); *C07K 16/462* (2013.01)

(58) Field of Classification Search
None
See application file for complete search history.

(56) References Cited

U.S. PATENT DOCUMENTS

| | | |
|---|---|---|
| 5,005,079 A | 4/1991 | Satomi |
| 5,013,556 A | 5/1991 | Woodle et al. |
| 5,859,205 A | 1/1999 | Adair et al. |
| 5,861,155 A | 1/1999 | Lin |
| 6,005,079 A | 12/1999 | Casterman et al. |
| 2008/0219956 A1 | 9/2008 | Russell et al. |
| 2010/0104556 A1 | 4/2010 | Blankenstein et al. |
| 2013/0011375 A1 | 1/2013 | Chen |
| 2013/0273647 A1 | 10/2013 | Sahin et al. |
| 2016/0137715 A1 | 5/2016 | Molloy |
| 2016/0219844 A1 | 8/2016 | Brown et al. |
| 2018/0327473 A1 | 11/2018 | He et al. |
| 2019/0330301 A1 | 10/2019 | Molloy et al. |

FOREIGN PATENT DOCUMENTS

| | | |
|---|---|---|
| CN | 104087592 A | 10/2014 |
| CN | 105255834 A | 1/2016 |
| CN | 105408353 A | 3/2016 |
| CN | 105802909 A | 7/2016 |
| CN | 110662760 A | 1/2020 |
| EP | 0460167 A1 | 12/1991 |
| EP | 3622074 A1 | 3/2020 |
| HK | 40011939 A | 7/2020 |
| ID | 2020/PID/00754 | 2/2020 |
| JP | 2016-525537 A | 8/2016 |
| JP | 2020-519293 A | 7/2020 |
| KR | 10-2016-0034329 A | 3/2016 |
| KR | 10-2020-0006985 A | 1/2020 |
| WO | 91/09967 A1 | 7/1991 |
| WO | 2007/131092 A2 | 11/2007 |
| WO | 2015/011450 A1 | 1/2015 |
| WO | 2016/085904 A1 | 6/2016 |
| WO | 2018/208553 A1 | 11/2018 |

OTHER PUBLICATIONS

Notice of Reasons for Rejection received for Japanese Patent Application No. 2019-562424, mailed on Mar. 3, 2022, 6 pages (3 pages of English Translation and 3 pages of Original Document).
Office Action received for Chinese Patent Application No. 201880030341, mailed on Jul. 11, 2023, 17 pages (9 pages of English Translation and 8 pages of Original Document).
Adams, E.J., et al., "An autonomous CDR3d is sufficient for recognition of the nonclassical MHC class I molecules T10 and T22 by ?d T cells", Nat Immunol., 9(7): 777-784 (2008).
Butterfield, L.H., et al., "A phase I/II trial testing immunization of heptocellular carcinoma patients with dendritic Cells pulsed with four alpha-fetoprotein peptides", Clin Cancer Res, 12:2817-2825 (2006).
Butterfield, L.H., et al., "T cell responses to HLA-*0201 immunodominant peptides derived from alpha-fetoprotein in patients with hepatocellular cancer", Clin Cancer Res, 9:5902-5908 (2003).
Butterfield, L.H., et al., "T cell responses to HLA-A*0201-restricted peptides derived from human alpha fetoprotein", J Immunol, 166:5300-5308 (2001).
Cameron, B.J., et al., "Identification of a Titin-derived HLA-A1-presented peptide as a cross-reactive target for engineered MAGE A3-directed T cells", Sci Transl Med, 5:197ra03 (2013).
Cho, H.I., et al., "Optimized peptide vaccines eliciting extensive CD8 T-cell responses with therapeutic antitumor effects", J Immunol, 182:5960-5969 (2009).
Chothia, Cyrus et al, "Canonical Structures for the Hypervariable Regions of Immunoglobulins", J. Mol. Biol. 196, 901-917 (1987).
Cohen, C.J., et al., "Enhanced antitumor activity of murine-human hybridoma T-cell receptor (TCR) in human lymphocytes is associated with improved pairing and TCR/CD3 stability", 66:8878-8886 (2006).
Communication pursuant to Rules 70(2) and 70a(2) in corresponding European application EP18799369.6, mailed on Jan. 14, 2021, 1 page.

(Continued)

*Primary Examiner* — Zachary S Skelding
(74) *Attorney, Agent, or Firm* — Judy Jarecki-Black; Sharon Ngwenya

(57) ABSTRACT

T cell receptors that specifically recognize hAFP$_{158}$ and methods of their use are provided.

5 Claims, 29 Drawing Sheets

Specification includes a Sequence Listing.

(56) References Cited

OTHER PUBLICATIONS

PCT International Search Report/Written Opinion released in the corresponding PCT application, PCT/US18/30637, on Sep. 20, 2018, 16 pages.

Dargel, C., et al., "T cells engineered to express a T-cell receptor specific for glypican-3 to recognize and kill hepatoma cells in vitro and in mice", Gastroenterology, 149:1042-1052 (2015).

Davis, J.L., et al., "Development of human anti-murine T-cell receptor antibodies in both responding and honresponding patients enrolled in TCR gene therapy trials", Clin Cancer Res, 16:5852-5861 (2010).

El-Serag HB, et al., "Diabetes increases the risk of chronic liver disease and hepatocellular carcinoma", Gastroenterology, 126:460-468 (2004).

European Search Report and Search Opinion Received for EP Application No. 18799369, mailed on Dec. 11, 2020, 8 pages.

Faden, R.R., et al., "Public Stem Cell Banks: Considerations of Justice in Stem Cell Research and Therapy", Hastings Cent Rep., 33(6): 13-27 (2003).

Ferlay, J., et al., "Estimates of worldwide burden of cancer in 2008:GLOBOCAN", Int J Cancer, 127:2893-2917 (2008).

Final Office Action received for U.S. Appl. No. 15/969,211, mailed on Oct. 6, 2020, 7 pages.

Garcia, K.C., et al., "How the T Cell Receptor Sees Antigen—A Structural View", Cell, 122: 333-336, (2005).

Goyarts, E.C., et al., "Point mutations in the beta chain CDR3 can alter the T cell receptor recognition pattern on an MHC class I/peptide complex over a broad interface area", Mol Immunol, 35(10): 593-607 (1998).

He, Yukai, et al., "Immunication with Lentiviral Vector-transduced Dendritic Cells Induces Strong and Long-Lasting T Cell responses and Therapeutic Immunity", J Immunol 174:3808-3817 (2005).

Hong, Y., et al., "Epitope-optimized alpha-fetoprotein genetic vaccines prevent carcinogen-induced murine autochthonous hepatocellular carcinoma", Hepatology, 59:1448-1458 (2014).

International Preliminary Report on Patentability received for PCT Patent Application No. PCT/US18/030637, mailed on Nov. 21, 2019, 11 pages.

International Search Report and Written Opinion received for PCT Patent Application No. PCT/US18/030637, mailed on Sep. 20, 2018, 15 pages.

Invitation to Respond to Search Report & Written Opinion in corresponding SG Application 11201909751T, received on Sep. 1, 2020, 10 pages.

Johnson, L.A., et al., "Gene therapy with human and mouse T-cell receptors mediates cancer regression and target normal tissues expressing cognate antigen", Blood, 114:535-546 (2009).

Kao, W.Y., et al., "A comparison of prognosis between patients with hepatitis B and C virus-related hepatocellular carcinoma undergoing resection surgery", World J Surg, 35:858-867 (2011).

Kim, J.H., et al., "High cleavage efficiency of a 2A peptide derived from porcine teschovirus-1 in human cell lines, zebrafish and mice", PLoS One, 6:e18556 (2011).

Klebanoff, et al., "Prospects for gene-engineered T cell immunotherapy for solid cancers", Nat Med, 22:26-36 (2016).

Kudo, M., "Immune checkpoint blockade in hepatocellular carcinoma", Liver Cancer, 4:201-207 (2015).

Kunert, A., et al., TCR-engineered T cells meet new challenges to treat solid tumors: choice of antigen, T cell fitness, and sensitization of tumor milieu, Front Immunol, 4:363 (2013).

Linette, G.P., et al., "Cardiovascular toxicity and titin cross-reactivity of affinity-enhanced T cells in myeloma and melanoma", Blood, 122:863-871 (2013).

Liu, Y., et al., "Lentivector immunization stimulates potent CD8 T cell responses against melanoma self-antigen tyrosinase-related protein 1 and generates antitumor immunity in mice", J Immunol, 182:5960-5969 (2009).

Manning, T.C., et al., "Alanine Scanning Mutagenesis of an aß T Cell Receptor: Mapping the Energy of Antigen Recognition", Immunity, 8(4): 413-425(1998).

Mathiowitz, E., et al., "Novel Microcapsules for Delivery Systems", Reactive Polymers, 6:275-283 (1987).

Mathiowitz, E., et al., "Polyanhydride Microspheres as Drug Carriers I. Hot-Melt Microencapsulation", Journal of Controlled Release, 5:13-22 (1987).

Mathiowitz, E., et al., "Polyanhydride Microspheres as Drug Carriers II. Microencapsulation by Solvent Removal", Journal of Applied Polymer Science, 35:755-774 (1988).

Morgan, R.A., et al., "Cancer regression and neurological toxicity following anti-MAGE-A3 TCR gene therapy", J Immunother, 36:133-151 (2013).

Morgan, R.A., et al., "Cancer regression in patients after transfer of genetically engineered lymphocytes", Science, 314:126-129 (2006).

Muyldermans, Serge, et al., "Recognition of Antigens by Single-Domain Antibody Fragments: The Superfluous Luxury of Paired Domains", Trends Biochem. Sci., 26(4) 230 (2001).

Newberg, M.H., et al., "Importance of MHC class 1 alpha2 and alpha3 domains in the recognition of self and non-self MHC molecules", J Immunol, 156:2473-2480 (1996).

Newmark, J., et al., Preparation and Properties of Adducts of Streptokinase and Streptokinase-Plasmin complex with Polyethylene glycol and Pluronic Polyol F38, Journal of Applied Biochemistry, 4, 185-189 (1982).

Non-Final Rejection Mailed on Jan. 29, 2020 for U.S. Appl. No. 15/969,211.

Notice of Allowance received for U.S. Appl. No. 15/969,211, mailed on Feb. 18, 2021, 9 pages.

Nuttall, S.D., et al., "Immunoglobulin V11 Domains and Beyond: Design and Selection of Single-Domain Binding and Targeting Reagents", Cur. Pharm. Biotech., 1, 253-263 (2000).

Office Action received in ID P00201910661 mailed on Jun. 9, 2021 (2 pages of English Translation, 2 pages of Original Document).

Pardee, A.D., et al., "Immunotherapy of hepatocellular carcinoma: Unique challenges and clinical opportunities", Oncoimmunology, 1:48-55 (2012).

Pardoll, D.M., et al., "The blockade of immune checkpoints in cancer immunotherapy", Nat Rev Cancer, 12:252-264 (2012).

Parkhurst, M.R., et al., "T cells targeting carcinoembryonic antigen can mediate regression of metastatic colorectal cancer but induce severe transient colitis", Mol Ther, 19:620-626 (2011).

Pichard, V., et al., "Detection, isolation, and characterization of the alpha-fetoprotein-specific T cell populations and clones using MHC class I multimer magnetic sorting", J Immunother, 31:246-253 (2008).

Pico de Coana Y., et al., "Checkpoint blockade for cancer therapy: revitalizing a suppressed immune system", Trends Mol Med, 21:482-491 (2015). (Abstract Only).

Office Action received for Indonesian Patent Application No. P00201910661, mailed on Oct. 23, 2021, 9 pages (3 pages of English Translation and 6 pages of Original Document).

Office Action received for European Patent Application No. 18799369, mailed on Sep. 1, 2022, 4 pages.

Office Action received for Indonesian Patent Application No. P00201910661, mailed on Mar. 29, 2023, 6 pages (3 pages of English Translation and 3 pages of Original Document).

Office Action received for Korean Patent Application No. 10-2019-7035091, mailed on Mar. 23, 2023, 18 pages (10 pages of English Translation and 8 pages of Original Document).

Piepenbrink, K.H., et al., "The basis for limited specificity and MHC restriction in a T cell receptor interface", Nature, 4: 1948 (2013).

Portolano, S., et al., "Lack of promiscuity in autoantigen-specific H and L chain combinations as revealed by human H and L chain 'roulette'", J Immunol. 150(3): 880-887 (1993).

Rapoport, A.P., et al., "NY-ESO-1-specific TCR-engineered T cells mediate sustained antigen-specific antitumor effects in myeloma", Nat Med, 21:914-921 (2015).

Requirement for Restriction/Election Mailed on Sep. 26, 2019 for U.S. Appl. No. 15/969,211.

(56) References Cited

OTHER PUBLICATIONS

Restifo, N.P., et al., "Adoptive immunotherapy for cancer: harnessing the T cell response", Nat Rev Immunol, 12:269-281 (2012).
Riechmann Lutz, et al., "Single Domain antibodies: comparison of Camel VH and Camelised Human VH Domains", J. Immunol. Meth. 231: 25-38 (1999).
Robbins, P.F., et al., "A pilot trial using lymphocytes genetically engineered with an NY-ESO-1 reactive T-cell receptor. long-term follow-up and correlates with response", Clin Cancer Res, 21:1019-1027 (2015).
Robbins, P.F., et al., "Single and dual amino acid substitutions in TCR CDRs can enhance antigen-specific T cell functions", J Immunol, 180:6116-6131 (2008).
Robbins, P.F., et al., "Tumor regression in patients with metastatic synovial cel sarcoma and melanoma using Jenetically engineered lymphocytes reactive with NY-ESO-1", J Clin Oncol, 29:917-924 (2011).
Schumacher, T.N., "T-cell-receptor gene therapy", Nat Rev Immunol, 2:512-519 (2002).
Shao, Y.Y., et al., "Early alpha-fetoprotein response predicts treatment efficacy of antiangiogenic systemic therapy in patients with advanced hepatocellular carcinoma", Cancer, 116:4590-4596 (2010).
Sharpe, M., et al., "Genetically modified T cells in cancer therapy: opportunities and challenges", Dis Model Mech, 8:337-350 (2015).
Sun, L., et al., "Engineered cytotoxic T lymphocytes with AFP-specific TCR gene for adoptive immunotherapy in hepatocellular carcinoma", Tumour Biol, 37:799-806 (2016).
Theobald, M., et al., "Targeting p53 as a general tumor antigen", Proc Natl Acad Sci USA, 92:11993-11997 (1995).
Torre, LA, et al., "Global Cancer Statistics", CA Cancer J Clin, 65:87-108 (2012).
Vora, S.R., et al., "Serum alpha-fetoprotein response as a surrogate for clinical outcome in patients receiving systemic therapy for advanced hepatocellular carcinoma", Oncologist, 14:717-725 (2009).
Walchli, S., et al., "A practical approach to T-cell receptor cloning and expression", PLoS One, 6:e27930 (2011).
Welzel (Trademark), et al., "Population-attributable fractions and risk factors for hepatocellular carcinoma in the United States", Am J Gastroenterol, 108:1314-1321 (2013).
White, J., et al., "Production and characterization of T cell hybridomas", Methods Mol Biol, 134:185-193 (2000).
Yang, Y., "Cancer immunotherapy:harnessing the immune system to battle cancer", J Clin Invest, 125:3335-3337 (2015).
Zhao, Y., et al., "High-affinity TCRs generated by phage display provide CD4+ T cells with the ability to recognize and kill tumor cell lines", J Immunol, 179:5845-5854 (2007).
Zhu et al., "Identification of [alpha]-fetoprotein-specific T-cell receptors for hepatocellular carcinoma immunotherapy", Hepatology, vol. 68, No. 2, Feb. 14, 2018, pp. 574-589.

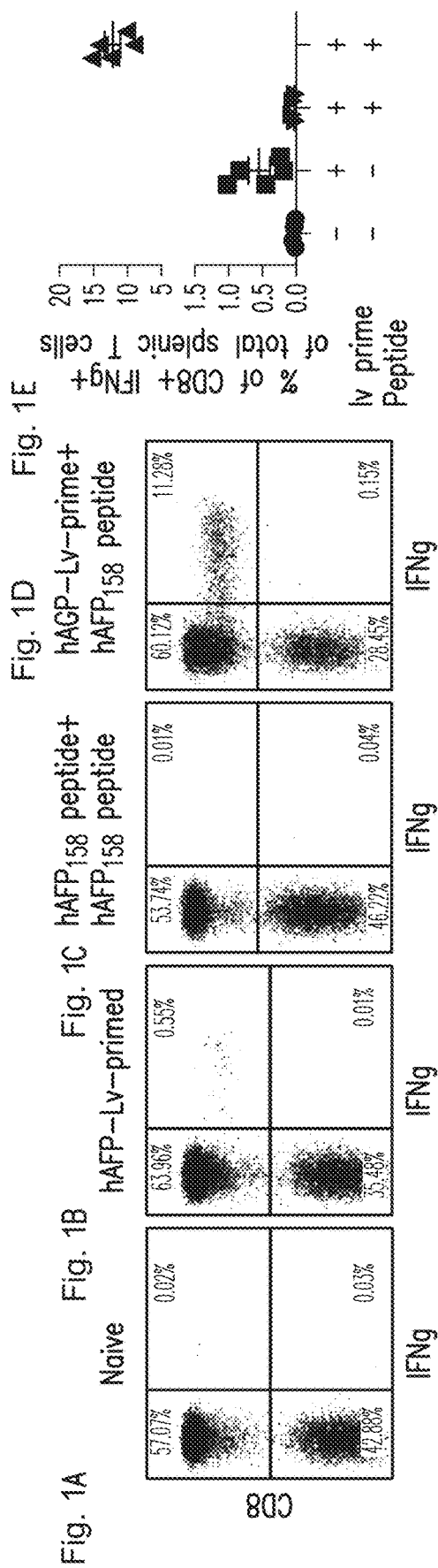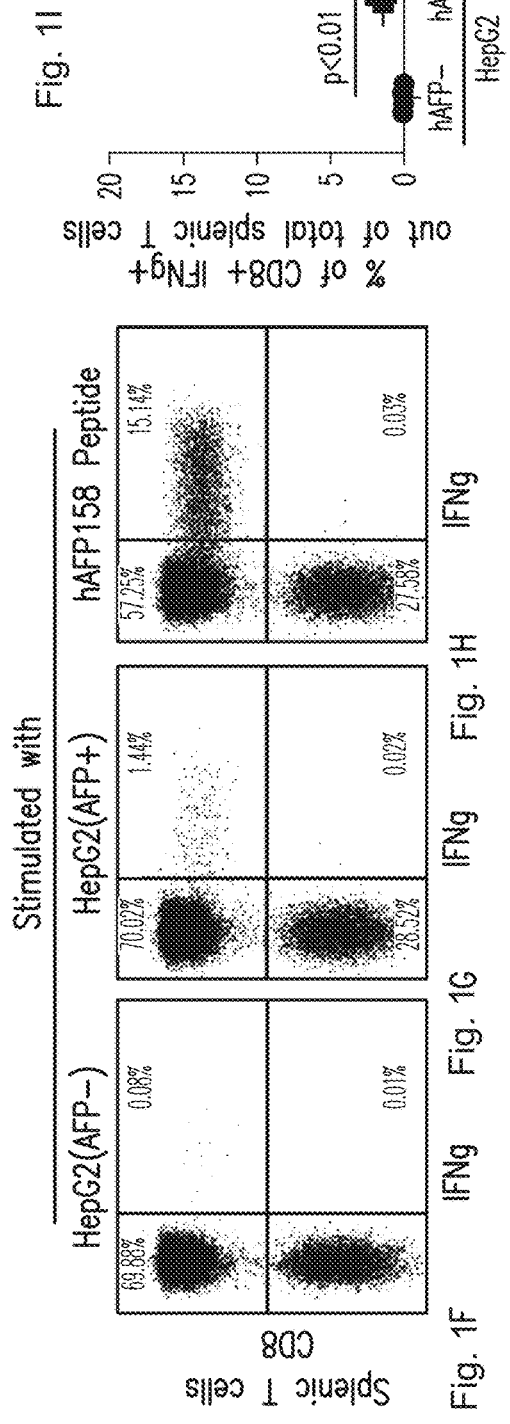

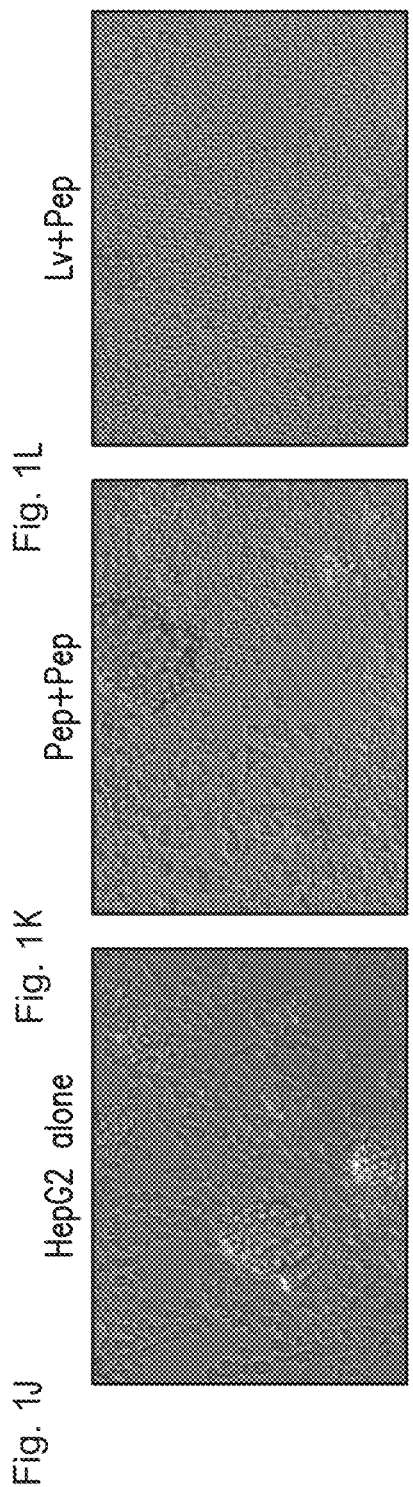
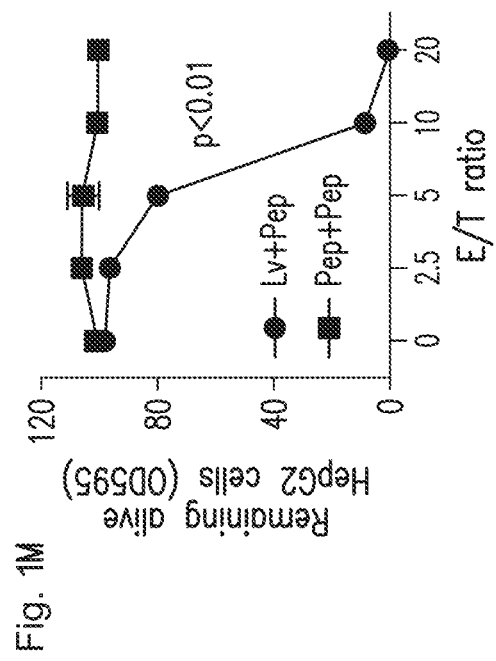
Fig. 1J  Fig. 1K  Fig. 1L
Fig. 1M

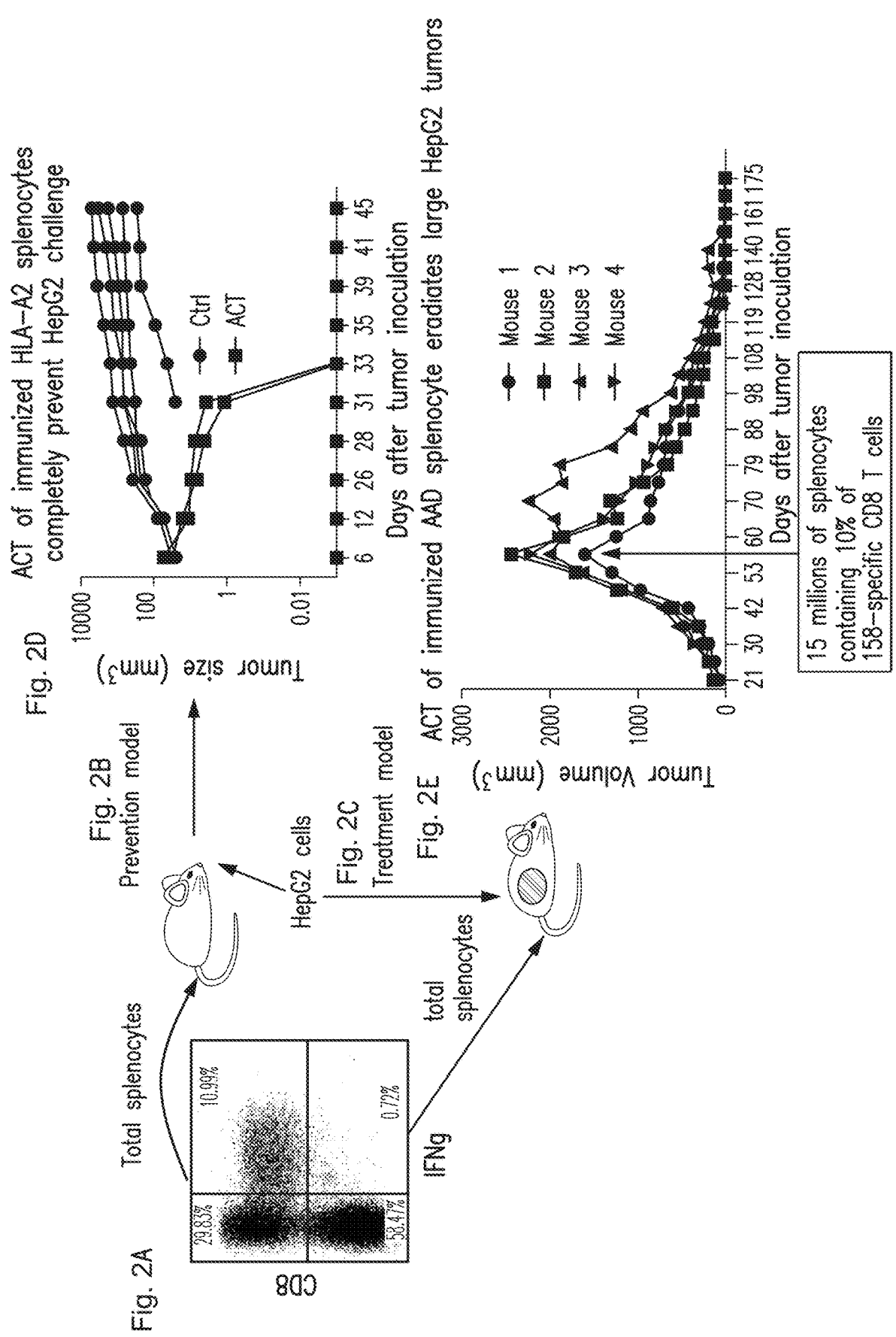

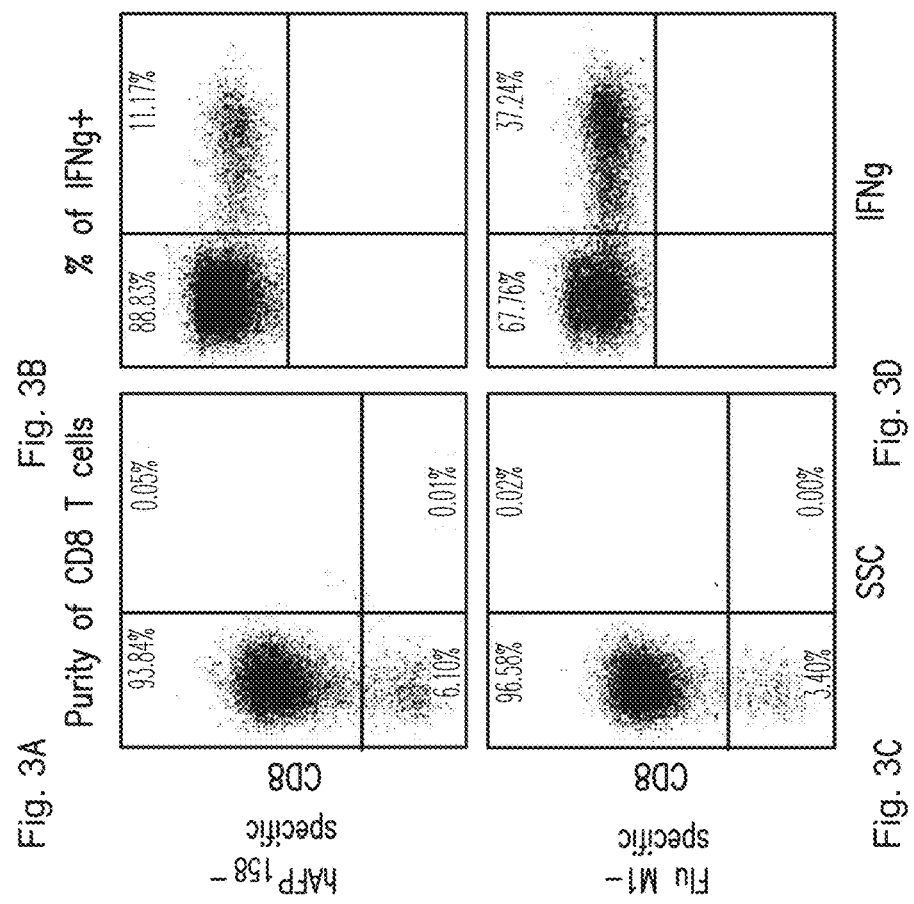

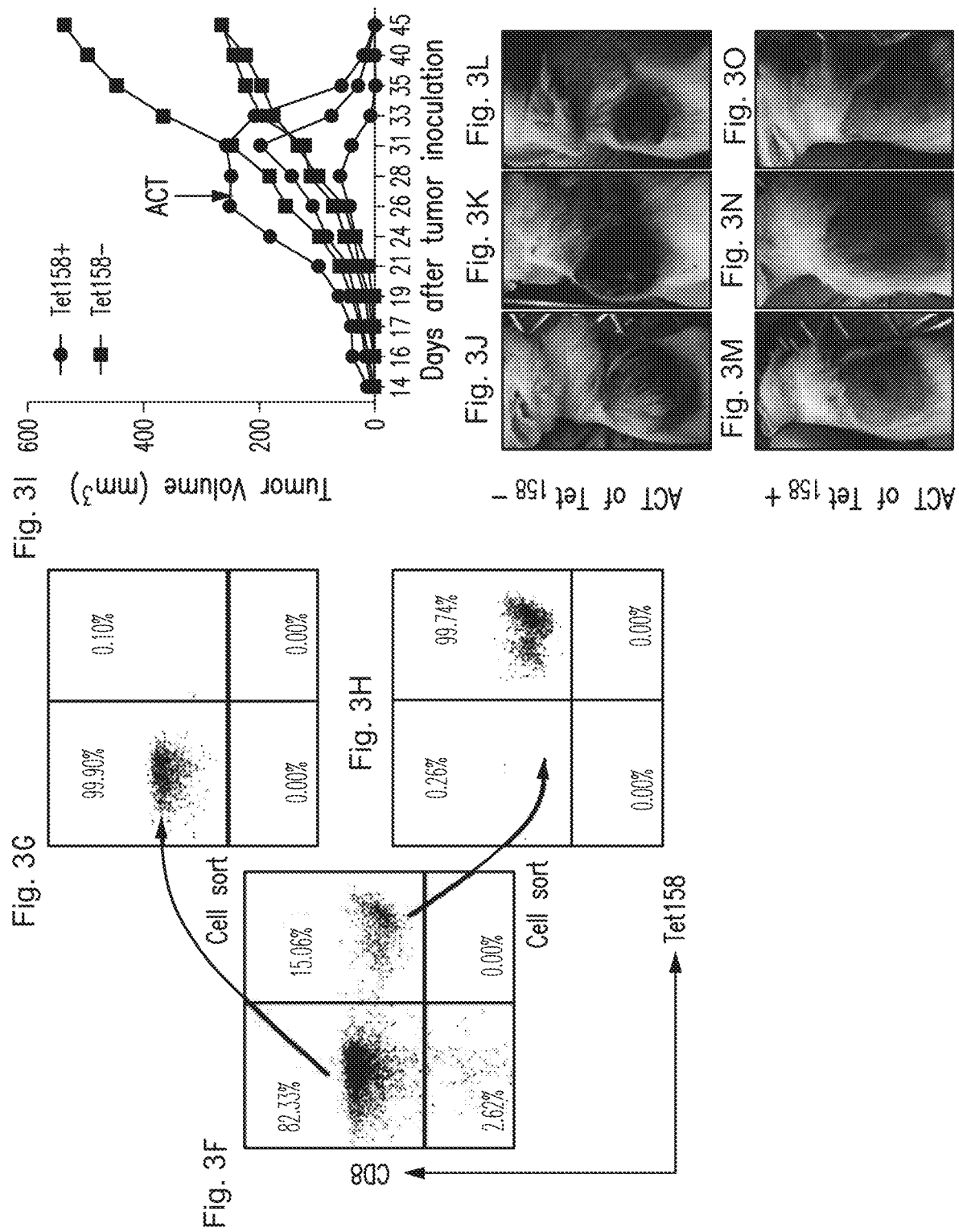

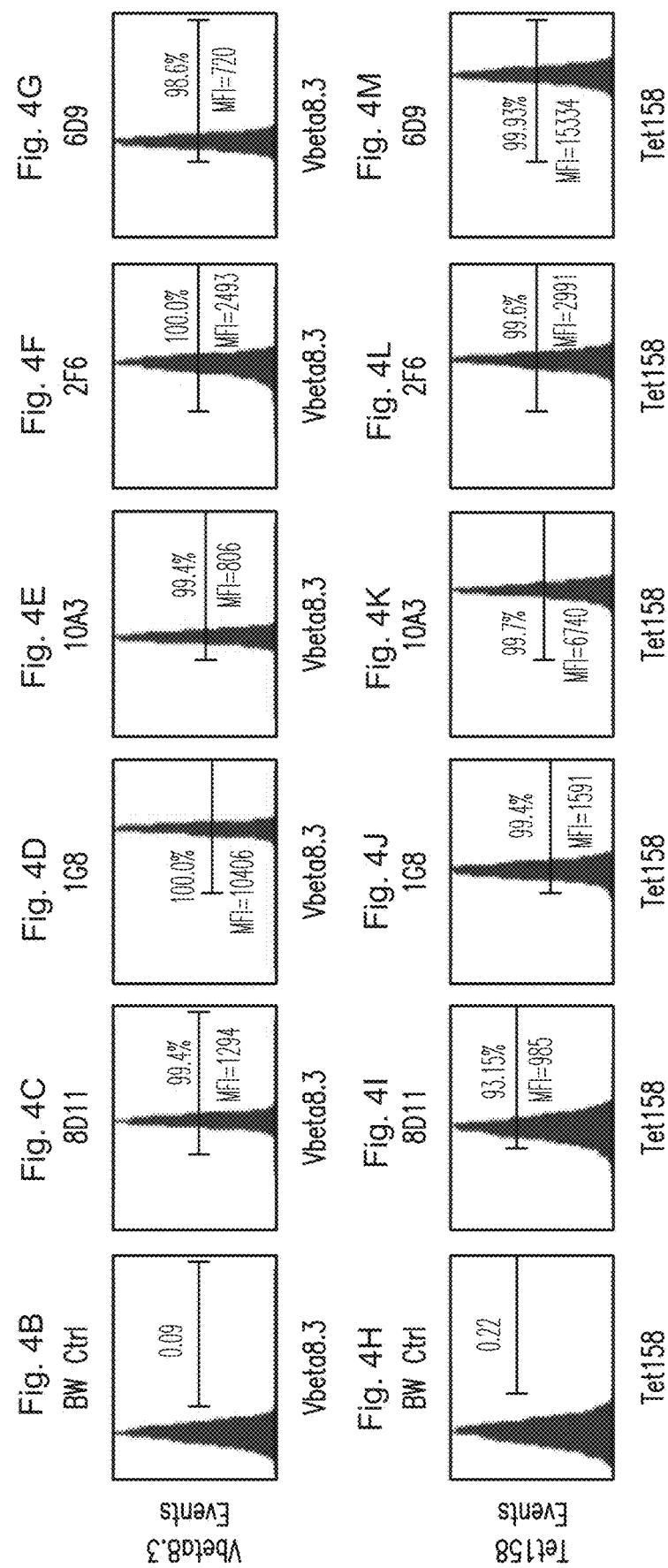

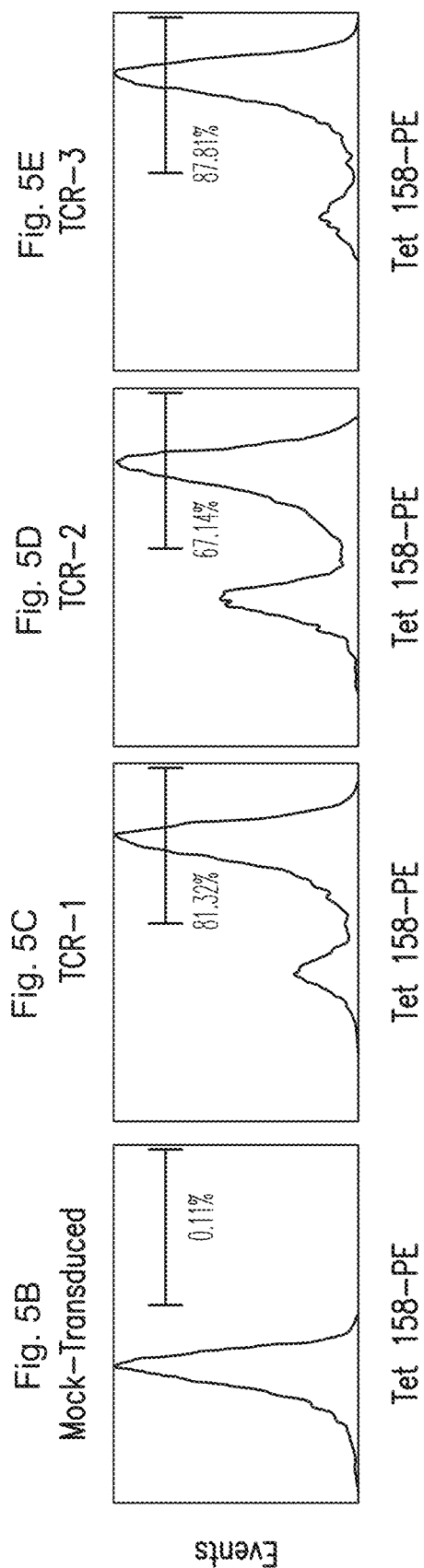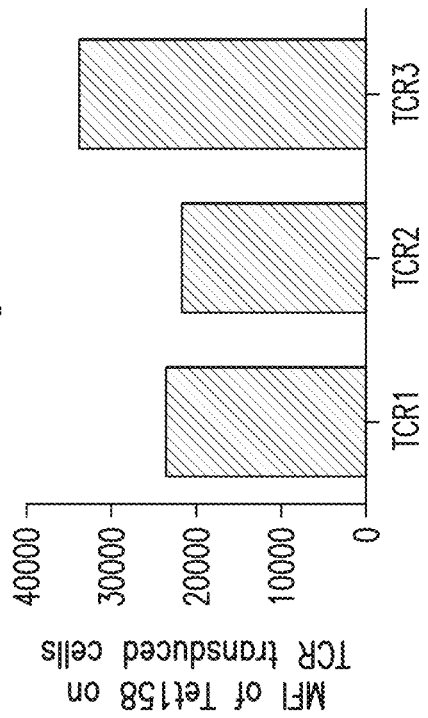

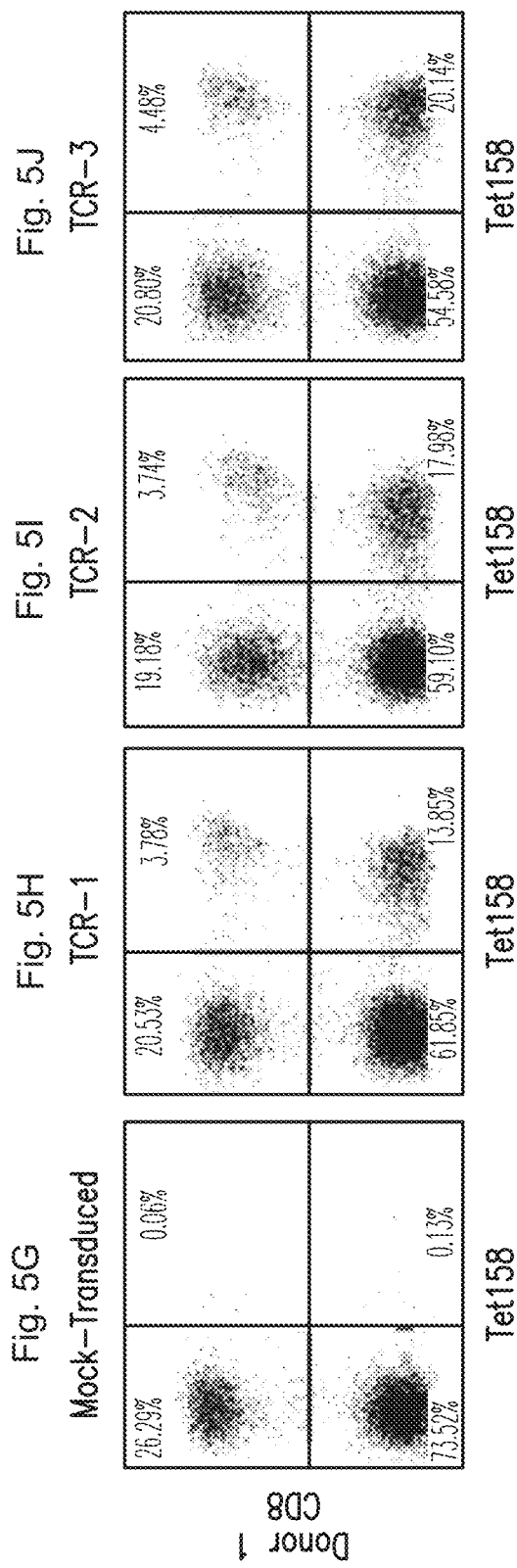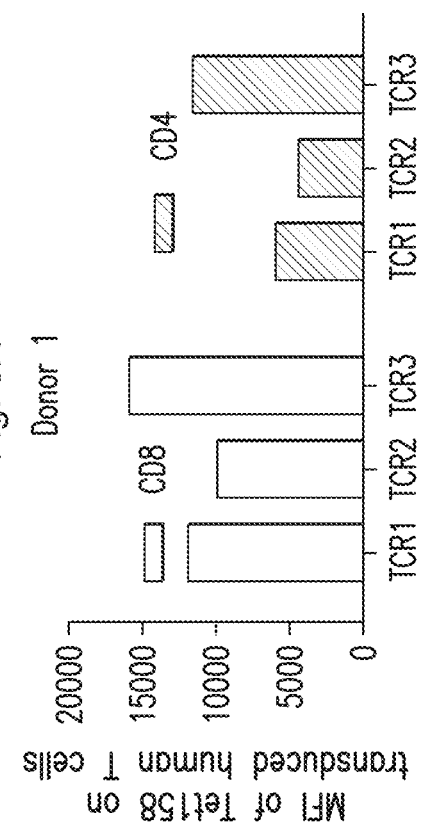

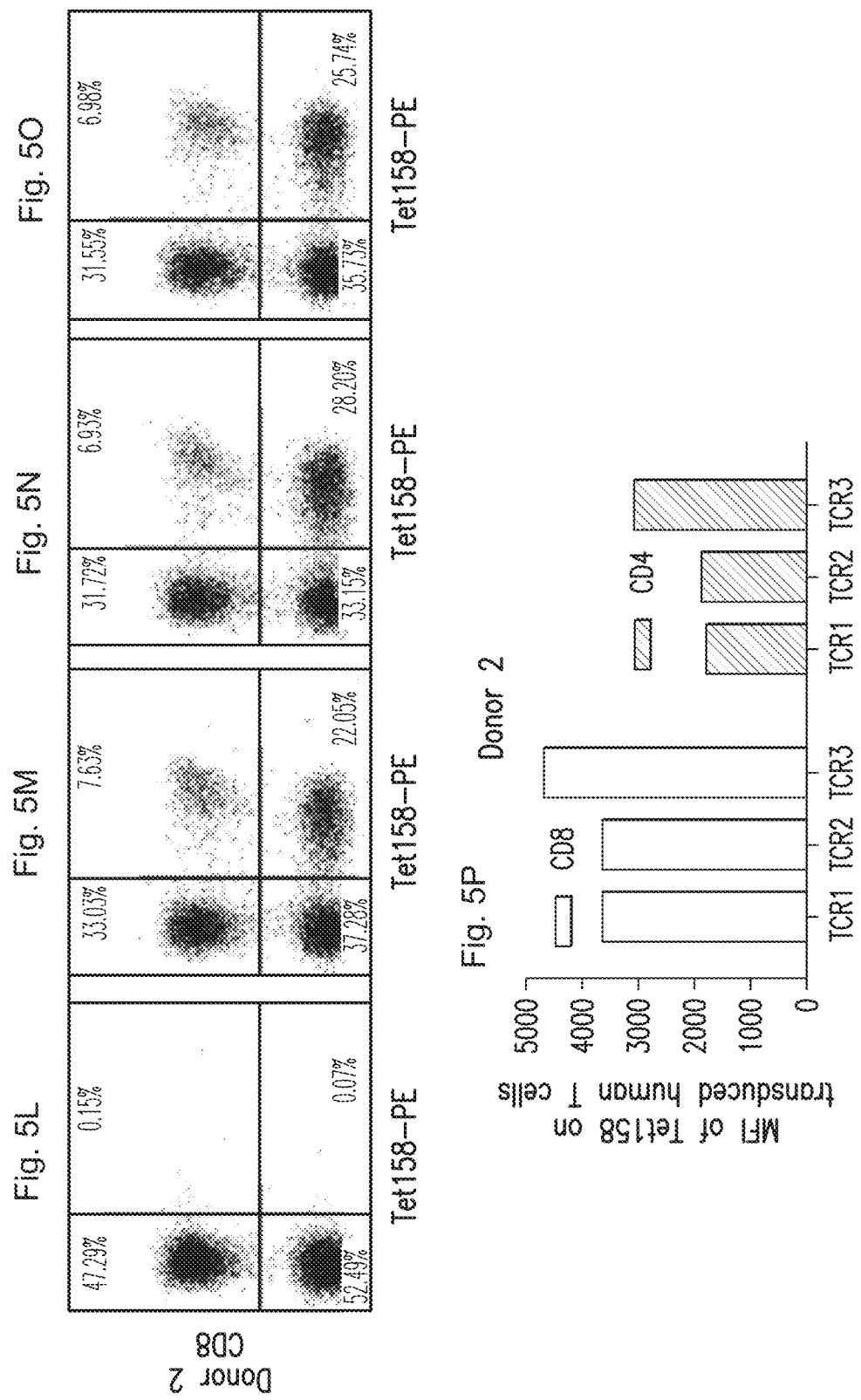

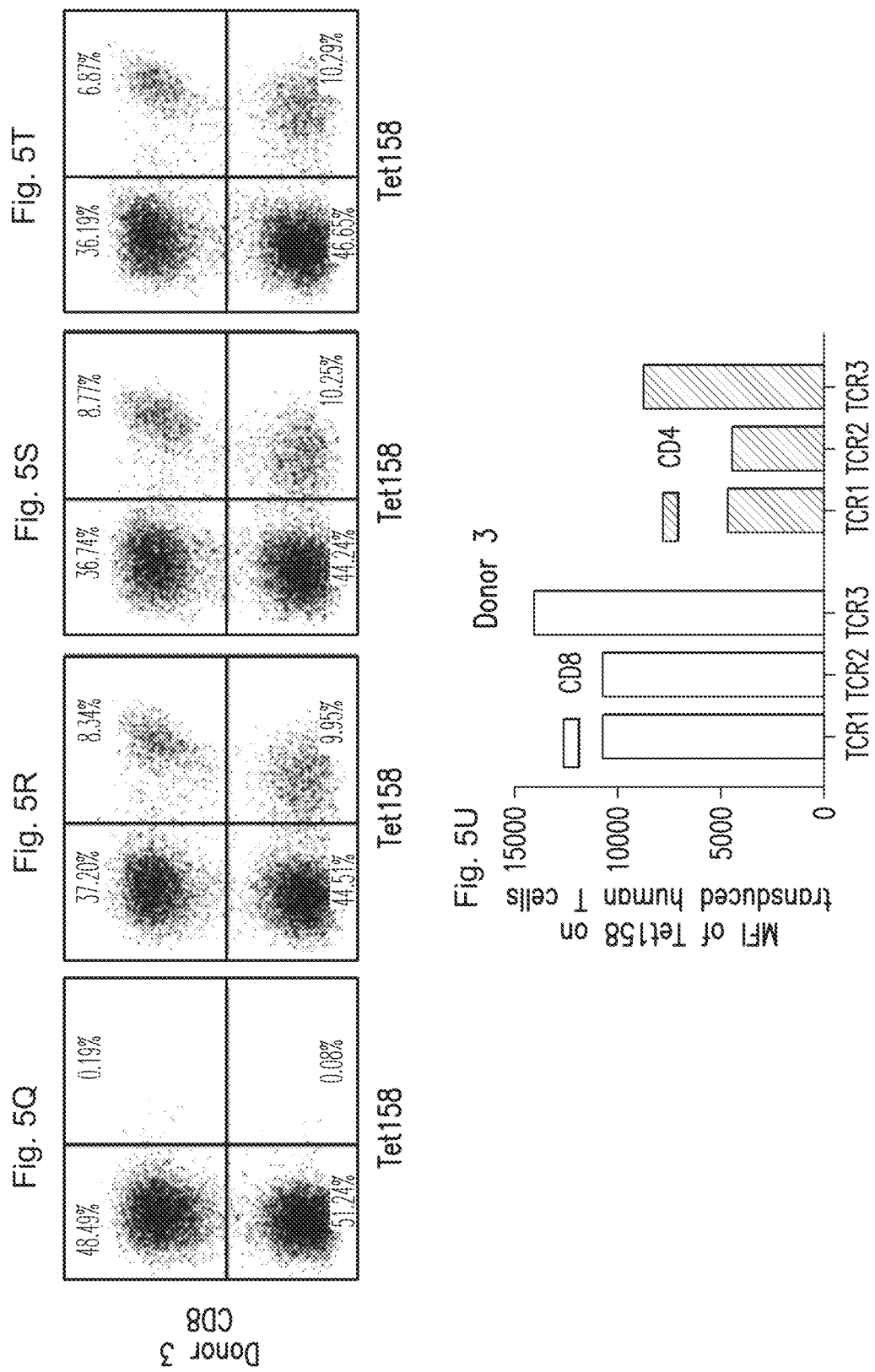

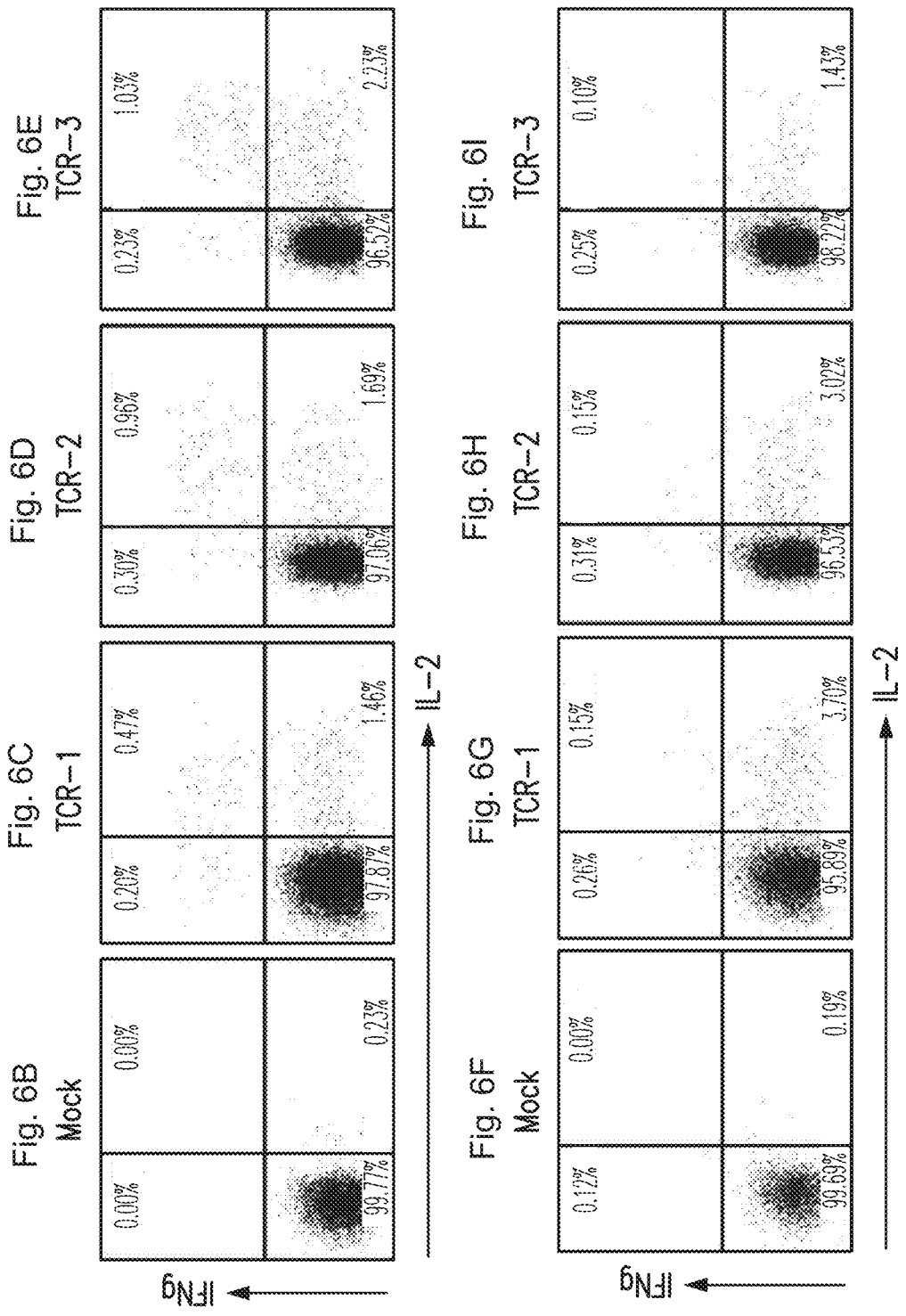

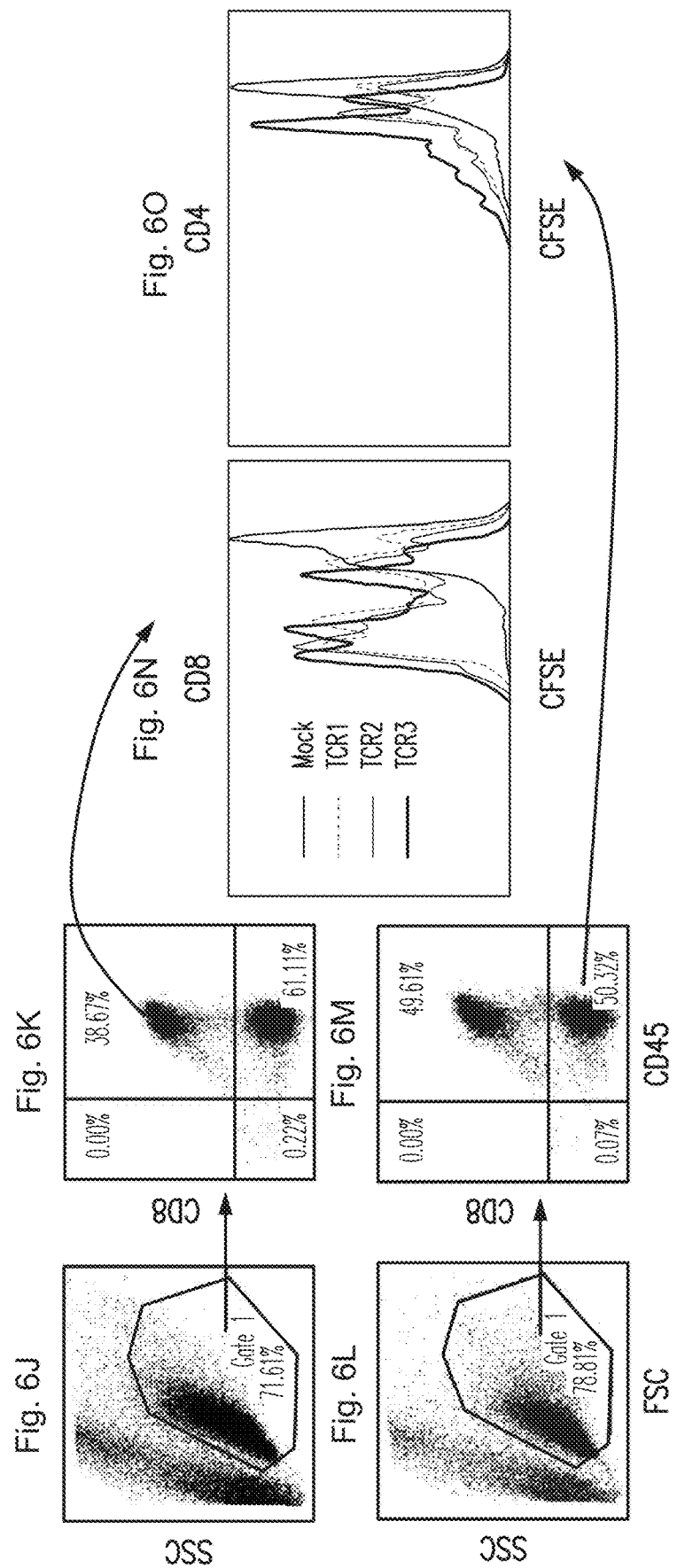

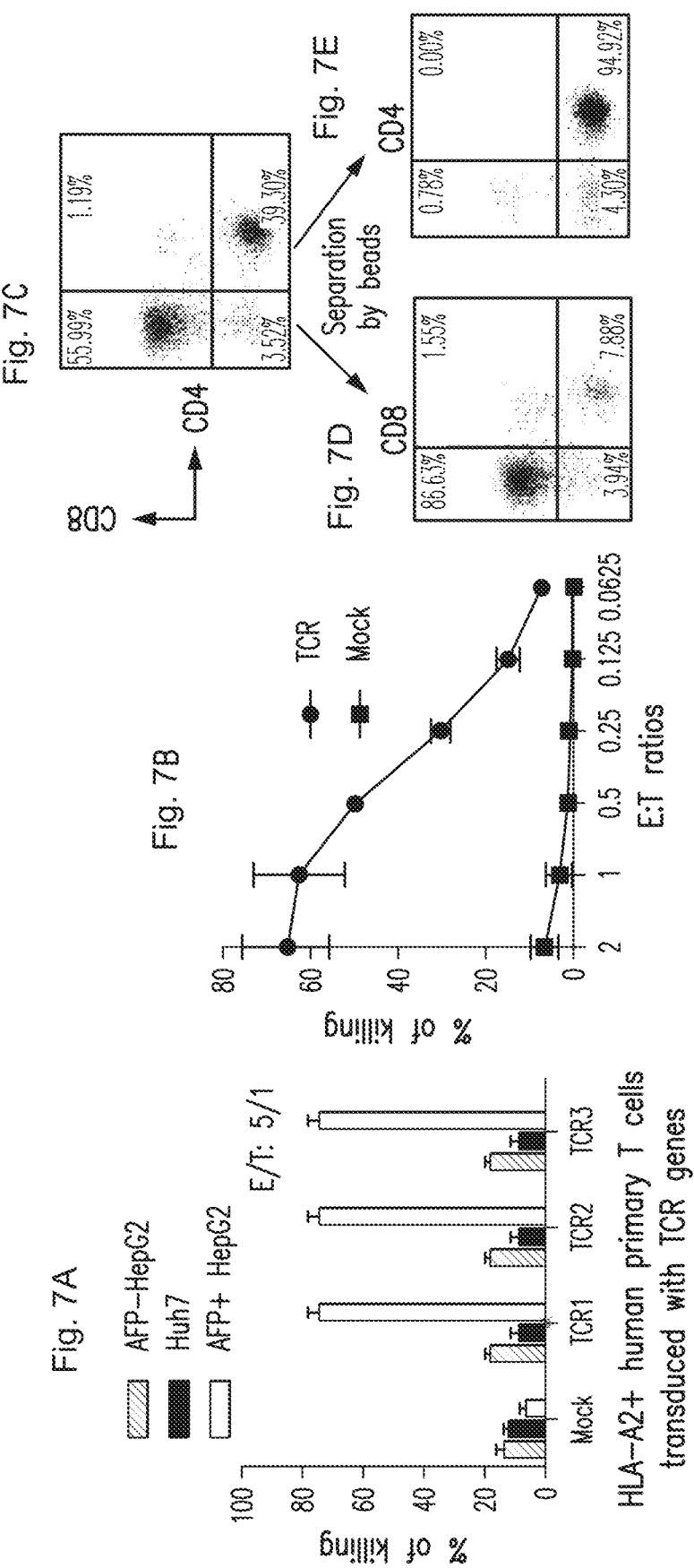

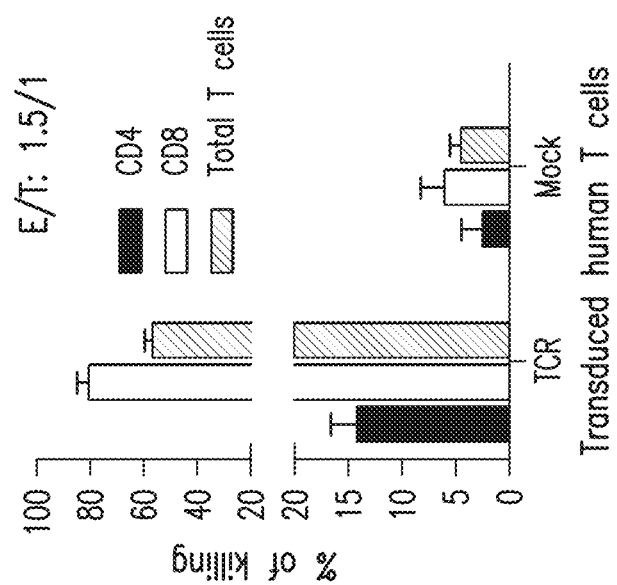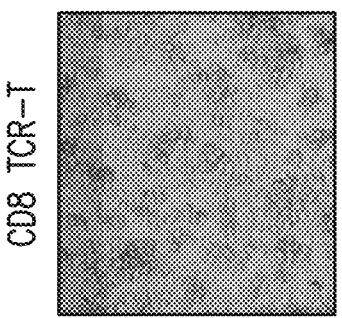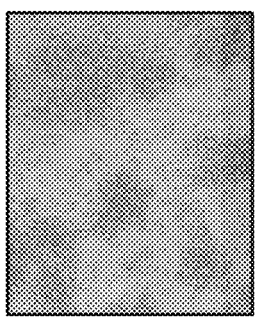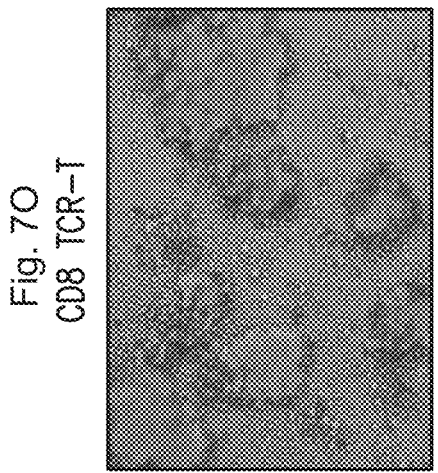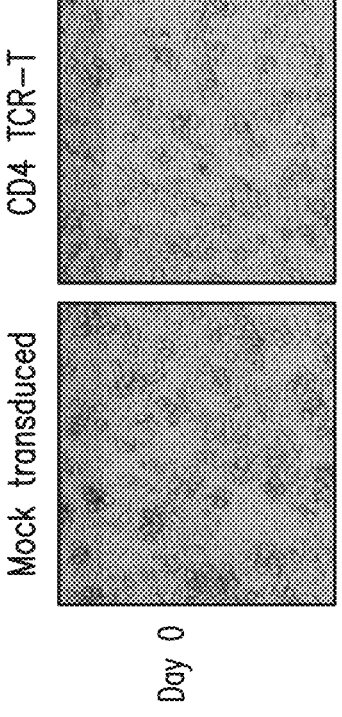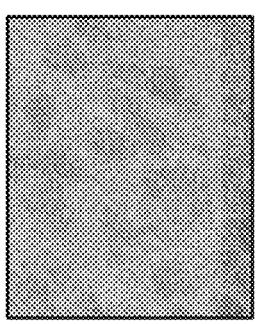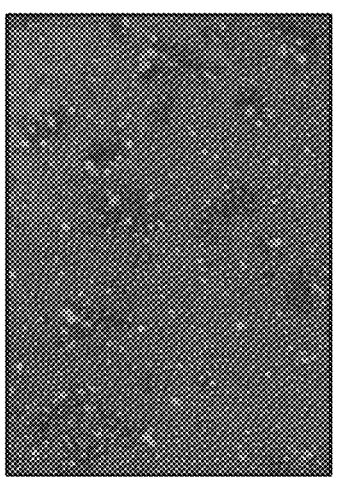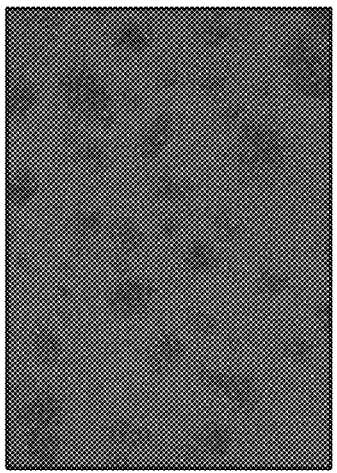

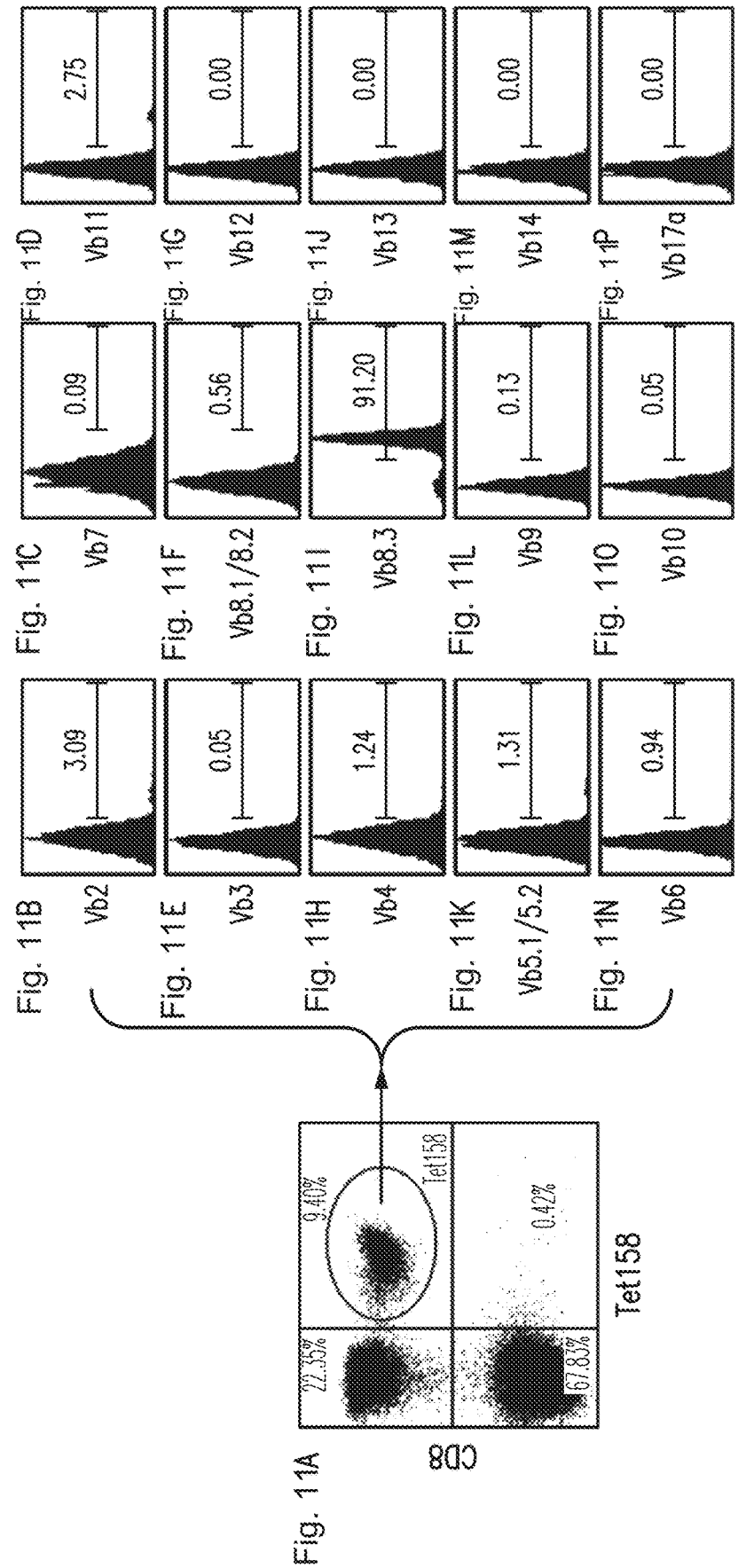

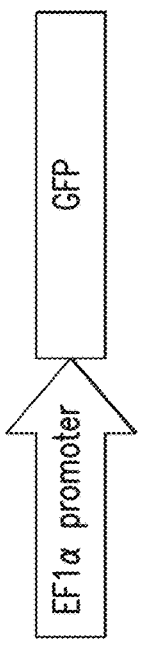
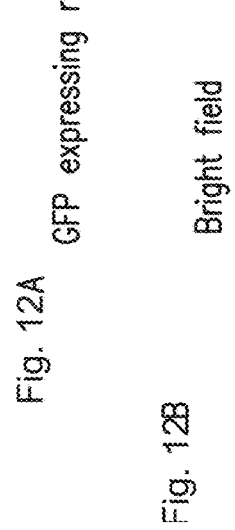
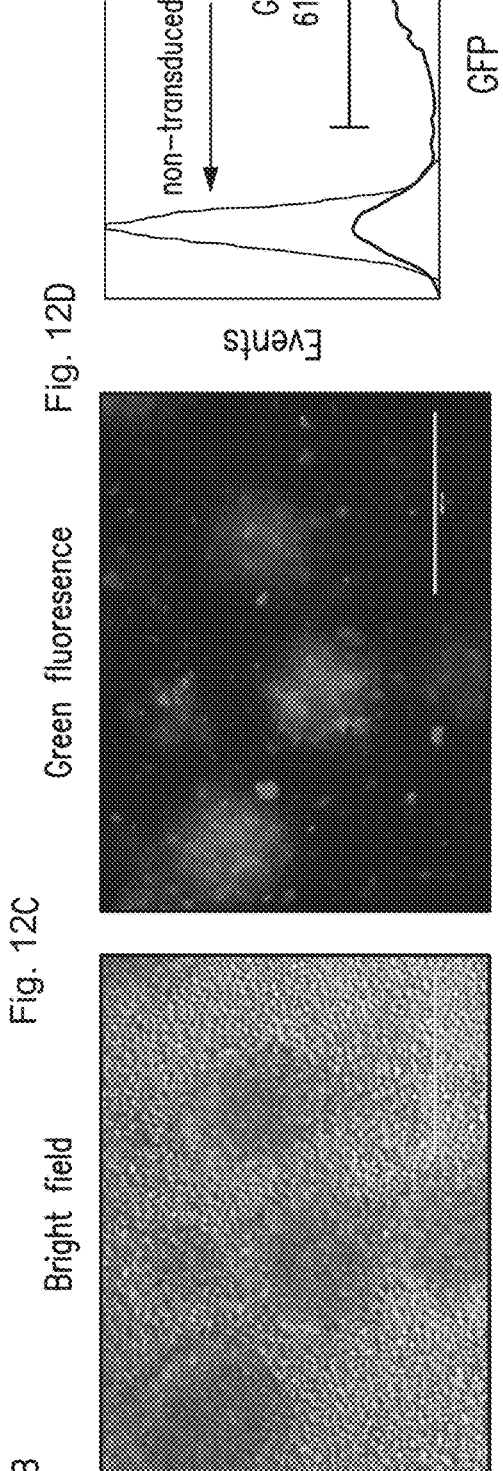
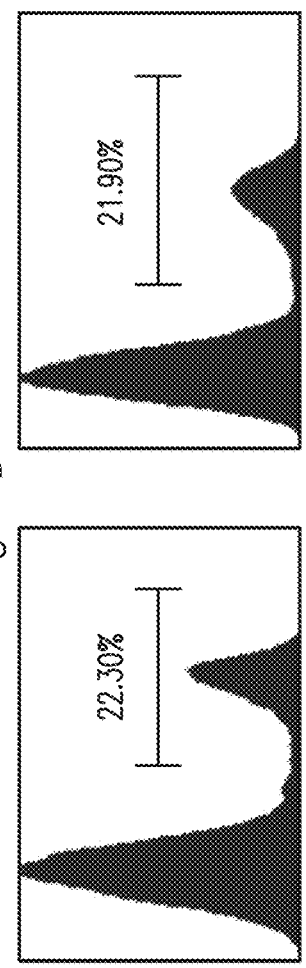
FIG. 12A-12D
FIG. 13A-13B

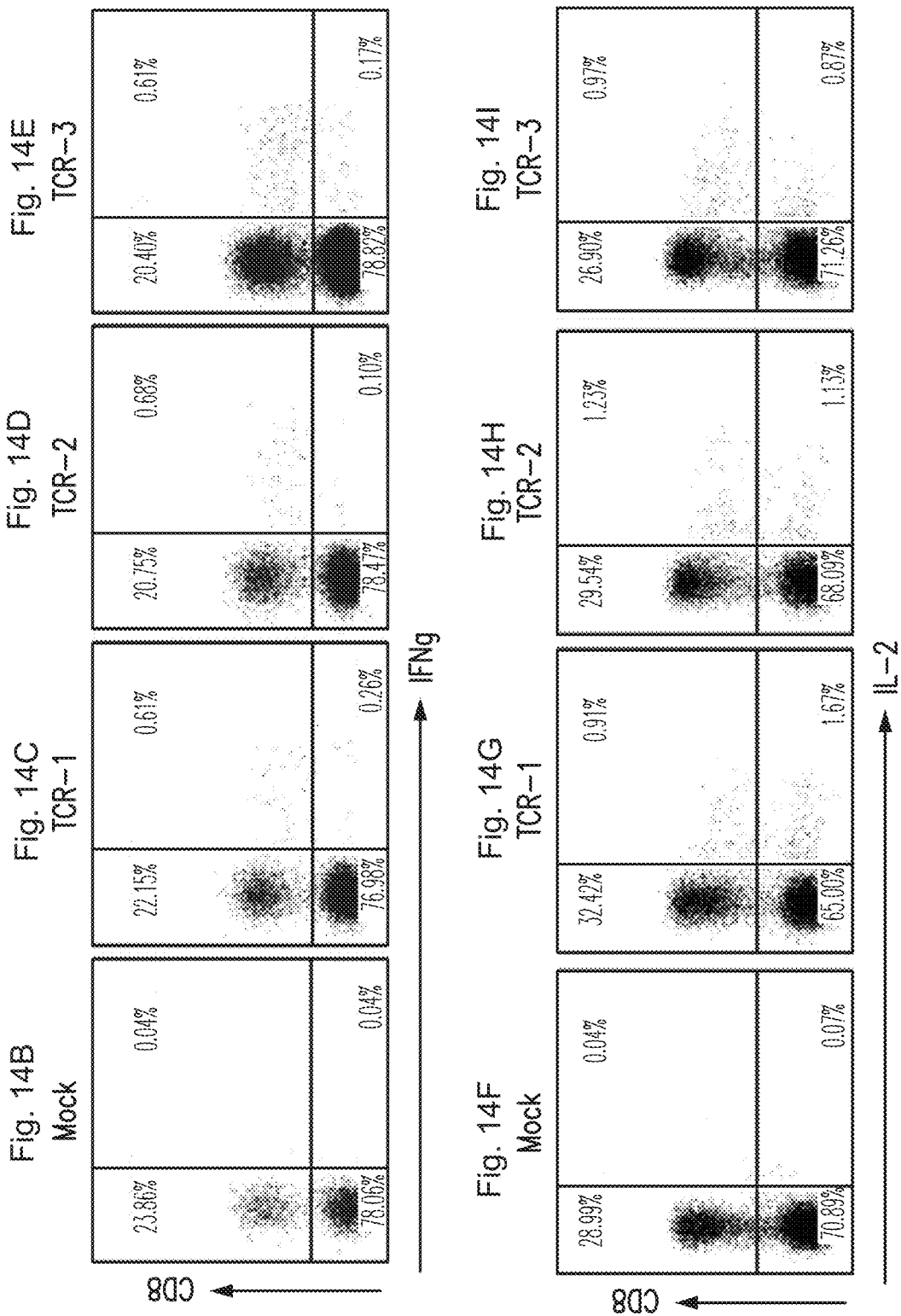

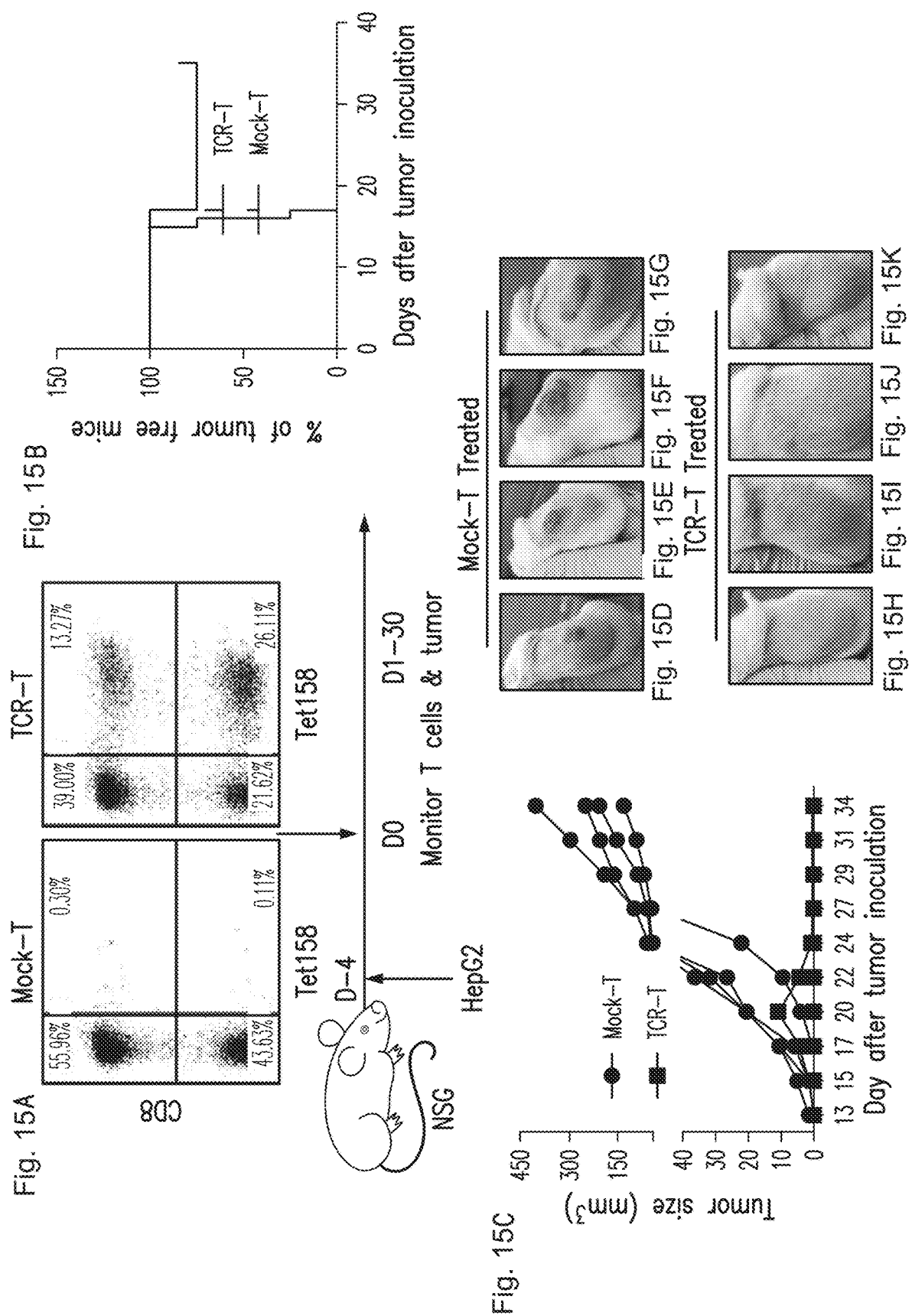

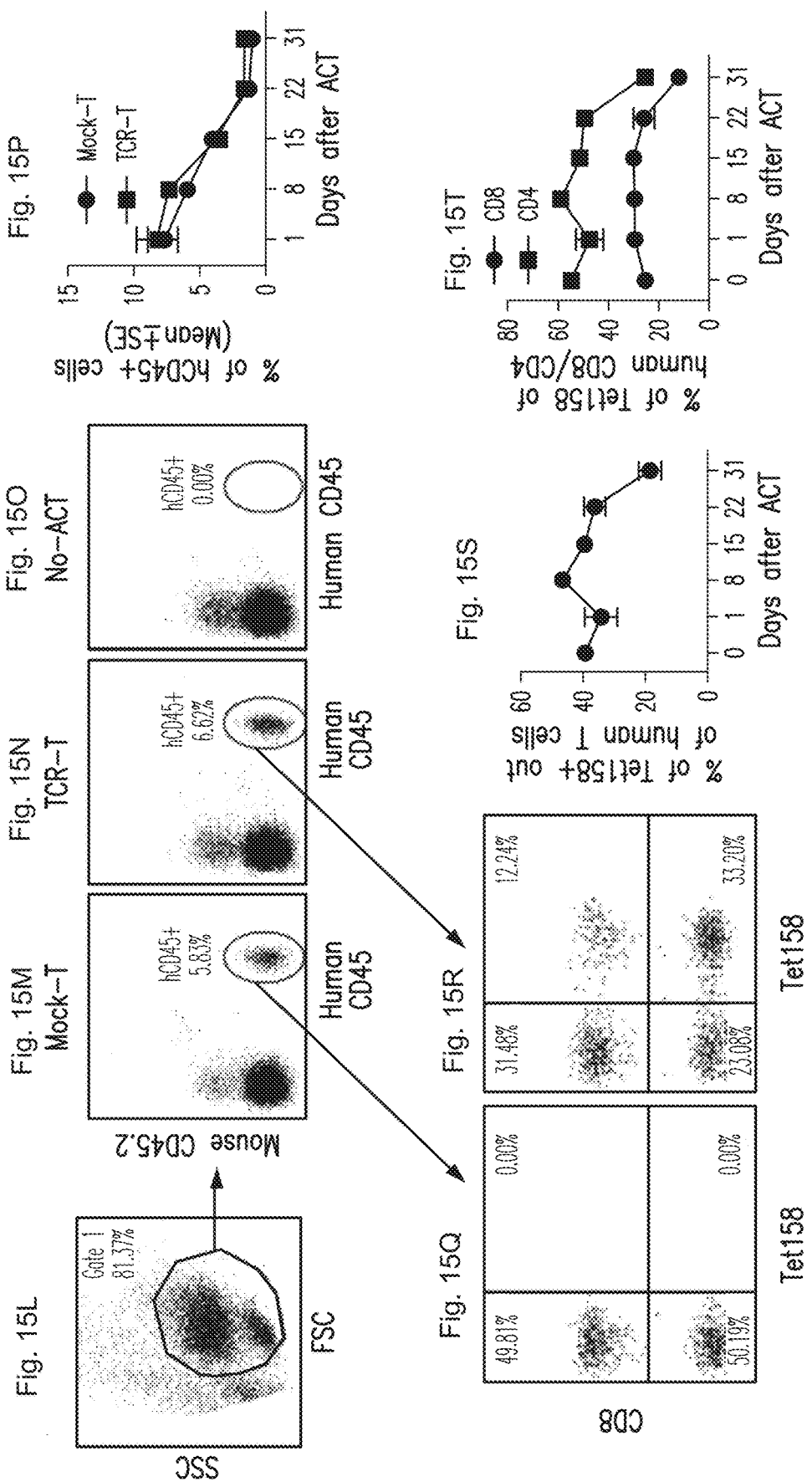

CDR3 OF TCR α chains

```
            81      91      101      111
            |       |       |        |
TCR-1   PSDSALYLCAASITNAYKVIFGKGTHLHVLPNIQNPEPAV   SEQ ID NO:93
TCR-2   PSDSALYLCAASTVNAYKVIFGKGTHLHVLPNIQNPEPAV   SEQ ID NO:94
TCR-6   PSDSALYLCAASMINAYKVIFGKGTHLHVLPNIQNPEPAV   SEQ ID NO:95
TCR-3   PSDSALYLCAASMAGGYKVVFGSGTRLLVSPDIQNPEPAV   SEQ ID NO:96
TCR-8   PSDSALYLCAASISGGYKVVFGSGTRLLVSPDIQNPEPAV   SEQ ID NO:97
TCR-10  PSDSALYLCAASIVGGYKVVFGSGTRLLVSPDIQNPEPAV   SEQ ID NO:98
TCR-11  PSDSALYLCAASKTGGYKVVFGSGTRLLVSPDIQNPEPAV   SEQ ID NO:99
TCR-17  PSDSALYLCAASMTGGYKVVFGSGTRLLVSPDIQNPEPAV   SEQ ID NO:100
TCR-38  PSDSALYLCAATLTGGYKVVFGSGTRLLVSPDIQNPEPAV   SEQ ID NO:101
```

FIG. 17A

CDR3 OF TCR β chains

```
            85      95      105      115
            |       |       |        |
TCR-1   SQTSLYFCASSDAGTSQNTLYFGAGTRLSVLEDLRNVTPP   SEQ ID NO:102
TCR-2   SQTSLYFCASSDAGTSQNTLYFGAGTRLSVLEDLRNVTPP   SEQ ID NO:102
TCR-6   SQTSLYFCASSDAGVSQNTLYFGAGTRLSVLEDLRNVTPP   SEQ ID NO:103
TCR-3   SQTSLYFCASSDAGTAQNTLYFGAGTRLSVLEDLRNVTPP   SEQ ID NO:104
TCR-8   SQTSLYFCASSDAGTSQNTLYFGAGTRLSVLEDLRNVTPP   SEQ ID NO:102
TCR-10  SQTSLYFCASSDHGTGQNTLYFGAGTRLSVLEDLRNVTPP   SEQ ID NO:105
TCR-11  SQTSLYFCASSDAGVSQNTLYFGAGTRLSVLEDLRNVTPP   SEQ ID NO:103
TCR-17  SQTSLYFCASSDAGTSQNTLYFGAGTRLSVLEDLRNVTPP   SEQ ID NO:102
TCR-38  SQTSLYFCASSDAGTSQNTLYFGAGTRLSVLEDLRNVTPP   SEQ ID NO:102
```

FIG. 17B

HUMAN ALPHA FETOPROTEIN-SPECIFIC T CELL RECEPTORS AND USES THEREOF

CROSS-REFERENCE TO RELATED APPLICATIONS

This application is a divisional of U.S. Nonprovisional patent application Ser. No. 15/969,211 filed on May 2, 2018, now U.S. Pat. No. 11,041,011, which claims benefit of and priority to U.S. Provisional Application No. 62/505,406 filed on May 12, 2017, and to U.S. Provisional Application No. 62/609,614 filed on Dec. 22, 2017, and to U.S. Provisional Application No. 62/625,051 filed on Feb. 1, 2018, and where permitted all of which are incorporated by reference in their entireties.

STATEMENT REGARDING FEDERALLY SPONSORED RESEARCH

This invention was made with government support under R01CA168912 awarded by the National Institutes of Health. The government has certain rights in the invention.

SEQUENCE LISTING

The Sequence Listing submitted Sep. 27, 2021, as a text file named "Sequence listing 064466.067CON_ST25" created on Sep. 24, 2021, and having a size of 171,904 bytes is hereby incorporated by reference pursuant to 37 C.F.R. § 1.52(e)(5). The sequence information in the "Sequence listing" in this application is identical to the sequence information in the CRF in its priority patent application, U.S. patent application Ser. No. 15/969,211, which was filed on May 2, 2018 and is currently pending. Further, the inventors on U.S. patent application Ser. No. 15/969,211 are identical to the inventors of the instant Application.

TECHNICAL FIELD OF THE INVENTION

The invention is generally directed to immunology, in particular to T cell receptors and methods of their use in treating immune disorders including cancer.

BACKGROUND OF THE INVENTION

With ~800,000 new cases each year, hepatocellular carcinoma (HCC) is the 5th most common cancer in the world. In the US, according to American Cancer Society, the number of liver cancers (the majority of them are HCC) has doubled in last decade in the United States, representing one of the fast-growing malignancies—mainly due to the prevalence of obesity. The HCC incidence will likely remain high due to the large number of existing chronic HBV and HCV patients and the pandemic obesity. To make matters worse, the lack of effective management makes HCC the 2nd leading cause of cancer death in adult men. Thus, there is an urgent need to develop novel therapies. Adoptive transfer of tumor-specific T cells has great potential of controlling tumor growth without significant toxicity. Because of the difficulty of isolating tumor-specific T cells from most solid tumors (other than the melanoma), genetically engineering patient's autologous T cells with tumor antigen-specific TCR genes will likely provide the functional tumor-specific T cells for adoptive cell transfer immunotherapy.

HCC frequently re-expresses human glypican 3 (hGPC3) and human alpha fetoprotein (hAFP) as tumor associated antigens (TAAs). These antigens not only serve as biomarkers for diagnosis, but can also be targets for immunotherapy. Recently, hGPC3-specific human TCR genes were cloned and demonstrated antitumor efficacy using a xenografted HCC model in immune compromised mice (Dargel et al., 2015). However, because TAAs are often not expressed at equal levels throughout an HCC, anti-hGPC3 treatment may select hGPC3-negative cells, causing relapse. In theory, using a combination of TCRs toward different epitopes and different tumor antigens can avoid or delay tumor immune escape. Four HLA-A2 restricted hAFP epitopes have been identified (Butterfield et al., 2001). The epitope $hAFP_{158}$ is frequently presented by HCC tumor cells and the $hAFP_{158}$-specific immune cells are found in HCC patients (Butterfield et al., 2003) though antitumor effect was weak (Butterfield et al., 2006) possibly because the human $hAFP_{158}$-specific T cells are low affinity. Thus, finding high affinity $hAFP_{158}$-specific TCR may increase antitumor efficacy of targeting AFP antigen. There are two $hAFP_{158}$-specific TCR genes that have been reported. One recent patent directed to human TCR specific for the $hAFP_{158}$ epitope (CN 104087592 A) showed limited antitumor effect (Sun et al., 2016). The weaker antitumor effect was further confirmed by another patent application from Adaptimmune Co (US 2016/0137715 A1), in which the wild type human TCR specific for $hAFP_{158}$ epitope did not produce any effector function when co-cultured with human HCC tumor cells. Thus, $hAFP_{158}$-specific high affinity TCRs were created and patented via mutating the CDR regions of wild type human TCR to increase the recognition of HCC tumor cells (US 2016/0137715 A1). But, no clinical data is available to show that such TCR modified human T cells (TCR-T) can indeed generate antitumor effect in vivo. Furthermore, in light of the recent reports that adoptive transfer of high affinity TCR-T cells has been associated with severe off-target toxicity (Cameron et al., 2013; Linette et al., 2013; Morgan et al., 2013), it is desirable to have more TCRs available to increase the chance of finding the optimal TCRs with high antitumor efficacy and low toxicity. Thus, there is a true demand for identifying additional TCRs specific for TAAs that can be used to engineer a patient's autologous T cells for immunotherapy.

SUMMARY OF THE INVENTION

T cell receptors that specifically recongnize $hAFP_{158}$ are provided. One embodiment provides an engineered murine T cell receptor (mTCR) Vα chain polypeptide having at least 90% sequence identity to SEQ ID NO:2, 3, 4, 5, 6, 7, 8, 9, or 10, wherein the mTCR specifically recognizes $hAFP_{158}$ (SEQ ID NO:1).

Another embodiment provides an engineered murine T cell receptor (mTCR) Vβ chain polypeptide having at least 90% sequence identity to SEQ ID NO:11, 12, 13, or 14, wherein the mTCR specifically recognizes $hAFP_{158}$ (SEQ ID NO:1).

Still another embodiment provides an engineered murine T cell receptor (mTCR) full length α chain polypeptide having at least 90% sequence identity to SEQ ID NO:15, 16, 17, 18, 19, 20, 21, 22, or 23, wherein the mTCR specifically recognizes $hAFP_{158}$ (SEQ ID NO:1).

Another embodiment provides an engineered murine T cell receptor (mTCR) full length R chain polypeptide having at least 90% sequence identity to SEQ ID NO:24, 25, 26, or 27, wherein the mTCR specifically recognizes $hAFP_{158}$ (SEQ ID NO: 1).

One embodiment provides an engineered murine T cell receptor (mTCR) α chain polypeptide having a CDR1 region with at least 90% sequence identity to DRNVDY (residues 47 to 52 of SEQ ID NO:2), a CDR2 region with at least 90% sequence identity to IFSNGE (residues 70 to 75 of SEQ ID NO:2), and a CDR3 region with at least 90% sequence identity to SEQ ID NO:28, 29, 30, 31, 32, 33, 34, 35, or 36, wherein the mTCR specifically recognizes hAFP$_{158}$ (SEQ ID NO:1).

Another embodiment provides an engineered murine T cell receptor (mTCR) β chain polypeptide having a CDR1 region with at least 90% sequence identity to NSHNY (residues 44 to 48 of SEQ ID NO:11), a CDR2 region with at least 90% sequence identity to SYGAGN (residues 66 to 71 of SEQ ID NO: 11), and a CDR3 region with at least 90% sequence identity to SEQ ID NO:37, 38, 39, or 40, wherein the mTCR specifically recognizes hAFP$_{158}$ (SEQ ID NO:1).

The leader sequence of any one of the disclosed polypeptide sequences can be removed.

One embodiment provides an engineered murine T cell receptor (mTCR) having a Vα domain having at least 90% sequence identity to SEQ ID NO:2, wherein the CDR3 region has at least 90% sequence identity to SEQ ID NO:28, and a Vβ domain having at least 90% sequence identity to SEQ ID NO:11, wherein the CDR3 region has at least 90% sequence identity to SEQ ID NO:37.

Another embodiment provides an engineered murine T cell receptor (mTCR) having a Vα domain having at least 90% sequence identity to SEQ ID NO:3, wherein the CDR3 region has at least 90% sequence identity to SEQ ID NO:29, and a Vβ domain having at least 90% sequence identity to SEQ ID NO:11, wherein the CDR3 region has at least 90% sequence identity to SEQ ID NO:37.

Another embodiment provides an engineered murine T cell receptor (mTCR) having a Vα domain having at least 90% sequence identity to SEQ ID NO:4, wherein the CDR3 region has at least 90% sequence identity to SEQ ID NO:30, and a Vβ domain having at least 90% sequence identity to SEQ ID NO:12, wherein the CDR3 region has at least 90% sequence identity to SEQ ID NO:38.

Still another embodiment provides an engineered murine T cell receptor (mTCR) having a Vα domain having at least 90% sequence identity to SEQ ID NO:5, wherein the CDR3 region has at least 90% sequence identity to SEQ ID NO:31, and a Vβ domain having at least 90% sequence identity to SEQ ID NO:13, wherein the CDR3 region has at least 90% sequence identity to SEQ ID NO:39.

One embodiment provides an engineered murine T cell receptor (mTCR) having a Vα domain having at least 90% sequence identity to SEQ ID NO:6, wherein the CDR3 region has at least 90% sequence identity to SEQ ID NO:32, and a Vβ domain having at least 90% sequence identity to SEQ ID NO:11, wherein the CDR3 region has at least 90% sequence identity to SEQ ID NO:37.

Some embodiment provide an engineered murine T cell receptor (mTCR) having a Vα domain with at least 90% sequence identity to SEQ ID NO:7, wherein the CDR3 region has at least 90% sequence identity to SEQ ID NO:33, and a Vβ domain having at least 90% sequence identity to SEQ ID NO:14, wherein the CDR3 region has at least 90% sequence identity to SEQ ID NO:40.

Another embodiment provides an engineered murine T cell receptor (mTCR) having a Vα domain having at least 90% sequence identity to SEQ ID NO:8, wherein the CDR3 region has at least 90% sequence identity to SEQ ID NO:34, and a Vβ domain having at least 90% sequence identity to SEQ ID NO:11, wherein the CDR3 region has at least 90% sequence identity to SEQ ID NO:37.

Yet another embodiment provides an engineered murine T cell receptor (mTCR) having a Vα domain having at least 90% sequence identity to SEQ ID NO:9, wherein the CDR3 region has at least 90% sequence identity to SEQ ID NO:35, and a Vβ domain having at least 90% sequence identity to SEQ ID NO:11, wherein the CDR3 region has at least 90% sequence identity to SEQ ID NO:37.

One embodiment provides an engineered murine T cell receptor (mTCR) having a Vα domain having at least 90% sequence identity to SEQ ID NO:10, wherein the CDR3 region has at least 90% sequence identity to SEQ ID NO:36, and a Vβ domain having at least 90% sequence identity to SEQ ID NO:11, wherein the CDR3 region has at least 90% sequence identity to SEQ ID NO:37. Any of the disclosed mTCRs can be humanized.

One embodiment provides a T cell engineered to express any of the disclosed mTCRs. The T cell can be human. The T cell can also be an autologous T cell.

Another embodiment provides a soluble mTCR α chain comprising Q21 to L242 of SEQ ID NO:2, 3, 4, 5, 6, 7, 8, 9, 10, 15, 16, 17, 18, 19, 20, 21, 22, or 23.

Another embodiment provides the extracellular domain of an engineered mTCR β chain containing SEQ ID NO:50, 51, 52, or 53, or E18 to Y276 of SEQ ID NO:24, 25, 26, or 27.

One embodiment provides a fusion protein having at least 90% sequence identity to SEQ ID NO:54, 55, 56, 57, 58, 59, 60, 61, or 62.

Another embodiment provides a vector encoding any one of the mTCR proteins or polypeptides.

Another embodiment provides a nucleic acid having at least 90% sequence identity to SEQ ID NO:63, 64, 65, 66, 67, 68, 69, 70, or 71.

Another embodiment provides a non-naturally occurring hAFP$_{158}$ epitope-specific murine T cell receptor including:
a). an α chain variable domain (Vα) having at least 90% sequence identity to amino acid residues 21-132 of SEQ ID NO:2, 3, 4, 5, 6, 7, 8, 9, or 10; and
b). a β chain variable domain (Vβ) having at least 90% sequence identity to amino acid residues 18-131 of SEQ ID NO:11, 12, 13, or 14.

Another embodiment provides a fusion protein including a first polypeptide having at least 90% sequence identity to an amino acid sequence according to SEQ ID NO:2, 3, 4, 5, 6, 7, 8, 9, or 10, linked to a second polypeptide having at least 90% sequence identity to an amino acid sequence according to SEQ ID NO:11, 12, 13, or 14.

Another embodiment provides a fusion protein including a first polypeptide having at least 90% sequence identity to an amino acid sequence according to SEQ ID NO:15, 16, 17, 18, 19, 20, 21, 22, or 23, linked to a second polypeptide having at least 90% sequence identity to an amino acid sequence according to SEQ ID NO:24, 25, 26, or 27.

Another embodiment provides a T cell engineered to express the TCR encoded by SEQ ID NO: 63, 64, 65, 66, 67, 68, 69, 70, or 71. The T cell can be human.

Another embodiment provides a hybridoma having a CD8+Tet$_{158+}$ cell fused to a donor cell lacking TCR α and β chains. The hybridoma typically responds to hAFP+ tumor cells. In certain embodiments, the hybridoma secretes IL-2.

Another embodiment provides a fusion protein having a first polypeptide having at least 90% sequence identity to an amino acid sequence according to SEQ ID NO:2, 3, 4, 5, 6, 7, 8, 9, or 10 linked to a second polypeptide having at least 90% sequence identity to an amino acid sequence according to SEQ ID NO:11, 12, 13, 14, 24, 25, 26, or 27, wherein in the fusion protein is linked to a single chain anti-CD3 antibody.

Another embodiment provides a method for treating tumors in a subject in need thereof by genetically engineering human T cells to express a disclosed mTCR and administering the engineered T cells to the subject in an amount effective to reduce tumor burden in the subject. In certain embodiments the tumors are hepatocellular carcinoma. The T cells can be autologous T cells.

Another embodiment provides a method for detecting heptacellular carcinoma by contacting a disclosed polypeptide or protein to a sample of cells, wherein specific binding of the polypeptide or protein to a cell is indicative of a heptacellular carcinoma cell.

Another embodiment provides an antibody or antigen binding fragment there of that specifically bindes to a disclosed polypeptide or protein.

BRIEF DESCRIPTION OF THE DRAWINGS

FIGS. 1A-1D are dot plots of mouse peripheral blood cells stimulated with hAFP158 peptide to analyze for CD8 and IFN-γ by gating on the Thy1.2+ T cells. FIG. 1E is a graph of % of CD8+IFNg+ of total spleen cells with or without lv prime. FIGS. 1F-1H are dot plots of splenic T cells stimulated with HepG2(AFP−)(FIG. 1F), HepG2(AFP+)(FIG. 1G) and hAFP158 peptide (FIG. 1H). FIG. 1I is a graph of % of CD8+IFNg+ of total spleen cells stimulated with HepG2(AFP−), HepG2(AFP+) and hAFP158 peptide. FIGS. 1J-1L are photomicrographs of HepG2 cells co-cultured with splenocytes. FIG. 1M is a graph of Remaining alive HepGe cells (OD595) versus E/T ratio, (●) is Lv+Pep and (■) is Pep+Pep.

FIGS. 2A-2E show the adoptive transfer of immunized AAD mouse splenocytes prevents mice from tumor challenge and eradicates HepG2 tumor xenografts in NSG mice. FIG. 2A is a dot plot showing approximately 10% of the immunized mouse splenocytes produced IFNg in response to hAFP158 peptide. FIG. 2B illustrates fifteen million total splenocytes (1.5 million of hAFP158-specific CD8 T cells) of naïve or immunized mice were injected into NSG mice, which were then challenged with HepG2 tumor cells. FIG. 2C is a diagram representing NSG mice injected with 1.5 million splenocytes of the immunized mice when tumor size reaches 2 cm in diameter. FIG. 2D is a line graph of tumor size (mm$^3$) versus days after tumor inoculation in control (●) and ACT (■). FIG. 2E is a line graph of Tumor Volume (mm$^3$) versus days after tumor innoculation in mouse 1 (●), mouse 2 (■), mouse 3 (▲), and mouse 4 (▼).

FIG. 3A is a dot plot showing the purity of hAFP158 specific CD8 T cells. FIG. 3B is a dot plot showing the percent of hAFP158 specific IFNγ-producing cells. FIG. 3C is a dot plot showing the purity of Flu M1 specific CD8 T cells. FIG. 3D is a dot plot showing percent of Flu M1 specific IFNγ-producing cells. FIG. 3E is a line graph of Tumor Volume (mm$^3$) versus days after tumor inoculation for mice treated with CD8 of Lv+hAFP158 (e) or CD8 of Flu+M1. FIGS. 3F to 3H are dot plots of purified CD8 T cells from hAFP immunized mice further separated into Tet158+ and Tet158− cells by Tet158 tetramer staining and cell sorter. The purity before and after sorting is presented. FIG. 3I is a line graph of tumor volume (mm$^3$) versus days after tumor inoculation for mice treated with Tet158+ (●) or Tet158− (■) cells.

FIGS. 3J-3O are images of the mice from FIG. 3I. FIGS. 4B to 4G are histograms of the hybridoma clones were stained with anti-Vβ8.3 antibody. FIGS. 4H to 4M are histograms of the hybridoma clones were stained with Tet158 tetramer.

FIGS. 5B to 5E are histograms Tet158 tetramer staining of the human T cell line Jurkat cells after transduction with three different TCR-lv. Histogram and MFI were presented. FIGS. 5G to 5J, 5L to 5O, and 5Q to 5T are dot plots of primary human T cells from 3 different donors transduced with TCR-lvs showng the percent and MFI of Tet158+ CD8 and CD4 T cells. Mock transduced cells had undergone same CD3/CD28 treatment without lv transduction or with GFP-lv transduction. FIGS. 5F, 5K, 5P, and 5U are bar graphs showing MFI of Tet158 on transduced T cells from three different donors. TCR-T cells are shown. Only the CD8 or CD4 T cells were gated and shown in the representative plots.

FIGS. 6B to 6E are dot plots showing intracellular staining of IFNγ and IL-2 by CD8. FIGS. 6F to 6I are dot plots showing intracellular staining of IFNγ and IL-2 by CD4. FIGS. 6J to 6O are dot plots and histograms showing the induction of CD8 and CD4 TCR-T cell proliferation by hAFP+HepG2 tumor cells was shown. The experiment was repeated twice with similar data.

FIG. 7A is a bar graph of percent killing by HLA-A2+ human primary T cells transduced with TCR genes and treated with AFP-HepG2 (hatched bars), Huh7 (black bars), or AFP+HepG2 (white bars). FIG. 7B is a line graph of percent killing versus E:T ratios for TCR (●) and Mock (■). FIGS. 7C, 7D, and 7E are dot plots showing donor CD8 and CD4 TCR-T cells separated by magnetic beads after TCR gene transduction. FIGS. 7F to 7K are photomicrographs of the co-culture of the mock-transduced, CD4, or CD8 TCR-T cells with HepG2 tumor cells. Photographs were taken at 2 hours and 24 hours after co-culture. FIG. 7L is a bar graph showing the results of an LDH assay to measure percents killing in CD4 cells (black bar), CD8 cells (white bar), and total T cells (hatched bar) in TCR or mock transduced human T cells. FIG. 7M to 7O are photomicrographs of representative cells from FIG. 1.

FIG. 11A is a dot plot showing the percent of Tet158+ CD8+ splenocytes from immunized mice. FIGS. 11B-11P are histograms showing Vbeta expression in CD8+, Tet158+ cells using different anti-Vbeta chain antibodies.

FIG. 12A-D show the transduction of primary human T-cells with recombinant lv.

FIG. 12A is an illustration of the GFP-lv promoter. FIGS. 12B and 12C are representative images of GFP expressing primary T-cells. FIG. 12D is a histogram of GFP+ T cells.

FIG. 13A is a histogram showing the percent of TCR-T cells stained with anti-Vbeta chain antibody. FIG. 13B is a histogram showing the percent of TCR-T cells stained with Tet158 tetramer.

FIGS. 14A-14I show that human TCR-T cells specifically recognize AFP158 peptide pulsed HLA-A2 mouse splenocytes. FIG. 14A is a bar graph showing IFN-g production (pg/ml) in mock T-cells, TCR1 T-cells, TCR2, T-cells, or TCR3 T-cells, stimulated with AAD mouse splenocytes and pulsed with no peptide (hatched bar), influenza M1 peptide (black bar), or AFP158 peptide (white bar). FIG. 14B-14E are histograms showing percent of IFNg staining human T-cells (containing both CD4 and CD8) stimulated with hAFP158 peptide pulsed HLA-A2 cells. FIG. 14F-14I are histograms showing percent of IL-2 staining human T-cells (containing both CD4 and CD8) stimulated with hAFP158 peptide pulsed HLA-A2 cells.

FIGS. 15A-15T show that the adoptive transfer of human TCR-T generates antitumor effect against HepG2 tumor in NSG mice. FIG. 15A is a dot plot showing the % Tet158+ cells out of total human TCR-T cells. FIG. 15B is a line graph representing tumor outgrowth (% tumor free mice) versus days after tumor inoculation in control and TCR-T groups. FIG. 15C is a line graph representing tumor size (mm³) versus days after tumor inoculation in control (●) and TCR-T (■). FIG. 15D-15K are pictures of HepG2 tumors at day 31 after the inoculation in Mock-T treated (FIGS. 15D-15G) and TCR-T treated (FIGS. 15H-15K) mice. FIG. 15L-15O are representative dot plots showing the percent of human CD45+ cells among total mouse blood cells. FIG. 15P is a line graph representing the percent human CD45+ cells among total mouse blood cells for control (●) and TCR-T (■). FIG. 15Q-15R is representative dot plots showing the percentage of Tet158+ cells out of the transferred human T cells in the NSG mice. FIG. 15S is a line graph representing the percent Tet158+ cells out of the total transferred human T cells versus days after ACT. FIG. 15T is a line graph representing the percent of Tet158+ cells out of the total transferred CD8 (●) and CD4 (■) T cells versus days after ACT.

FIG. 16 is a schematic comparison of the V-region of the 9 mTCR sequences.

FIG. 17 is a schematic comparison of the amino acid sequences of CDR3 of the 9 mTCR α chains (FIG. 17A) and β chains (FIG. 17B).

DETAILED DESCRIPTION OF THE INVENTION

I. Definitions

Figure 4A:
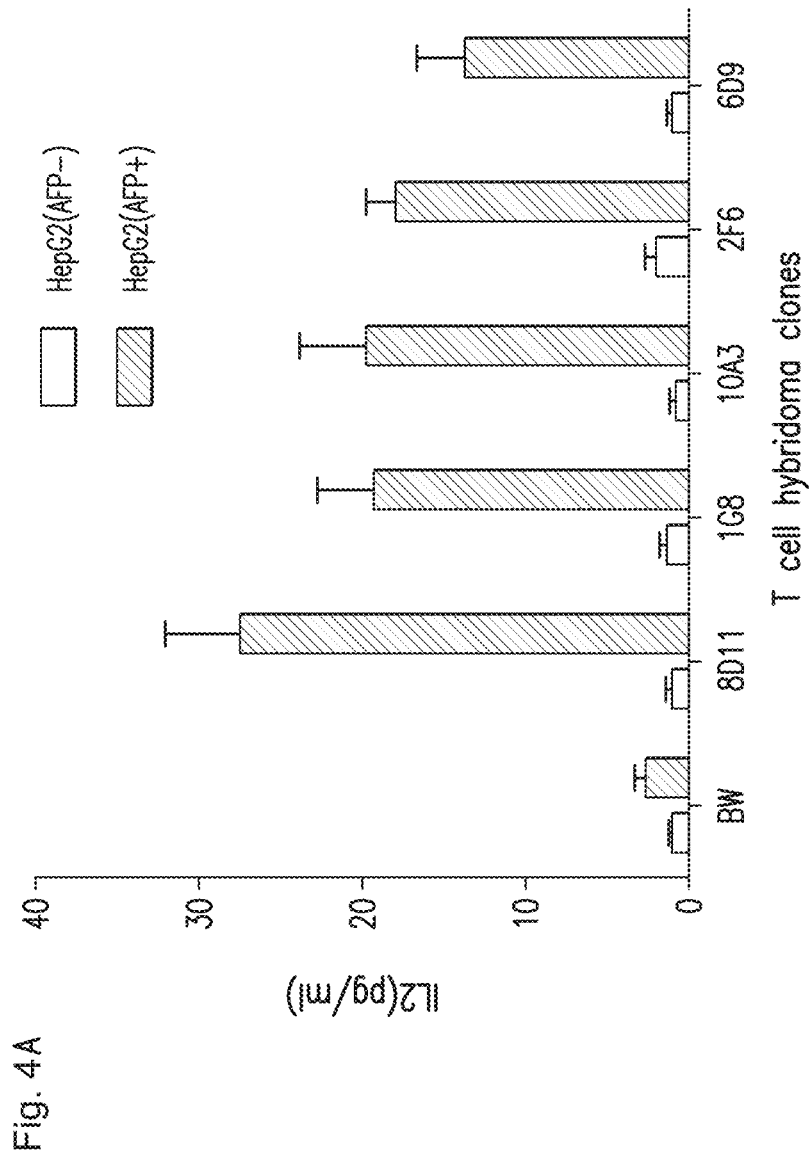
FIG. 4A is a bar graph of IL-2 (pg/ml) from T cell hybridoma clones. BW-Lyt2.4 fusion partner cells and 5 different hybridoma clones were co-cultured in triplicate with hAFP+ (hatched bars) or hAFP− (white bars) HepG2 tumor cells and the IL-2 production was detected by ELISA.

The phrase "having antigenic specificity" as used herein means that the TCR can specifically bind to and immunologically recognize the cancer antigen, such that binding of the TCR to the cancer antigen elicits an immune response.

The term "$Tet_{158}$" refers to HLA-A2/hAFP158 tetramers.

The term "$hAFP_{158}$" refers to human alpha fetoprotein polypeptide having the amino acid sequence of FMNKFI-YEI (SEQ ID NO:1).

The initialism "TCR" refers to a T cell receptor which is a specific receptor on the surface of T cells that is responsible for identifying the antigen presented by the major histocompatibility complex (MHC).

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g. signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, preferably about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

As used herein, the term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, an "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within +2 is preferred, those within +1 are particularly preferred, and those within +0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotide or amino acid sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents. As used herein, the terms "antigenic determinant" and "epitope" are used interchangeably and refer to the structure recognized by an antibody.

As used herein, a "conformational epitope" is an epitope that includes discontinuous sections of the antigen's amino acid sequence. Antibodies bind a conformational epitope based on 3-D surface features, shape, or tertiary structure of the antigen.

As used herein, a "linear epitope" is an epitope that formed by a continuous sequence of amino acids from the antigen. Linear epitopes typically include about 5 to about 10 continuous amino acid residues. Antibodies bind a linear epitope based on the primary sequence of the antigen.

As used herein, a "paratope," also called an "antigen-binding site," is a part of an antibody which recognizes and binds to an antigen.

As used herein, "adoptive cell transfer" or ACT is a type of immunotherapy in which a patient's own T cells are collected, expanded ex vivo, and re-infused into the patient. Two types of ACT are chimeric antigen receptor (CAR) and T cell receptor (TCR) T cell therapy. Both techniques improve the ability of T cell receptors to recognize and attack specific antigens. In CAR T-cell therapy, T cells are engineered to produce receptors on their surface called chimeric antigen receptors. The receptors allow the T cells to recognize and attach to antigens on tumor cells. In TCR-T cell therapy, T cells are collected from a patient, modified to express a TCR specific to a tumor antigen, expanded ex vivo, and re-infused into the patient.

II. T Cell Receptor Compositions

T cell receptor genes are provided that encode a receptor that specifically binds to hAFP, preferably to $hAFP_{158}$ that is expressed on the surface of cancer cells. Nine pairs of murine TCR α and β chain genes specific for the HLA-A2/$hAFP_{158}$ were identified and synthesized. The amino acid and nucleic acid sequences for the TCR genes are provided below. Vectors that contain one or more of the TCR genes are also provided.

Another embodiment provides $hAFP_{158}$-specific ($Tet_{158}$) mouse CD8 T cells that recognize and kill human HepG2 cells in vitro and eradicate large HepG2 tumor xenografts in NSG mice.

Still another embodiment provides T cell hybridomas made from the $Tet_{158}$ CD8 T cells. The T cell hybridomas enabled the identification of paired TCR α and β chain genes. One embodiment provides healthy donor CD8 T cells transduced with the murine TCR α and β chain genes specific for the HLA-A2/$hAFP_{158}$. The genetically engineered TCR enables the donor cells to recognize and effectively kill HepG2 tumor cells at very low E/T ratio. These murine TCR genes specific for the HLA-A2/$hAFP_{158}$ have the potential to modify and redirect the patient's autologous T cells to treat HCC tumors via adoptive cell transfer.

Another embodiment provides soluble T cell receptors. In one embodiment the soluble TCR includes the extracellular domain of the TCR polypeptides.

A. Genetically Engineered T Cell Receptors

The disclosed TCR genes are from the recombinant lv-primed and peptide-boosted AAD mice. Thus, technically, these TCRs are not "naturally occurring". In addition, after obtaining the Vα and Vβ region of TCRs, full length α and β chains were designed by using the identified V-region of α and β chains, and the constant region (C-region) of α and β chains of HLA-A2 mouse TCR specific for hgp100. Thus, the entire TCRs and their genes are not naturally occurring.

1. Protein Sequences of the mTCR-1, 2, 3, 6, 8, 10, 11, 17 and 38 Vα Domain

One embodiment provides mTCR-1 Vα (TRAV7D-2*01/TRAJ30*01) having at least 90%, 95%, 99 or 100% sequence identity to (SEQ ID NO:2):

```
  1 MKSFSISLVV LWLQLNWVNS QQKVQQSPES LIVPEGGMAS LNCTSSDRNV

51 DYFWWYRQHS GKSPKMLMSI FSNGEKEEGR FTVHLNKASL HTSLHIRDSQ

101 PSDSALYLCA ASITNAYKVI FGKGTHLHVL PN
```

Another embodiment provides mTCR-2 Vα (TRAV7D-2*01/TRAJ30*01) having at 90%, 95%, 99 or 100% sequence identity to (SEQ ID NO:3):

```
  1 MKSFSISLVV LWLQLNWVNS QQKVQQSPES LIVPEGGMAS LNCTSSDRNV

51 DYFWWYRQHS GKSPKMLMSI FSNGEKEEGR FTVHLNKASL HTSLHIRDSQ

101 PSDSALYLCA ASTVNAYKVI FGKGTHLHVL PN
```

Comparing mTCR-1 α chain V-region to mTCR-2 α chain, there is only 2 amino acids difference (bolded and underlined).

Another embodiment provides mTCR-3 Vα (TRAV7D-2*01/TRAJ12*01) having at least 90%, 95%, 99 or 100% sequence identity to (SEQ ID NO:4):

```
  1 MKSFSISLVV LWLQLNWVNS QQKVQQSPES LIVPEGGMAS LNCTSSDRNV

51 DYFWWYRQHS GKSPKMLMSI FSNGEKEEGR FTVHLNKASL HTSLHIRDSQ

101 PSDSALYLCA ASMAGGYKVV FGSGTRLLVS PD
```

There are multiple amino acid differences between mTCR-1 α chain and mTCR-3 α chain (bolded and underlined). In fact, the J segment is different (Instead of TRAJ30, the TRAJ12 is used in mTCR-3 Vα).

One embodiment provides mTCR-6 Vα (TRAV7D-2*01/TRAJ30*01) having at least 90%, 95%, 99 or 100% sequence identity to (SEQ ID NO:5):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ASMINAYKVI FGKGTHLHVL PN
```

Another embodiment provides mTCR-8 Vα (TRAV7D-2*01/TRAJ12*01) having at 90%, 95%, 99 or 100% sequence identity to (SEQ ID NO:6):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ASISGGYKVV FGSGTRLLVS PD
```

There are multiple amino acid differences between mTCR-6 α chain and mTCR-8 α chain (bolded and underlined). In fact, the J segment is different (Instead of TRAJ30, the TRAJ12 is used in mTCR-8 Vα).

Another embodiment provides mTCR-10 Vα (TRAV7D-2*01/TRAJ12*01) having at least 90%, 95%, 99 or 100% sequence identity to (SEQ ID NO:7):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ASIVGGYKVV FGSGTRLLVS PD
```

Comparing mTCR-6 α chain V-region to mTCR-8 α chain, there is only 1 amino acids difference (bolded and underlined).

Another embodiment provides mTCR-11 Vα (TRAV7D-2*01/TRAJ12*01) having at least 90%, 95%, 99 or 100% sequence identity to (SEQ ID NO:8):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ASKTGGYKVV FGSGTRLLVS PD
```

Comparing mTCR-6 α chain V-region to mTCR-8 α chain, there are only 2 amino acid differences (bolded and underlined).

One embodiment provides mTCR-17 Vα (TRAV7D-2*01/TRAJ12*01) having at least 90%, 95%, 99 or 100% sequence identity to (SEQ ID NO:9):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ASMTGGYKVV FGSGTRLLVS PD
```

Another embodiment provides mTCR-38 Vα (TRAV7D-2*01/TRAJ12*01) having at least 90%, 95%, 99 or 100% sequence identity to (SEQ ID NO:10):

```
  1 MKSFSISLVV LWLQLNWVNS QQKVQQSPES LIVPEGGMAS LNCTSSDRNV
 51 DYFWWYRQHS GKSPKMLMSI FSNGEKEEGR FTVHLNKASL HTSLHIRDSQ
101 PSDSALYLCA ATLTGGYKVV FGSGTRLLVS PD
```

In certain embodiments, the leading methionine and/or signal sequence is cleaved in the post-translationally modified protein.

2. Protein Sequences of the mTCR-1, 2, 3, 6, 8, 10, 11, 17 and 38 Vβ Domains

One embodiment provides mTCR-1, 2, 8, 11, 17 & 38 Vβ domain (TRBV13-1*01/TRBJ2-4*01) having 90%, 95%, 99%, or 100% sequence identity to (SEQ ID No:11):

```
  1 MGSRLFLVLS LLCTKHMEAA VTQSPRNKVT VTGGNVTLSC RQTNSHNYMY
 51 WYRQDTGHGL RLIHYSYGAG NLQIGDVPDG YKATRTTQED FFLLLELASP
101 SQTSLYFCAS SDAGTSQNTL YFGAGTRLSV L
```

Another embodiment provides mTCR-3 Vβ domain (TRBV13-1*01/TRBJ2-4*01) having 90%, 95%, 99%, or 100% sequence identity to (SEQ ID NO:12):

```
  1 MGSRLFLVLS LLCTKHMEAA VTQSPRNKVT VTGGNVTLSC RQTNSHNYMY
 51 WYRQDTGHGL RLIHYSYGAG NLQIGDVPDG YKATRTTQED FFLLLELASP
101 SQTSLYFCAS SDAGTAQNTL YFGAGTRLSV L
```

There is only one amino acid difference (bold and underlined) between mTCR-1 and mTCR-2 with TCR-3 Vβ.

Another embodiment provides mTCR-6 Vβ domain (TRBV13-1*01/TRBJ2-4*01) having 90%, 95%, 99%, or 100% sequence identity to (SEQ ID NO:13):

```
  1    MGSRLFLVLS LLCTKHMEAA VTQSPRNKVT VTGGNVTLSC RQTNSHNYMY
 51    WYRQDTGHGL RLIHYSYGAG NLQIGDVPDG YKATRTTQED FFLLLELASP
101    SQTSLYFCAS SDAGVSQNTL YFGAGTRLSV L
```

There is only one amino acid difference from mTCR-1, 2, 8, and 11, a 2 amino acid difference from mTCR-3, and a 3 amino acid difference from mTCR-10.

Another embodiment provides mTCR-10 Vβ domain (TRBV13-1*01/TRBJ2-4*01) having 90%, 95%, 99%, or 100% sequence identity to (SEQ ID NO:14):

```
  1    MGSRLFLVLS LLCTKHMEAA VTQSPRNKVT VTGGNVTLSC RQTNSHNYMY
 51    WYRQDTGHGL RLIHYSYGAG NLQIGDVPDG YKATRTTQED FFLLLELASP
101    SQTSLYFCAS SDHGTGQNTL YFGAGTRLSV L
```

There are 3 amino acid differences (bold and underlined) between mTCR-6 Vβ with TCR-10 βVθ.

In certain embodiments, the leading methionine and/or signal sequence is cleaved in the post-translationally modified protein.

3. Protein sequences of the full length mTCR-1, 2, 3, 6, 8, 10, 11, 17 and 38 α chains Another embodiment provides mTCR-1 α chain (TRAV7D-2*01/TRAJ30*01/TRAC) having 90%, 95%, 99%, or 100% sequence identity to (SEQ ID NO:15):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASITNAYKVI FGKGTHLHVL PNIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

The constant region (Cα) (bolded) of mTCR-1, 2, 3, 6, 8, 10, and 11 α chains are the same, and they are identical to the hgp100 specific TCR α chain C-region from HLA-A2 Tg mice.

Another embodiment provides mTCR-2 α chain (TRAV7D-2*01/TRAJ30*01/TRAC) having 90%, 95%, 99%, or 100% sequence identity to (SEQ ID NO:16):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASTVNAYKVI FGKGTHLHVL PNIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-3 α chain (TRAV7D-2*01/TRAJ12*01/TRAC) having 90%, 95%, 99%, or 100% sequence identity to (SEQ ID NO:17):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASMAGGYKVV FGSGTRLLVS PDIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-6 α chain (TRAV7D-2*01/TRAJ30*01/TRAC) having 90%, 95%, 99%, or 100% sequence identity to (SEQ ID NO:18):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASMINAYKVI FGKGTHLHVL PNIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-8 α chain (TRAV7D-2*01/TRAJ12*01/TRAC) having 90%, 95%, 99%, or 100% sequence identity to (SEQ ID NO:19):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASISGGYKVV FGSGTRLLVS PDIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-10 α chain (TRAV7D-2*01/TRAJ12*01/TRAC) having 90%, 95%, 99%, or 100% sequence identity to (SEQ ID NO:20):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASIVGGYKVV FGSGTRLLVS PDIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-11 α chain (TRAV7D-2*01/TRAJ12*01/TRAC) having 90%, 95%, 99%, or 100% sequence identity to (SEQ ID NO:21):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASKTGGYKVV FGSGTRLLVS PDIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

One embodiment provides mTCR-17 α chain (TRAV7D-2*01/TRAJ12*01/TRAC) having 90%, 95%, 99%, or 100% sequence identity to (SEQ ID NO:22):

```
  1    MKSFSISLVV LWLQLNWVNS QQKVQQSPES LIVPEGGMAS LNCTSSDRNV
 51    DYFWWYRQHS GKSPKMLMSI FSNGEKEEGR FTVHLNKASL HTSLHIRDSQ
101    PSDSALYLCA ASMTGGYKVV FGSGTRLLVS PDIQNPEPAV YQLKDPRSQD
151    STLCLFTDFD SQINVPKTME SGTFITDKTV LDMKAMDSKS NGAIAWSNQT
201    SFTCQDIFKE TNATYPSSDV PCDATLTEKS FETDMNLNFQ NLSVMGLRIL
251    LLKVAGFNLL MTLRLWSS
```

Another embodiment provides mTCR-38 α chain (TRAV7D-2*01/TRAJ12*01/TRAC) having 90%, 95%, 99%, or 100% sequence identity to (SEQ ID NO:23):

```
  1  MKSFSISLVV LWLQLNWVNS QQKVQQSPES LIVPEGGMAS LNCTSSDRNV
 51  DYFWWYRQHS GKSPKMLMSI FSNGEKEEGR FTVHLNKASL HTSLHIRDSQ
101  PSDSALYLCA ATLTGGYKVV FGSGTRLLVS PDIQNPEPAV YQLKDPRSQD
151  STLCLFTDFD SQINVPKTME SGTFITDKTV LDMKAMDSKS NGAIAWSNQT
201  SFTCQDIFKE TNATYPSSDV PCDATLTEKS FETDMNLNFQ NLSVMGLRIL
251  LLKVAGFNLL MTLRLWSS
```

In certain embodiments, the leading methionine and/or signal sequence is cleaved in the post-translationally modified protein.

In one embodiment, based on the nomenclature on IMGT and Uniprot website, the mTCR α chain features are believed to be as follows:

1. M1-S20: Leader Sequences to be removed on maturation of TCR α chain
2. Q21-S268: TCR-1, 2, 3 α chain
3. Q21-N132 (or D132): α chain V-region
4. I133-S268: TCR α chain C-region identical to the HLA-A2 mouse TCR specific for hgp100 (DQ452619)
5. Q21-L242: TCR α chain extracellular domain
6. S243-L263: transmembrane region of mature TCR α chain
7. R264-S268: intracellular region of mature TCR α chain 4. Protein Sequences of Full Length mTCR-1, 2, 3, 6, 8, 10, 11, 17, and 38 β Chains Another embodiment provides mTCR-1, 2, 8, 11, 17, and 38 β chain (TRBV13-1*01/TRBJ2-4*01/TRBC1) having 90%, 95%, 99%, or 100% sequence identity to (SEQ ID NO:24):

```
  1  MGSRLFLVLS LLCTKHMEAA VTQSPRNKVT VTGGNVTLSC RQTNSHNYMY
 51  WYRQDTGHGL RLIHYSYGAG NLQIGDVPDG YKATRTTQED FFLLLELASP
101  SQTSLYFCAS SDAGTSQNTL YFGAGTRLSV LEDLRNVTPP KVSLFEPSKA
151  EIANKRKATL VCLARGFFPD HVELSWWVNG KEVHSGVSTD PQAYKESNYS
201  YCLSSRLRVS ATFWHNPRNH FRCQVQFHGL SEEDKWPEGS PKPVTQNISA
251  EAWGRADCGI TSASYQQGVL SATILYEILL GKATLYAVLV STLVVMAMVK
301  RKNS
```

The constant region (Cβ) (bolded) of mTCR-1, 2, 3, 6, 8, 10, 11, 17, and 38β chains are the same, and they are identical to the hgp100 specific TCR β chain C-region from HLA-A2 Tg mice.

In certain embodiments, the leading methionine and/or signal sequence is cleaved in the post-translationally modified protein.

Another embodiment provides mTCR-3 β chain (TRBV13-1*01/TRBJ2-4*01/TRBC1) having 90%, 95%, 99%, or 100% sequence identity to (SEQ ID NO:25)

```
  1  MGSRLFLVLS LLCTKHMEAA VTQSPRNKVT VTGGNVTLSC RQTNSHNYMY
 51  WYRQDTGHGL RLIHYSYGAG NLQIGDVPDG YKATRTTQED FFLLLELASP
101  SQTSLYFCAS SDAGTAQNTL YFGAGTRLSV LEDLRNVTPP KVSLFEPSKA
151  EIANKRKATL VCLARGFFPD HVELSWWVNG KEVHSGVSTD PQAYKESNYS
201  YCLSSRLRVS ATFWHNPRNH FRCQVQFHGL SEEDKWPEGS PKPVTQNISA
251  EAWGRADCGI TSASYQQGVL SATILYEILL GKATLYAVLV STLVVMAMVK
301  RKNS
```

Another embodiment provides mTCR-6 β chain (TRBV13-1*01/TRBJ2-4*01/TRBC1) having 90%, 95%, 99%, or 100% sequence identity to (SEQ ID NO:26)

```
  1  MGSRLFLVLS LLCTKHMEAA VTQSPRNKVT VTGGNVTLSC RQTNSHNYMY
 51  WYRQDTGHGL RLIHYSYGAG NLQIGDVPDG YKATRTTQED FFLLLELASP
101  SQTSLYFCAS CDAGVSQNTL YFGAGTRLSV LEDLRNVTPP KVSLFEPSKA
151  EIANKRKATL VCLARGFFPD HVELSWWVNG KEVHSGVSTD PQAYKESNYS
201  YCLSSRLRVS ATFWHNPRNH FRCQVQFHGL SEEDKWPEGS PKPVTQNISA
251  EAWGRADCGI TSASYQQGVL SATILYEILL GKATLYAVLV STLVVMAMVK
301  RKNS
```

Another embodiment provides mTCR-10 β chain (TRBV13-1*01/TRBJ2-4*01/TRBC1) having 90%, 95%, 99%, or 100% sequence identity to (SEQ ID NO:27)

```
  1  MGSRLFLVLS LLCTKHMEAA VTQSPRNKVT VTGGNVTLSC RQTNSHNYMY
 51  WYRQDTGHGL RLIHYSYGAG NLQIGDVPDG YKATRTTQED FFLLLELASP
101  SQTSLYFCAS SDHGTGQNTL YFGAGTRLSV LEDLRNVTPP KVSLFEPSKA
151  EIANKRKATL VCLARGFFPD HVELSWWVNG KEVHSGVSTD PQAYKESNYS
201  YCLSSRLRVS ATFWHNPRNH FRCQVQFHGL SEEDKWPEGS PKPVTQNISA
251  EAWGRADCGI TSASYQQGVL SATILYEILL GKATLYAVLV STLVVMAMVK
301  RKNS
```

In certain embodiments, the leading methionine and/or signal sequence is cleaved in the post-translationally modified protein.

In one embodiment, based on the nomenclature on IMGT and Uniprot website, the mTCR α chain features are as follows:
1. M1-M17: Leader Sequences to be removed on maturation of mTCR β chain
2. E18-S304: mTCR β chain
3. E18-L131: mTCR β chain V-region (TRBV13-1*01/TRBJ2-4*01 with S113 (TCR-1&2) or A113 (TCR-3)-A116 as the D region)
4. E132-S304: mTCR β chain Cl-region of HLA-A mTCR specific for hgp100 (DQ452620)
5. E18-Y276: mTCR β chain extracellular domain
6. E277-M298: transmembrane region of mature mTCR β chain
7. V299-S304: intracellular (topological) region of mature mTCR β chain 5. Protein Sequences of CDR3 Region of mTCR-1, 2, 3, 6, 8, 10, 11, 17, and 38 α Chains One embodiment provides mTCR-1 α chain CDR3 region having 90%, 95%, 99%, or 100% sequence identity to (SEQ ID NO:28):

AASITNAYKVIFGKGTHLHVLPNIQNPE

Another embodiment provides mTCR-2 α chain CDR3 region having 90%, 95%, 99%, or 100% sequence identity to (SEQ ID NO:29):

AASTVNAYKVIFGKGTHLHVLPNIQNPE

One embodiment provides mTCR-3 α chain CDR3 region having 90%, 95%, 99%, or 100% sequence identity to (SEQ ID NO:30):

AASMAGGYKVVFGSGTRLLVSPDIQNPE

One embodiment provides mTCR-6 α chain CDR3 region having 90%, 95%, 99%, or 100% sequence identity to (SEQ ID NO:31):

AASMINAYKVIFGKGTHLHVLPNIQNPE

Another embodiment provides mTCR-8 α chain CDR3 region having 90%, 95%, 99%, or 100% sequence identity to (SEQ ID NO:32):

AASISGGYKVVFGSGTRLLVSPDIQNPE

One embodiment provides mTCR-10 α chain CDR3 region having 90%, 95%, 99%, or 100% sequence identity to (SEQ ID NO:33):

AASIVGGYKVVFGSGTRLLVSPDIQNPE

One embodiment provides mTCR-11 α chain CDR3 region having 90%, 95%, 99%, or 100% sequence identity to (SEQ ID NO:34):

AASKTGGYKVVFGSGTRLLVSPDIQNPE

Another embodiment provides mTCR-17 α chain CDR3 region having 90%, 95%, 99%, or 100% sequence identity to (SEQ ID NO:35):

AASMTGGYKVVFGSGTRLLVSPDIQNPE

One embodiment provides mTCR-38 α chain CDR3 region having 90%, 95%, 99%, or 100% sequence identity to (SEQ ID NO:36):

AATLTGGYKVVFGSGTRLLVSPDIQNPE

6. Protein Sequences of CDR3 Region of mTCR-1, 3, 6, and 10 β Chains

One embodiment provides mTCR-10 chain CDR3 region having 90%, 95%, 99%, or 100% sequence identity to (SEQ ID NO:37):

ASSDAGTSQNTLYFGAGTRLSVL

One embodiment provides mTCR-3 β chain CDR3 region having 90%, 95%, 99%, or 100% sequence identity to (SEQ ID NO:38):

ASSDAGTAQNTLYFGAGTRLSVL

Another embodiment provides mTCR-6 β chain CDR3 region having 90%, 95%, 99%, or 100% sequence identity to (SEQ ID NO:39):

ASSDAGVSQNTLYFGAGTRLSVL

One embodiment provides mTCR-10 β chain CDR3 region having 90%, 95%, 99%, or 100% sequence identity to (SEQ ID NO:40):

ASSDHGTGQNTLYFGAGTRLSVL

7. The Extracellular Domain of mTCR-1, 2, 3, 6, 8, 10, 11, 17 and 38 α Chains (for Soluble TCRs) (Underlined are the Vα)

The extracellular domain of TCR α and β chains can form soluble TCRs. If they are labeled with detectable labels, for example fluorescent molecules, they can be used to detect the HLA-A2/hAFP$_{158}$ complex presented on tumor cells. The labeled soluble TCRs have the potential of as diagnosis reagents for detecting circulating tumor cells in the blood and to determine the cognate antigen epitope presentation in tumor tissues, which is important for the success of using such TCR-T cells in the setting of adoptive cell transfer therapy.

One embodiment provides the soluble mTCR-1 α chain (Q21-L242) having at least 90%, 95%, 99%, or 100% sequence identity to (SEQ ID NO:41):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASITNAYKVI FGKGTHLHVL

PNIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-2 α chain (Q21-L242) having at least 90%, 95%, 99%, 100% to (SEQ ID NO:42):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASTVNAYKVI FGKGTHLHVL

PNIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-3 α chain (Q21-L242) having 90%, 95%, 99%, or 100% sequence identity to (SEQ ID NO:43):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASMAGGYKVV FGSGTRLLVS

PDIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-6 α chain (Q21-L242) having 90%, 95%, 99%, or 100% sequence identity to (SEQ ID NO:44):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASMINAYKVI FGKGTHLHVL

PNIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-8 α chain (Q21-L242) having 90%, 95%, 99%, or 100% sequence identity to (SEQ ID NO:45):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASISGGYKVV FGSGTRLLVS

PDIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-10 α chain (Q21-L242) having 90%, 95%, 99%, or 100% sequence identity to (SEQ ID NO:46):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASIVGGYKVV FGSGTRLLVS

PDIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

Another embodiment provides soluble mTCR-11 α chain (Q21-L242) having 90%, 95%, 99%, or 100% sequence identity to (SEQ ID NO:47):

QQKVQQSPES LIVPEGGMAS LNCTSSDRNV DYFWWYRQHS

GKSPKMLMSI FSNGEKEEGR FTVHLNKASL

HTSLHIRDSQ PSDSALYLCA ASKTGGYKVV FGSGTRLLVS

PDIQNPEPAV YQLKDPRSQD STLCLFTDFD

SQINVPKTME SGTFITDKTV LDMKAMDSKS NGAIAWSNQT

SFTCQDIFKE TNATYPSSDV PCDATLTEKS

FETDMNLNFQ NL

One embodiment provides soluble mTCR-17 α chain (Q21-L242) having 90%, 95%, 99%, or 100% sequence identity to (SEQ ID NO:48):

```
1    QQKVQQSPES LIVPEGGMAS LNCTSSDRNV DYFWWYRQHS GKSPKMLMSI

51   FSNGEKEEGR FTVHLNKASL HTSLHIRDSQ PSDSALYLCA ASMTGGYKVV

101  FGSGTRLLVS PDIQNPEPAV YQLKDPRSQD STLCLFTDFD SQINVPKTME

151  SGTFITDKTV LDMKAMDSKS NGAIAWSNQT SFTCQDIFKE TNATYPSSDV

201  PCDATLTEKS FETDMNLNFQ NL
```

Another embodiment provides soluble mTCR-38 α chain (Q21-L242) having 90%, 95%, 99%, or 100% sequence identity to (SEQ ID NO:49):

```
1    QQKVQQSPES LIVPEGGMAS LNCTSSDRNV DYFWWYRQHS GKSPKMLMSI

51   FSNGEKEEGR FTVHLNKASL HTSLHIRDSQ PSDSALYLCA ATLTGGYKVV

101  FGSGTRLLVS PDIQNPEPAV YQLKDPRSQD STLCLFTDFD SQINVPKTME

151  SGTFITDKTV LDMKAMDSKS NGAIAWSNQT SFTCQDIFKE TNATYPSSDV

201  PCDATLTEKS FETDMNLNFQ NL
```

8. The Extracellular Domain of TCR-1, 2, 3, 6, 8, 10, and 11 β Chains (Underlined are the Vβ)

One embodiment provides soluble mTCR-1, 2, 8, 11 βchain (E18-Y276) having at least 90%, 95%, 99%, or 100% sequence identity to (SEQ ID NO:50):

EAA VTQSPRNKVT VTGGNVTLSC RQTNSHNYMY WYRQDTGHGL

RLIHYSYGAG NLQIGDVPDG YKATRTTQED

FFLLLELASP SQTSLYFCAS SDAGTSQNTL YFGAGTRLSV

LEDLRNVTPP KVSLFEPSKA EIANKRKATL

VCLARGFFPD HVELSWWVNG KEVHSGVSTD PQAYKESNYS

YCLSSRLRVS ATFWHNPRNH FRCQVQFHGL

SEEDKWPEGS PKPVTQNISA EAWGRADCGI TSASYQQGVL

SATILY

Still another embodiment soluble mTCR-3 β chain (E18-Y276) having at least 90%, 95%, 99%, or 100% sequence identity to (SEQ ID NO:51):

EAA VTQSPRNKVT VTGGNVTLSC RQTNSHNYMY WYRQDTGHGL

RLIHYSYGAG NLQIGDVPDG YKATRTTQED

FFLLLELASP SQTSLYFCAS SDAGTAQNTL YFGAGTRLSV

LEDLRNVTPP KVSLFEPSKA EIANKRKATL

VCLARGFFPD HVELSWWVNG KEVHSGVSTD PQAYKESNYS

YCLSSRLRVS ATFWHNPRNH FRCQVQFHGL

SEEDKWPEGS PKPVTQNISA EAWGRADCGI TSASYQQGVL

SATILYEILL

Another embodiment soluble mTCR-6 β chain (E18-Y276) having at least 90%, 95%, 99%, or 100% sequence identity to (SEQ ID NO:52):

EAAVTQSPRN KVTVTGGNVT LSCRQTNSHN YMYWYRQDTG

HGLRLIHYSY GAGNLQIGDV PDGYKATRTT

QEDFFLLLEL ASPSQTSLYF CASCDAGVSQ NTLYFGAGTR

LSVLEDLRNV TPPKVSLFEP SKAEIANKRK

ATLVCLARGF FPDHVELSWW VNGKEVHSGV STDPQAYKES

```
NYSYCLSSRL RVSATFWHNP RNHFRCQVQF

HGLSEEDKWP EGSPKPVTQN ISAEAWGRAD CGITSASYQQ

GVLSATILY
```

Another embodiment soluble mTCR-10 β chain (E18-Y276) having at least 90%, 95%, 99%, or 100% sequence identity to (SEQ ID NO:53):

```
EAAVTQSPRN KVTVTGGNVT LSCRQTNSHN YMYWYRQDTG

HGLRLIHYSY GAGNLQIGDV PDGYKATRTT

QEDFFLLLEL ASPSQTSLYF CASSDHGTGQ NTLYFGAGTR

LSVLEDLRNV TPPKVSLFEP SKAEIANKRK

ATLVCLARGF FPDHVELSWW VNGKEVHSGV STDPQAYKES

NYSYCLSSRL RVSATFWHNP RNHFRCQVQF

HGLSEEDKWP EGSPKPVTQN ISAEAWGRAD CGITSASYQQ

GVLSATILY
```

9. Fusion Protein Sequences of Designed mTCRs

Fusion Proteins

In another embodiment, fusion proteins are provided that contain a first polypeptide domain and a second polypeptide. The fusion proteins can optionally contain a targeting domain that targets the fusion protein specific cells or tissues, for example the tumor cells or tumor cell-associated neovasculature.

The fusion proteins also optionally contain a peptide or polypeptide linker domain that separates the first polypeptide domain from the antigen-binding domain.

Fusion proteins disclosed herein are of formula I:

$$N—R_1—R_2—R_3—C$$

wherein "N" represents the N-terminus of the fusion protein, "C" represents the C-terminus of the fusion protein, "$R_1$" is one of the disclosed α mTCR chains or a fragment thereof. "R2" is a peptide/polypeptide linker domain, and "$R_3$" is a β mTCR chain or fragment thereof. In an alternative embodiment, $R_1$ is a 3 mTCR chain or fragment thereof and $R_3$ is an α mTCR chain.

Optionally, the fusion proteins additionally contain a domain that functions to dimerize or multimerize two or more fusion proteins. The domain that functions to dimerize or multimerize the fusion proteins can either be a separate domain, or alternatively can be contained within one of one of the other domains of the fusion protein.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

The modular nature of the fusion proteins and their ability to dimerize or multimerize in different combinations provides a wealth of options for targeting molecules that function to enhance an immune response to the tumor cell microenvironment.

Another embodiment provides a fusion protein according to formula II, $$N—R_1—R_2—R_3—R_2—R_4—C$$

wherein "N" represents the N-terminus of the fusion protein, "C" represents the C-terminus of the fusion protein, "$R_1$" is one of the disclosed α mTCR chains or a fragment thereof "$R_2$" is a peptide/polypeptide linker domain, and "$R_3$" is a 3 mTCR chain or fragment thereof and "R4" is an anti-CD3 single chain antibody. Anti-CD3 single chain antibodies are known in the art and are commercially available.

One embodiment provides fusion protein of designed mTCR-1 (α chain is underlined, P2A is bolded, and β chain is double underlined) having at least 90%, 95%, 99%, or 100% sequence identity to (SEQ ID NO:54):

```
  1  MKSFSISLVV LWLQLNWVNS QQKVQQSPES LIVPEGGMAS LNCTSSDRNV

51  DYFWWYRQHS GKSPKMLMSI FSNGEKEEGR FTVHLNKASL HTSLHIRDSQ

101  PSDSALYLCA ASITNAYKVI FGKGTHLHVL PNIQNPEPAV YQLKDPRSQD

151  STLCLFTDFD SQINVPKTME SGTFITDKTV LDMKAMDSKS NGAIAWSNQT

201  SFTCQDIFKE TNATYPSSDV PCDATLTEKS FETDMNLNFQ NLSVMGLRIL

251  LLKVAGFNLL MTLRLWSSGS RAKRSGSGAT NFSLLKQAGD VEENPGPRMG

301  SRLFLVLSLL CTKHMEAAVT QSPRNKVTVT GGNVTLSCRQ TNSHNYMYWY

351  RQDTGHGLRL IHYSYGAGNL QIGDVPDGYK ATRTTQEDFF LLLELASPSQ

401  TSLYFCASSD AGTSQNTLYF GAGTRLSVLE DLRNVTPPKV SLFEPSKAEI

451  ANKRKATLVC LARGFFPDHV ELSWWVNGKE VHSGVSTDPQ AYKESNYSYC

501  LSSRLRVSAT FWHNPRNHFR CQVQFHGLSE EDKWPEGSPK PVTQNISAEA

551  WGRADCGITS ASYQQGVLSA TILYEILLGK ATLYAVLVST LVVMAMVKRK

601  NS
```

The α chain is underlined, the β chain is double underlined, and the P2A and furin cleavage site (from US2016/0137715 A1) is in bold.

Another embodiment provides designed mTCR-2 (α chain, P2A, and β chain) having at least 90%, 95%, 99%, or 100% sequence identity to (SEQ ID NO:55)

```
  1   MKSFSISLVV LWLQLNWVNS QQKVQQSPES LIVPEGGMAS LNCTSSDRNV
 51   DYFWWYRQHS GKSPKMLMSI FSNGEKEEGR FTVHLNKASL HTSLHIRDSQ
101   PSDSALYLCA ASTVNAYKVI FGKGTHLHVL PNIQNPEPAV YQLKDPRSQD
151   STLCLFTDFD SQINVPKTME SGTFITDKTV LDMKAMDSKS NGAIAWSNQT
201   SFTCQDIFKE TNATYPSSDV PCDATLTEKS FETDMNLNFQ NLSVMGLRIL
251   LLKVAGFNLL MTLRLWSSGS RAKRSGSGAT NFSLLKQAGD VEENPGPRMG
301   SRLFLVLSLL CTKHMEAAVT QSPRNKVTVT GGNVTLSCRQ TNSHNYMYWY
351   RQDTGHGLRL IHYSYGAGNL QIGDVPDGYK ATRTTQEDFF LLLELASPSQ
401   TSLYFCASSD AGTSQNTLYF GAGTRLSVLE DLRNVTPPKV SLFEPSKAEI
451   ANKRKATLVC LARGFFPDHV ELSWWVNGKE VHSGVSTDPQ AYKESNYSYC
501   LSSRLRVSAT FWHNPRNHFR CQVQFHGLSE EDKWPEGSPK PVTQNISAEA
551   WGRADCGITS ASYQQGVLSA TILYEILLGK ATLYAVLVST LVVMAMVKRK
601   NS
```

Another embodiment provides designed mTCR-3 (α chain, P2A, and β chain) having at least 90%, 95%, 99% or 100% sequence identity to (SEQ ID NO:56):

```
  1   MKSFSISLVV LWLQLNWVNS QQKVQQSPES LIVPEGGMAS LNCTSSDRNV
 51   DYFWWYRQHS GKSPKMLMSI FSNGEKEEGR FTVHLNKASL HTSLHIRDSQ
101   PSDSALYLCA ASMAGGYKVV FGSGTRLLVS PDIQNPEPAV YQLKDPRSQD
151   STLCLFTDFD SQINVPKTME SGTFITDKTV LDMKAMDSKS NGAIAWSNQT
201   SFTCQDIFKE TNATYPSSDV PCDATLTEKS FETDMNLNFQ NLSVMGLRIL
251   LLKVAGFNLL MTLRLWSSGS RAKRSGSGAT NFSLLKQAGD VEENPGPRMG
301   SRLFLVLSLL CTKHMEAAVT QSPRNKVTVT GGNVTLSCRQ TNSHNYMYWY
351   RQDTGHGLRL IHYSYGAGNL QIGDVPDGYK ATRTTQEDFF LLLELASPSQ
401   TSLYFCASSD AGTAQNTLYF GAGTRLSVLE DLRNVTPPKV SLFEPSKAEI
451   ANKRKATLVC LARGFFPDHV ELSWWVNGKE VHSGVSTDPQ AYKESNYSYC
501   LSSRLRVSAT FWHNPRNHFR CQVQFHGLSE EDKWPEGSPK PVTQNISAEA
551   WGRADCGITS ASYQQGVLSA TILYEILLGK ATLYAVLVST LVVMAMVKRK
601   NS
```

Another embodiment provides designed mTCR-6 (α chain, P2A, and β chain) having at least 90%, 95%, 99% or 100% sequence identity to (SEQ ID NO:57):

```
  1   MKSFSISLVV LWLQLNWVNS QQKVQQSPES LIVPEGGMAS LNCTSSDRNV
 51   DYFWWYRQHS GKSPKMLMSI FSNGEKEEGR FTVHLNKASL HTSLHIRDSQ
101   PSDSALYLCA ASMINAYKVI FGKGTHLHVL PNIQNPEPAV YQLKDPRSQD
151   STLCLFTDFD SQINVPKTME SGTFITDKTV LDMKAMDSKS NGAIAWSNQT
201   SFTCQDIFKE TNATYPSSDV PCDATLTEKS FETDMNLNFQ NLSVMGLRIL
251   LLKVAGFNLL MTLRLWSSGS RAKRSGSGAT NFSLLKQAGD VEENPGPRMG
```

```
301    SRLFLVLSLL CTKHMEAAVT QSPRNKVTVT GGNVTLSCRQ TNSHNYMYWY

351    RQDTGHGLRL IHYSYGAGNL QIGDVPDGYK ATRTTQEDFF LLLELASPSQ

401    TSLYFCASSD AGVSQNTLYF GAGTRLSVLE DLRNVTPPKV SLFEPSKAEI

451    ANKRKATLVC LARGFFPDHV ELSWWVNGKE VHSGVSTDPQ AYKESNYSYC

501    LSSRLRVSAT FWHNPRNHFR CQVQFHGLSE EDKWPEGSPK PVTQNISAEA

551    WGRADCGITS ASYQQGVLSA TILYEILLGK ATLYAVLVST LVVMAMVKRK

601    NS
```

Another embodiment provides designed mTCR-8 (α chain, P2A, and β chain) having at least 90%, 95%, 99% or 100% sequence identity to (SEQ ID NO:58):

```
  1    MKSFSISLVV LWLQLNWVNS QQKVQQSPES
       LIVPEGGMAS LNCTSSDRNV

51    DYFWWYRQHS GKSPKMLMSI FSNGEKEEGR
       FTVHLNKASL HTSLHIRDSQ

101    PSDSALYLCA ASISGGYKVV FGSGTRLLVS
       PDIQNPEPAV YQLKDPRSQD

151    STLCLFTDFD SQINVPKTME SGTFITDKTV
       LDMKAMDSKS NGAIAWSNQT

201    SFTCQDIFKE TNATYPSSDV PCDATLTEKS
       FETDMNLNFQ NLSVMGLRIL

251    LLKVAGFNLL MTLRLWSSGS RAKRSGSGAT
       NFSLLKQAGD VEENPGPRMG

301    SRLFLVLSLL CTKHMEAAVT QSPRNKVTVT
       GGNVTLSCRQ TNSHNYMYWYEE

351    RQDTGHGLRL IHYSYGAGNL QIGDVPDGYK
       ATRTTQEDFF LLLELASPSQ

401    TSLYFCASSD AGTSQNTLYF GAGTRLSVLE
       DLRNVTPPKV SLFEPSKAEI

451    ANKRKATLVC LARGFFPDHV ELSWWVNGKE
       VHSGVSTDPQ AYKESNYSYC

501    LSSRLRVSAT FWHNPRNHFR CQVQFHGLSE
       EDKWPEGSPK PVTQNISAEA

551    WGRADCGITS ASYQQGVLSA TILYEILLGK
       ATLYAVLVST LVVMAMVKRK

601    NS
```

Another embodiment provides designed mTCR-10 (α chain, P2A, and β chain) having at least 90%, 95%, 99% or 100% sequence identity to (SEQ ID NO:59):

```
  1    MKSFSISLVV LWLQLNWVNS QQKVQQSPES
       LIVPEGGMAS LNCTSSDRNV

51    DYFWWYRQHS GKSPKMLMSI FSNGEKEEGR
       FTVHLNKASL HTSLHIRDSQ

101    PSDSALYLCA ASIVGGYKVV FGSGTRLLVS
       PDIQNPEPAV YQLKDPRSQD

151    STLCLFTDFD SQINVPKTME SGTFITDKTV
       LDMKAMDSKS NGAIAWSNQT

201    SFTCQDIFKE TNATYPSSDV PCDATLTEKS
       FETDMNLNFQ NLSVMGLRIL

251    LLKVAGFNLL MTLRLWSSGS RAKRSGSGAT
       NFSLLKQAGD VEENPGPRMG

301    SRLFLVLSLL CTKHMEAAVT QSPRNKVTVT
       GGNVTLSCRQ TNSHNYMYWY

351    RQDTGHGLRL IHYSYGAGNL QIGDVPDGYK
       ATRTTQEDFF LLLELASPSQ

401    TSLYFCASSD HGTGQNTLYF GAGTRLSVLE
       DLRNVTPPKV SLFEPSKAEI

451    ANKRKATLVC LARGFFPDHV ELSWWVNGKE
       VHSGVSTDPQ AYKESNYSYC

501    LSSRLRVSAT FWHNPRNHFR CQVQFHGLSE
       EDKWPEGSPK PVTQNISAEA

551    WGRADCGITS ASYQQGVLSA TILYEILLGK
       ATLYAVLVST LVVMAMVKRK

601    NS
```

Another embodiment provides designed mTCR-11 (α chain, P2A, and β chain) having at least 90%, 95%, 99% or 100% sequence identity to (SEQ ID NO:60):

```
  1    MKSFSISLVV LWLQLNWVNS QQKVQQSPES
       LIVPEGGMAS LNCTSSDRNV

51    DYFWWYRQHS GKSPKMLMSI FSNGEKEEGR
       FTVHLNKASL HTSLHIRDSQ

101    PSDSALYLCA ASKTGGYKVV FGSGTRLLVS
       PDIQNPEPAV YQLKDPRSQD
```

```
151 STLCLFTDFD SQINVPKTME SGTFITDKTV
    LDMKAMDSKS NGAIAWSNQT

201 SFTCQDIFKE TNATYPSSDV PCDATLTEKS
    FETDMNLNFQ NLSVMGLRIL

251 LLKVAGFNLL MTLRLWSSGS RAKRSGSGAT
    NFSLLKQAGD VEENPGPRMG

301 SRLFLVLSLL CTKHMEAAVT QSPRNKVTVT
    GGNVTLSCRQ TNSHNYMYWY

351 RQDTGHGLRL IHYSYGAGNL QIGDVPDGYK
    ATRTTQEDFF LLLELASPSQ

401 TSLYFCASSD AGTSQNTLYF GAGTRLSVLE
    DLRNVTPPKV SLFEPSKAEI

451 ANKRKATLVC LARGFFPDHV ELSWWVNGKE
    VHSGVSTDPQ AYKESNYSYC

501 LSSRLRVSAT FWHNPRNHFR CQVQFHGLSE
    EDKWPEGSPK PVTQNISAEA

551 WGRADCGITS ASYQQGVLSA TILYEILLGK
    ATLYAVLVST LVVMAMVKRK

601 NS
```

One embodiment provides designed mTCR-17 (α chain, P2A, and β chain) having at least 90%, 95%, 99% or 100% sequence identity to (SEQ ID NO:61):

```
  1 MKSFSISLVV LWLQLNWVNS QQKVQQSPES
    LIVPEGGMAS LNCTSSDRNV

51 DYFWWYRQHS GKSPKMLMSI FSNGEKEEGR
    FTVHLNKASL HTSLHIRDSQ

101 PSDSALYLCA ASMTGGYKVV FGSGTRLLVS
    PDIQNPEPAV YQLKDPRSQD

151 STLCLFTDFD SQINVPKTME SGTFITDKTV
    LDMKAMDSKS NGAIAWSNQT

201 SFTCQDIFKE TNATYPSSDV PCDATLTEKS
    FETDMNLNFQ NLSVMGLRIL

251 LLKVAGFNLL MTLRLWSSGS RAKRSGSGAT
    NFSLLKQAGD VEENPGPRMG

301 SRLFLVLSLL CTKHMEAAVT QSPRNKVTVT
    GGNVTLSCRQ TNSHNYMYWY

351 RQDTGHGLRL IHYSYGAGNL QIGDVPDGYK
    ATRTTQEDFF LLLELASPSQ

401 TSLYFCASSD AGTSQNTLYF GAGTRLSVLE
    DLRNVTPPKV SLFEPSKAEI

451 ANKRKATLVC LARGFFPDHV ELSWWVNGKE
    VHSGVSTDPQ AYKESNYSYC

501 LSSRLRVSAT FWHNPRNHFR CQVQFHGLSE
    EDKWPEGSPK PVTQNISAEA

551 WGRADCGITS ASYQQGVLSA TILYEILLGK
    ATLYAVLVST LVVMAMVKRK

601 NS
```

One embodiment provides designed mTCR-38 (α chain, P2A, and β chain) having at least 90%, 95%, 99% or 100% sequence identity to (SEQ ID NO:62):

```
  1 MKSFSISLVV LWLQLNWVNS QQKVQQSPES
    LIVPEGGMAS LNCTSSDRNV

51 DYFWWYRQHS GKSPKMLMSI FSNGEKEEGR
    FTVHLNKASL HTSLHIRDSQ

101 PSDSALYLCA ATLTGGYKVV FGSGTRLLVS
    PDIQNPEPAV YQLKDPRSQD

151 STLCLFTDFD SQINVPKTME SGTFITDKTV
    LDMKAMDSKS NGAIAWSNQT

201 SFTCQDIFKE TNATYPSSDV PCDATLTEKS
    FETDMNLNFQ NLSVMGLRIL

251 LLKVAGFNLL MTLRLWSSGS RAKRSGSGAT
    NFSLLKQAGD VEENPGPRMG

301 SRLFLVLSLL CTKHMEAAVT QSPRNKVTVT
    GGNVTLSCRQ TNSHNYMYWY

351 RQDTGHGLRL IHYSYGAGNL QIGDVPDGYK
    ATRTTQEDFF LLLELASPSQ

401 TSLYFCASSD AGTSQNTLYF GAGTRLSVLE
    DLRNVTPPKV SLFEPSKAEI

451 ANKRKATLVC LARGFFPDHV ELSWWVNGKE
    VHSGVSTDPQ AYKESNYSYC

501 LSSRLRVSAT FWHNPRNHFR CQVQFHGLSE
    EDKWPEGSPK PVTQNISAEA

551 WGRADCGITS ASYQQGVLSA TILYEILLGK
    ATLYAVLVST LVVMAMVKRK

601 NS
```

10. Nucleotide Sequences of the Designed TCR-1, TCR-2, TCR-3, TCR-6, TCR-8, TCR-10, TCR-11, TCR-17, and TCR-38:

The sequences are based on the above protein sequences and codon optimized for expression in human cells.

One embodiment provides a designed mTCR-1 (a is underlined, P2A is bolded, and R is double underlined) having a nucleic acid sequence that is at least 90%, 95%, 99%, or 100% sequence identity to (SEQ ID NO:63):

```
   1 ATGAAATCTT TTAGCATCTC CCTGGTCGTC
     CTGTGGCTGC AGCTGAATTG GGTGAATAGT

61 CAGCAGAAGG TCCAGCAGTC CCCCGAGTCC
     CTGATCGTGC CTGAGGGCGG CATGGCCTCT

121 CTGAACTGCA CCAGCTCCGA CCGGAATGTG
     GATTATTCT GGTGGTACAG ACAGCACTCT

181 GGCAAGAGCC CAAAGATGCT GATGTCCATC
     TTCTCTAACG GCGAGAAGGA GGAGGGCCGG

241 TTTACAGTGC ACCTGAATAA GGCTAGCCTG
     CACACCTCCC TGCACATCAG AGACTCCAG

301 CCCTCCGATT CTGCCCTGTA TCTGTGCGCC
     GCCTCTATCA CAAACGCCTA CAAAGTGATC

361 TTCGGCAAGG GAACCCACCT GCACGTGCTG
     CCTAACATCC AGAATCCAGA GCCCGCCGTG

421 TATCAGCTGA AGGACCCACG GAGCCAGGAT
     AGCACCCTGT GCCTGTTCAC CGACTTTGAT

481 AGCCAGATCA ATGTGCCTAA GACAATGGAG
     TCCGGCACCT TTATCACAGA CAAGACCGTG

541 CTGGATATGA AGGCCATGGA CAGCAAGTCC
     AACGGCGCCA TCGCCTGGTC TAATCAGACA

601 AGCTTCACCT GCCAGGATAT CTTTAAGGAG
     ACAAACGCCA CCTACCCATC TAGCGACGTG

661 CCCTGTGATG CCACCCTGAC AGAGAAGAGC
     TTCGAGACAG ACATGAACCT GAATTTTCAG

721 AACCTGTCCG TGATGGGCCT GAGAATCCTG
     CTGCTGAAGG TGGCCGGCTT CAATCTGCTG

781 ATGACACTGC GCCTGTGGTC CTCT**GGCTCT
     AGGGCAAAGC GGAGCGGCAG CGGAGCAACC**

841 **AACTTCAGCC TGCTGAAGCA GGCCGGCGAT
     GTGGAGGAGA ATCCTGGCCC ACGG**ATGGGC

901 TCTAGACTGT TCTGGTGCT GAGCCTGCTG
     TGCACAAAGC ACATGGAGGC AGCAGTGACC

961 CAGTCCCCAC GGAACAAGGT GACCGTGACA
     GGCGGCAATG TGACACTGAG CTGTAGACAG

1021 ACCAACTCCC ACAATTACAT GTATTGGTAC
     CGGCAGGATA CCGGACACGG CCTGAGACTG

1081 ATCCACTATA GCTACGGCGC CGGCAATCTG
     CAGATCGGCG ACGTGCCAGA TGGCTATAAG

1141 GCCACAAGGA CCACACAGGA GGACTTCTTT
     CTGCTGCTGG AGCTGGCCTC CCCCTCTCAG

1201 ACCTCTCTGT ATTTCTGCGC CAGCTCCGAT
     GCCGGCACAA GCCAGAACAC CCTGTACTTT

1261 GGAGCAGGAA CAAGGCTGTC CGTGCTGGAG
     GACCTGCGCA ATGTGACCCC CCCTAAGGTG

1321 TCCCTGTTCG AGCCTTCTAA GGCCGAGATC
     GCCAACAAGA GGAAGGCCAC CCTGGTGTGC

1381 CTGGCAAGGG GCTTCTTTCC AGATCACGTG
     GAGCTGTCCT GGTGGGTGAA TGGCAAGGAG

1441 GTGCACTCTG GCGTGAGCAC AGACCCCCAG
     GCCTACAAGG AGTCCAACTA TTCTTACTGC

1501 CTGTCTAGCC GGCTGAGAGT GAGCGCCACC
     TTTTGGCACA ACCCCAGGAA TCACTTCCGC

1561 TGTCAGGTGC AGTTTCACGG CCTGTCCGAG
     GAGGATAAGT GGCCTGAGGG CTCTCCCAAG

1621 CCTGTGACAC AGAACATCAG CGCCGAGGCA
     TGGGGAAGGG CAGACTGTGG CATCACCAGC

1681 GCCTCCTATC AGCAGGGCGT GCTGAGCGCC
     ACAATCCTGT ACGAGATCCT GCTGGGCAAG

1741 GCCACCCTGT ATGCTGTGCT GGTGTCAACT
     CTGGTGGTCA TGGCTATGGT GAAACGGAAA

1801 AACTCCTAA
```

Another embodiment provides a designed mTCR-2 (α is under lined, P2A is bolded, and β double underlined) having at least 90%, 95%, 99%, or 100% sequence identity to (SEQ ID NO:64):

```
   1 ATGAAATCTT TTAGCATCTC CCTGGTCGTC
     CTGTGGCTGC AGCTGAATTG GGTGAATAGT

61 CAGCAGAAGG TCCAGCAGTC CCCCGAGTCC
     CTGATCGTGC CTGAGGGCGG CATGGCCTCT

121 CTGAACTGCA CCAGCTCCGA CCGGAATGTG
     GATTATTCT GGTGGTACAG ACAGCACTCT

181 GGCAAGAGCC CAAAGATGCT GATGTCCATC
     TTCTCTAACG GCGAGAAGGA GGAGGGCCGG

241 TTTACAGTGC ACCTGAATAA GGCTAGCCTG
     CACACCTCCC TGCACATCAG AGACTCCAG

301 CCCTCCGATT CTGCCCTGTA TCTGTGCGCC
     GCCTCTACCG TGAACGCCTA CAAAGTGATC

361 TTCGGCAAGG GAACCCACCT GCACGTGCTG
     CCTAACATCC AGAATCCAGA GCCCGCCGTG

421 TATCAGCTGA AGGACCCACG GAGCCAGGAT
     AGCACCCTGT GCCTGTTCAC CGACTTTGAT
```

-continued
```
 481 AGCCAGATCA ATGTGCCTAA GACAATGGAG
     TCCGGCACCT TTATCACAGA CAAGACCGTG
 541 CTGGATATGA AGGCCATGGA CAGCAAGTCC
     AACGGCGCCA TCGCCTGGTC TAATCAGACA
 601 AGCTTCACCT GCCAGGATAT CTTTAAGGAG
     ACAAACGCCA CCTACCCATC TAGCGACGTG
 661 CCCTGTGATG CCACCCTGAC AGAGAAGAGC
     TTCGAGACAG ACATGAACCT GAATTTTCAG
 721 AACCTGTCCG TGATGGGCCT GAGAATCCTG
     CTGCTGAAGG TGGCCGGCTT CAATCTGCTG
 781 ATGACACTGC GCCTGTGGTC CTCTGGCTCT
     AGGGCAAAGC GGAGCGGCAG CGGAGCAACC
 841 AACTTCAGCC TGCTGAAGCA GGCCGGCGAT
     GTGGAGGAGA ATCCTGGCCC ACGGATGGGC
 901 TCTAGACTGT TTCTGGTGCT GAGCCTGCTG
     TGCACAAAGC ACATGGAGGC AGCAGTGACC
 961 CAGTCCCCAC GGAACAAGGT GACCGTGACA
     GGCGGCAATG TGACACTGAG CTGTAGACAG
1021 ACCAACTCCC ACAATTACAT GTATTGGTAC
     CGGCAGGATA CCGGACACGG CCTGAGACTG
1081 ATCCACTATA GCTACGGCGC CGGCAATCTG
     CAGATCGGCG ACGTGCCAGA TGGCTATAAG
1141 GCCACAAGGA CCACACAGGA GGACTTCTTT
     CTGCTGCTGG AGCTGGCCTC CCCCTCTCAG
1201 ACCTCTCTGT ATTTCTGCGC CAGCTCCGAT
     GCCGGCACAA GCCAGAACAC CCTGTACTTT
1261 GGAGCAGGAA CAAGGCTGTC CGTGCTGGAG
     GACCTGCGCA ATGTGACCCC CCCTAAGGTG
1321 TCCCTGTTCG AGCCTTCTAA GGCCGAGATC
     GCCAACAAGA GGAAGGCCAC CCTGGTGTGC
1381 CTGGCAAGGG GCTTCTTTCC AGATCACGTG
     GAGCTGTCCT GGTGGGTGAA TGGCAAGGAG
1441 GTGCACTCTG GCGTGAGCAC AGACCCCCAG
     GCCTACAAGG AGTCCAACTA TTCTTACTGC
1501 CTGTCTAGCC GGCTGAGAGT GAGCGCCACC
     TTTTGGCACA ACCCCAGGAA TCACTTCCGC
1561 TGTCAGGTGC AGTTCACGG CCTGTCCGAG
     GAGGATAAGT GGCCTGAGGG CTCTCCCAAG
1621 CCTGTGACAC AGAACATCAG CGCCGAGGCA
     TGGGGAAGGG CAGACTGTGG CATCACCAGC
1681 GCCTCCTATC AGCAGGGCGT GCTGAGCGCC
     ACAATCCTGT ACGAGATCCT GCTGGGCAAG
1741 GCCACCCTGT ATGCTGTGCT GGTGTCAACT
     CTGGTGGTCA TGGCTATGGT GAAACGGAAA
1801 AACTCCTAA
```

Another embodiment provides a designed mTCR-3 (α is underlined, P2A is bolded, and β is double underlined) having at least 90%, 95%, 99%, or 100% sequence identity to (SEQ ID NO:65):

```
   1 ATGAAATCTT TTAGCATCTC CCTGGTCGTC
     CTGTGGCTGC AGCTGAATTG GGTGAATAGT
  61 CAGCAGAAGG TCCAGCAGTC CCCCGAGTCC
     CTGATCGTGC CTGAGGGCGG CATGGCCTCT
 121 CTGAACTGCA CCAGCTCCGA CCGGAATGTG
     GATTATTTCT GGTGGTACAG ACAGCACTCT
 181 GGCAAGAGCC CAAAGATGCT GATGTCCATC
     TTCTCTAACG GCGAGAAGGA GGAGGGCCGG
 241 TTTACAGTGC ACCTGAATAA GGCTAGCCTG
     CACACCTCCC TGCACATCAG AGACTCCCAG
 301 CCCTCCGATT CTGCCCTGTA TCTGTGCGCC
     GCCTCTATGG CCGGCGGCTA CAAAGTGGTG
 361 TTCGGCAGCG GAACCCGGCT GCTGGTGAGC
     CCTGACATCC AGAATCCAGA GCCCGCCGTG
 421 TATCAGCTGA AGGACCACG GAGCCAGGAT
     AGCACCCTGT GCCTGTTCAC CGACTTTGAT
 481 AGCCAGATCA ATGTGCCTAA GACAATGGAG
     TCCGGCACCT TTATCACAGA CAAGACCGTG
 541 CTGGATATGA AGGCCATGGA CAGCAAGTCC
     AACGGCGCCA TCGCCTGGTC TAATCAGACA
 601 AGCTTCACCT GCCAGGATAT CTTTAAGGAG
     ACAAACGCCA CCTACCCATC TAGCGACGTG
 661 CCCTGTGATG CCACCCTGAC AGAGAAGAGC
     TTCGAGACAG ACATGAACCT GAATTTTCAG
 721 AACCTGTCCG TGATGGGCCT GAGAATCCTG
     CTGCTGAAGG TGGCCGGCTT CAATCTGCTG
 781 ATGACACTGC GCCTGTGGTC CTCTGGCTCT
     AGGGCAAAGC GGAGCGGCAG CGGAGCAACC
 841 AACTTCAGCC TGCTGAAGCA GGCCGGCGAT
     GTGGAGGAGA ATCCTGGCCC ACGGATGGGC
```

```
 901 TCTAGACTGT TTCTGGTGCT GAGCCTGCTG
     TGCACAAAGC ACATGGAGGC AGCAGTGACC
 961 CAGTCCCCAC GGAACAAGGT GACCGTGACA
     GGCGGCAATG TGACACTGAG CTGTAGACAG
1021 ACCAACTCCC ACAATTACAT GTATTGGTAC
     CGGCAGGATA CCGGACACGG CCTGAGACTG
1081 ATCCACTATA GCTACGGCGC CGGCAATCTG
     CAGATCGGCG ACGTGCCAGA TGGCTATAAG
1141 GCCACAAGGA CCACACAGGA GGACTTCTTT
     CTGCTGCTGG AGCTGGCCTC CCCCTCTCAG
1201 ACCTCTCTGT ATTTCTGCGC CAGCTCCGAT
     GCCGGCACAG CCCAGAACAC CCTGTACTTT
1261 GGAGCAGGAA CAAGGCTGTC CGTGCTGGAG
     GACCTGCGCA ATGTGACCCC CCCTAAGGTG
1321 TCCCTGTTCG AGCCTTCTAA GGCCGAGATC
     GCCAACAAGA GGAAGGCCAC CCTGGTGTGC
1381 CTGGCAAGGG GCTTCTTTCC AGATCACGTG
     GAGCTGTCCT GGTGGGTGAA TGGCAAGGAG
1441 GTGCACTCTG GCGTGAGCAC AGACCCCCAG
     GCCTACAAGG AGTCCAACTA TTCTTACTGC
1501 CTGTCTAGCC GGCTGAGAGT GAGCGCCACC
     TTTTGGCACA ACCCCAGGAA TCACTTCCGC
1561 TGTCAGGTGC AGTTTCACGG CCTGTCCGAG
     GAGGATAAGT GGCCTGAGGG CTCTCCCAAG
1621 CCTGTGACAC AGAACATCAG CGCCGAGGCA
     TGGGGAAGGG CAGACTGTGG CATCACCAGC
1681 GCCTCCTATC AGCAGGGCGT GCTGAGCGCC
     ACAATCCTGT ACGAGATCCT GCTGGGCAAG
1741 GCCACCCTGT ATGCTGTGCT GGTGTCAACT
     CTGGTGGTCA TGGCTATGGT GAAACGGAAA
1801 AACTCCTAA
```

Another embodiment provides a designed mTCR-6 (α is underlined, P2A is bolded, and β is double underlined) having at least 90%, 95%, 99%, or 100% sequence identity to (SEQ ID NO:66):

```
   1 ATGAAGTCCT TCTCTATCAG CCTGGTGGTG
     CTGTGGCTGC AGCTGAACTG GGTGAATAGC
  61 CAGCAGAAGG TGCAGCAGTC TCCTGAGAGC
     CTGATCGTGC CAGAGGGCGG CATGGCCTCC
 121 CTGAACTGCA CCAGCTCCGA CCGGAATGTG
     GATTATTTTT GGTGGTACAG ACAGCACTCC
 181 GGCAAGTCTC CCAAGATGCT GATGAGCATC
     TTCTCCAACG GCGAGAAGGA GGAGGGCCGG
 241 TTTACAGTGC ACCTGAATAA GGCCTCTCTG
     CACACCAGCC TGCACATCAG AGACTCCCAG
 301 CCTTCCGATT CTGCCCTGTA TCTGTGCGCC
     GCCTCTATGA TCAATGCCTA CAAAGTGATC
 361 TTCGGCAAGG GCACACACCT GCACGTGCTG
     CCCAACATCC AGAATCCAGA GCCCGCCGTG
 421 TATCAGCTGA AGGACCCTCG GTCTCAGGAT
     AGCACCCTGT GCCTGTTCAC CGACTTTGAT
 481 AGCCAGATCA ATGTGCCAAA GACCATGGAG
     TCCGGCACCT TTATCACAGA CAAGACCGTG
 541 CTGGATATGA AGGCCATGGA CAGCAAGTCC
     AACGGCGCCA TCGCCTGGTC CAATCAGACA
 601 TCTTTCACCT GCCAGGATAT CTTTAAGGAG
     ACAAACGCCA CCTACCCATC TAGCGACGTG
 661 CCCTGTGATG CCACCCTGAC AGAGAAGAGC
     TTCGAGACCG ACATGAACCT GAATTTTCAG
 721 AACCTGTCCG TGATGGGCCT GAGAATCCTG
     CTGCTGAAGG TGGCCGGCTT CAATCTGCTG
 781 ATGACACTGC GCCTGTGGTC CTCT**GGCTCT
     AGGGCAAAGC GGAGCGGCAG CGGAGCAACC
 841 AACTTCAGCC TGCTGAAGCA GGCCGGCGAT
     GTGGAGGAGA ATCCTGGCCC ACGG**ATGGGC
 901 TCCAGACTGT TTCTGGTGCT GTCTCTGCTG
     TGCACAAAGC ACATGGAGGC AGCAGTGACC
 961 CAGAGCCCAC GGAACAAGGT GACCGTGACA
     GGCGGCAATG TGACACTGTC TTGTAGACAG
1021 ACCAACAGCC ACAATTACAT GTATTGGTAC
     CGGCAGGATA CCGGACACGG CCTGAGACTG
1081 ATCCACTATT CCTACGGAGC AGGAAACCTG
     CAGATCGGCG ACGTGCCTGA TGGCTACAAG
1141 GCCACAAGAA CCACACAGGA GGACTTCTTT
     CTGCTGCTGG AGCTGGCCTC CCCATCTCAG
1201 ACCTCTCTGT ATTTCTGCGC AAGCTCCGAT
     GCAGGCGTGA GCCAGAACAC ACTGTACTTT
1261 GGAGCAGGAA CCAGGCTGAG CGTGCTGGAG
     GACCTGCGCA ATGTGACACC CCCTAAGGTG
```

-continued

```
1321 AGCCTGTTCG AGCCCTCCAA GGCCGAGATC
     GCCAACAAGA GGAAGGCCAC CCTGGTGTGC
1381 CTGGCAAGGG GCTTCTTTCC TGATCACGTG
     GAGCTGAGCT GGTGGGTGAA TGGCAAGGAG
1441 GTGCACTCCG GCGTGTCTAC AGACCCACAG
     GCCTATAAGG AGAGCAACTA TTCCTACTGC
1501 CTGTCTAGCC GGCTGAGAGT GTCCGCCACC
     TTTTGGCACA ACCCAAGGAA TCACTTCCGC
1561 TGTCAGGTGC AGTTTCACGG CCTGAGCGAG
     GAGGATAAGT GGCCAGAGGG CTCCCCAAAG
1621 CCTGTGACCC AGAATATCTC TGCCGAGGCA
     TGGGGAAGGG CAGACTGTGG AATCACAAGC
1681 GCCTCCTACC AGCAGGGCGT GCTGTCCGCC
     ACCATCCTGT ATGAGATCCT GCTGGGCAAG
1741 GCCACACTGT ACGCCGTGCT GGTGTCCACC
     CTGGTGGTCA TGGCCATGGT GAAGCGCAAG
1801 AACTCTTGA
```

Another embodiment provides a designed mTCR-8 (α is underlined, P2A is bolded, and β is double underlined) having at least 90%, 95%, 99%, or 100% sequence identity to (SEQ ID NO:67):

```
  1 ATGAAGTCCT TCTCTATCAG CCTGGTGGTG
    CTGTGGCTGC AGCTGAACTG GGTGAATTCT
 61 CAGCAGAAGG TGCAGCAGTC CCCTGAGTCT
    CTGATCGTGC AGAGGGCGG CATGGCCTCC
121 CTGAACTGCA CCAGCTCCGA CCGGAATGTG
    GATTATTTTT GGTGGTACAG ACAGCACAGC
181 GGCAAGTCCC CCAAGATGCT GATGTCTATC
    TTCAGCAACG GCGAGAAGGA GGAGGGCCGG
241 TTTACAGTGC ACCTGAATAA GGCCTCCCTG
    CACACCTCTC TGCACATCAG AGACAGCCAG
301 CCTTCCGATT CTGCCCTGTA TCTGTGCGCA
    GCAAGCATCT CCGGAGGATA CAAGGTGGTG
361 TTCGGCAGCG GAACAAGGCT GCTGGTGTCC
    CCCGATATCC AGAATCCAGA GCCCGCCGTG
421 TATCAGCTGA AGGACCCTCG CTCCCAGGAT
    AGCACCCTGT GCCTGTTCAC CGACTTTGAT
481 TCCCAGATCA ACGTGCCAAA GACCATGGAG
    TCTGGCACCT TTATCACAGA CAAGACCGTG
541 CTGGATATGA AGGCCATGGA CTCTAAGAGC
    AACGGCGCCA TCGCCTGGAG CAATCAGACA
```

```
601 TCCTTCACCT GCCAGGATAT CTTTAAGGAG
    ACAAATGCCA CCTACCCATC TAGCGACGTG
661 CCCTGTGATG CCACCCTGAC AGAGAAGTCT
    TTCGAGACCG ACATGAACCT GAATTTTCAG
721 AACCTGAGCG TGATGGGCCT GAGAATCCTG
    CTGCTGAAGG TGGCCGGCTT CAATCTGCTG
781 ATGACACTGA GGCTGTGGTC CTCTGGCTCC
    AGGGCAAAGC GGAGCGGCTC TGGAGCCACC
841 AACTTCTCTC TGCTGAAGCA GGCAGGCGAC
    GTGGAGGAGA ATCCTGGACC ACGGATGGGC
901 TCTAGACTGT TTCTGGTGCT GAGCCTGCTG
    TGCACAAAGC ACATGGAGGC AGCAGTGACC
961 CAGAGCCCAC GGAACAAGGT GACCGTGACA
    GGCGGCAATG TGACACTGTC CTGTAGACAG
1021 ACCAACTCTC ACAATTACAT GTATTGGTAC
     CGGCAGGATA CCGGCCACGG CCTGAGACTG
1081 ATCCACTATT CCTACGGAGC AGGAAACCTG
     CAGATCGGCG ACGTGCCTGA TGGCTACAAG
1141 GCCACAAGGA CCACACAGGA GGACTTCTTT
     CTGCTGCTGG AGCTGGCCAG CCCATCCCAG
1201 ACCAGCCTGT ATTTCTGCGC CAGCTCCGAT
     GCCGGCACAT CCCAGAACAC CCTGTACTTT
1261 GGAGCAGGAA CAAGGCTGAG CGTGCTGGAG
     GACCTGCGCA ATGTGACCCC CCCTAAGGTG
1321 TCTCTGTTCG AGCCCAGCAA GGCCGAGATC
     GCCAACAAGA GGAAGGCCAC CCTGGTGTGC
1381 CTGGCAAGGG GCTTCTTTCC TGATCACGTG
     GAGCTGAGCT GGTGGGTGAA TGGCAAGGAG
1441 GTGCACAGCG GCGTGTCCAC AGACCCACAG
     GCCTATAAGG AGTCTAACTA TAGCTACTGC
1501 CTGTCTAGCC GGCTGAGAGT GTCCGCCACC
     TTTTGGCACA ACCCAAGGAA TCACTTCCGC
1561 TGTCAGGTGC AGTTTCACGG CCTGTCCGAG
     GAGGATAAGT GGCCAGAGGG CTCTCCAAAG
1621 CCTGTGACCC AGAATATCAG CGCCGAGGCA
     TGGGGAAGGG CAGACTGTGG CATCACATCT
1681 GCCAGCTACC AGCAGGGCGT GCTGTCCGCC
     ACCATCCTGT ATGAGATCCT GCTGGGCAAG
```

-continued

```
1741 GCCACACTGT ACGCCGTGCC GGTGAGCACC
     CTGGTGGTCA TGGCCATGGT GAAGAGAAAG
1801 AACTCCTGA
```

Another embodiment provides a designed mTCR-10 (α is underlined, P2A is bolded, and p is double underlined) having at least 90%, 95%, 99%, or 100% sequence identity to (SEQ ID NO:68):

```
   1 ATGAAGTCCT TCTCTATCAG CCTGGTGGTG
     CTGTGGCTGC AGCTGAACTG GGTGAATAGC
  61 CAGCAGAAGG TGCAGCAGTC TCCTGAGAGC
     CTGATCGTGC CAGAGGGCGG CATGGCCTCC
 121 CTGAACTGCA CCAGCTCCGA CCGGAATGTG
     GATTATTTTT GGTGGTACAG ACAGCACTCC
 181 GGCAAGTCTC CCAAGATGCT GATGAGCATC
     TTCTCCAACG CGAGAAGGA GGAGGGCCGG
 241 TTTACAGTGC ACCTGAATAA GGCCTCTCTG
     CACACCAGCC TGCACATCAG AGACTCCCAG
 301 CCTTCCGATT CTGCCCTGTA TCTGTGCGCC
     GCCTCTATCG TGGGCGGCTA CAAGGTGGTG
 361 TTCGGCTCCG GCACAAGGCT GCTGGTGTCT
     CCCGATATCC AGAATCCAGA GCCCGCCGTG
 421 TATCAGCTGA AGGACCCTCG CTCTCAGGAT
     AGCACCCTGT GCCTGTTCAC CGACTTTGAT
 481 TCTCAGATCA ACGTGCCAAA GACCATGGAG
     AGCGGCACCT TTATCACAGA CAAGACCGTG
 541 CTGGATATGA AGGCCATGGA CAGCAAGTCC
     AACGGCGCCA TCGCCTGGTC CAATCAGACA
 601 TCTTTCACCT GCCAGGATAT CTTTAAGGAG
     ACAAATGCCA CCTACCCATC TAGCGACGTG
 661 CCCTGTGATG CCACCCTGAC AGAAGAGAGC
     TTCGAGACCG ACATGAACCT GAATTTTCAG
 721 AACCTGTCCG TGATGGGCCT GAGAATCCTG
     CTGCTGAAGG TGGCCGGCTT CAATCTGCTG
 781 ATGACACTGC GCCTGTGGTC CTCTGGCTCT
     AGGGCAAAGC GGAGCGGCAG CGGAGCAACC
 841 AACTTCAGCC TGCTGAAGCA GGCAGGCGAC
     GTGGAGGAGA ATCCTGGACC ACGGATGGGC
 901 AGCAGACTGT TCTCGGTGCT GTCCCTGCTG
     TGCACAAAGC ACATGGAGGC AGCAGTGACC
 961 CAGAGCCCAC GGAACAAGGT GACCGTGACA
     GGCGGCAATG TGACACTGTC TTGTAGACAG
1021 ACCAACAGCC ACAATTACAT GTATTGGTAC
     CGGCAGGATA CCGGCCACGG CCTGAGACTG
1081 ATCCACTATT CCTACGGAGC AGGAAACCTG
     CAGATCGGCG ACGTGCCTGA TGGCTACAAG
1141 GCCACAAGGA CCACACAGGA GGACTTCTTT
     CTGCTGCTGG AGCTGGCCTC CCCATCTCAG
1201 ACCAGCCTGT ATTTCTGCGC CAGCTCCGAT
     CACGGCACAG GCCAGAACAC CCTGTACTTT
1261 GGAGCAGGAA CAAGGCTGTC CGTGCTGGAG
     GACCTGCGCA ATGTGACCCC CCCTAAGGTG
1321 AGCCTGTTCG AGCCCTCCAA GGCCGAGATC
     GCCAACAAGA GGAAGGCCAC CCTGGTGTGC
1381 CTGGCAAGGG GCTTCTTTCC TGATCACGTG
     GAGCTGAGCT GGTGGGTGAA TGGCAAGGAG
1441 GTGCACTCCG GCGTGTCTAC AGACCCCACG
     GCCTATAAGG AGAGCAACTA TTCCTACTGC
1501 CTGTCTAGCC GGCTGAGAGT GTCCGCCACC
     TTTTGGCACA ACCCAAGGAA TCACTTCCGC
1561 TGTCAGGTGC AGTTTCACGG CCTGTCTGAG
     GAGGATAAGT GGCCAGAGGG CAGCCCAAAG
1621 CCTGTGACCC AGAATATCTC CGCCGAGGCA
     TGGGGAAGGG CAGACTGTGG AATCACAAGC
1681 GCCTCCTACC AGCAGGGCGT GCTGAGCGCC
     ACCATCCTGT ATGAGATCCT GCTGGGCAAG
1741 GCCACACTGT ACGCCGTGCT GGTGTCCACC
     CTGGTGGTCA TGGCCATGGT GAAGAGAAAG
1801 AACTCTTGA
```

Another embodiment provides a designed mTCR-11 (α is underlined, P2A is bolded, and μ is double underlined) having at least 90%, 95%, 99%, or 100% sequence identity to (SEQ ID NO:69):

```
   1 ATGAAGTCCT TCTCTATCAG CCTGGTGGTG
     CTGTGGCTGC AGCTGAACTG GGTGAATAGC
  61 CAGCAGAAGG TGCAGCAGTC TCCTGAGAGC
     CTGATCGTGC CAGAGGGCGG CATGGCCTCC
 121 CTGAACTGCA CCAGCTCCGA CCGGAATGTG
     GATTATTTTT GGTGGTACAG ACAGCACTCC
 181 GGCAAGTCTC CCAAGATGCT GATGAGCATC
     TTCTCCAACG CGAGAAGGA GGAGGGCCGG
 241 TTTACAGTGC ACCTGAATAA GGCCTCTCTG
     CACACCAGCC TGCACATCAG AGACAGCCAG
```

-continued

```
 301 CCTTCCGATT CTGCCCTGTA TCTGTGCGCC
     GCCTCCAAGA CAGGCGGCTA CAAGGTGGTG
 361 TTCGGCTCCG GAACCAGGCT GCTGGTGTCT
     CCCGATATCC AGAATCCAGA GCCCGCCGTG
 421 TATCAGCTGA AGGACCCTCG CTCTCAGGAT
     AGCACCCTGT GCCTGTTCAC CGACTTTGAT
 481 TCTCAGATCA ACGTGCCAAA GACAATGGAG
     AGCGGCACCT TTATCACAGA CAAGACCGTG
 541 CTGGATATGA AGGCCATGGA CAGCAAGTCC
     AACGCGCCA TCGCCTGGTC CAATCAGACA
 601 TCTTTCACCT GCCAGGATAT CTTTAAGGAG
     ACAAATGCCA CCTACCCATC TAGCGACGTG
 661 CCCTGTGATG CCACCCTGAC AGAGAAGTCT
     TTCGAGACCG ACATGAACCT GAATTTTCAG
 721 AACCTGAGCG TGATGGGCCT GAGAATCCTG
     CTGCTGAAGG TGGCCGGCTT CAATCTGCTG
 781 ATGACACTGA GGCTGTGGTC CTCTGGCTCC
     AGGGCAAAGC GGAGCGGCAG CGGAGCAACC
 841 AACTTCTCTC TGCTGAAGCA GGCAGGCGAC
     GTGGAGGAGA ATCCTGGACC ACGGATGGGC
 901 AGCAGACTGT TCTGGTGCT GTCCCTGCTG
     TGCACAAAGC ACATGGAGGC AGCAGTGACC
 961 CAGAGCCCAC GGAACAAGGT GACCGTGACA
     GGCGGCAATG TGACACTGTC TTGTAGACAG
1021 ACCAACAGCC ACAATTACAT GTATTGGTAC
     CGGCAGGATA CCGGCCACGG CCTGAGACTG
1081 ATCCACTATT CCTACGGAGC AGGAAACCTG
     CAGATCGGCG ACGTGCCTGA TGGCTACAAG
1141 GCCACAAGGA CCACACAGGA GGACTTCTTT
     CTGCTGCTGG AGCTGGCCTC CCCATCTCAG
1201 ACCTCCCTGT ATTTCTGCGC CAGCTCCGAT
     GCCGGCACAT CTCAGAACAC CCTGTACTTT
1261 GGAGCAGGAA CAAGGCTGAG CGTGCTGGAG
     GACCTGCGCA ATGTGACCCC CCTAAGGTG
1321 AGCCTGTTCG AGCCCTCCAA GGCCGAGATC
     GCCAACAAGA GGAAGGCCAC CCTGGTGTGC
1381 CTGGCAAGGG GCTTCTTTCC TGATCACGTG
     GAGCTGAGCT GGTGGGTGAA TGGCAAGGAG
1441 GTGCACTCCG GCGTGTCTAC AGACCCACAG
     GCCTATAAGG AGAGCAACTA TTCCTACTGC
```

-continued

```
1501 CTGTCTAGCC GGCTGAGAGT GTCCGCCACC
     TTTTGGCACA ACCCAAGGAA TCACTTCCGC
1561 TGTCAGGTGC AGTTTCACGG CCTGTCTGAG
     GAGGATAAGT GGCCAGAGGG CAGCCCAAAG
1621 CCTGTGACCC AGAATATCTC CGCCGAGGCA
     TGGGGAAGGG CAGACTGTGG AATCACAAGC
1681 GCCTCCTACC AGCAGGGCGT GCTGAGCGCC
     ACCATCCTGT ATGAGATCCT GCTGGGCAAG
1741 GCCACACTGT ACGCCGTGCT GGTGAGCACC
     CTGGTGGTCA TGGCCATGGT GAAGAGAAAG
1801 AACTCCTGA
```

One embodiment provides a designed mTCR-17 (α is underlined, P2A is bolded, and β is double underlined) having at least 90%, 95%, 99%, or 100% sequence identity to (SEQ ID NO:70):

```
   1 ATGAAATCCT TTAGTATTTC CCTAGTGGTC
     CTGTGGCTTC AGCTAAACTG GGTGAACAGC
  61 CAACAGAAGG TGCAGCAGAG CCCAGAATCC
     CTCATTGTTC AGAGGGAGG CATGGCCTCT
 121 CTCAACTGCA CTTCCAGTGA TCGTAATGTT
     GACTACTTCT GGTGGTACAG ACAGCACTCT
 181 GGGAAAAGCC CCAAGATGCT GATGTCTATC
     TTCTCCAATG GTGAAAAGGA AGAAGGCAGA
 241 TTCACAGTTC ACCTCAATAA AGCCAGCCTG
     CATACTTCCC TGCACATCAG AGACTCCCAG
 301 CCCAGTGACT CTGCTCTCTA CCTCTGTGCA
     GCAAGCATGA CTGGAGGCTA TAAAGTGGTC
 361 TTTGGAAGTG GGACTCGATT GCTGGTAAGC
     CCTGACATCC AGAACCCAGA ACCTGCTGTG
 421 TACCAGTTAA AAGATCCTCG GTCTCAGGAC
     AGCACCCTCT GCCTGTTCAC CGACTTTGAC
 481 TCCCAAATCA ATGTGCCGAA AACCATGGAA
     TCTGGAACGT TCATCACTGA CAAAACTGTG
 541 CTGGACATGA AAGCTATGGA TTCCAAGAGC
     AATGGGGCCA TTGCCTGGAG CAACCAGACA
 601 AGCTTCACCT GCCAAGATAT CTTCAAAGAG
     ACCAACGCCA CCTACCCCAG TTCAGACGTT
 661 CCCTGTGATG CCACGTTGAC TGAGAAAAGC
     TTTGAAACAG ATATGAACCT AAACTTTCAA
```

```
 721 AACCTGTCAG TTATGGGACT CCGAATCCTC
     CTGCTGAAAG TAGCCGGATT TAACCTGCTC
 781 ATGACGCTGA GGCTGTGGTC CAGTGGCAGC
     AGAGCCAAGA GAAGCGGATC CGGCGCCACC
 841 AACTTCAGCC TGCTGAAGCA GGCCGGCGAC
     GTGGAGGAAA ACCCTGGCCC TAGGATGGGC
 901 TCCAGGCTCT TTCTGGTCTT GAGCCTCCTG
     TGTACAAAAC ACATGGAGGC TGCAGTCACC
 961 CAAAGCCCTA GAAACAAGGT GACAGTAACA
     GGAGGAAACG TGACATTGAG CTGTCGCCAG
1021 ACTAATAGCC ACAACTACAT GTACTGGTAT
     CGGCAGGACA CTGGGCATGG GCTGAGGCTG
1081 ATCCATTACT CATATGGTGC TGGCAACCTT
     CAAATAGGAG ATGTCCCTGA TGGGTACAAG
1141 GCCACCGAAA CAACGCAAGA AGACTTCTTC
     CTCCTGCTGG AATTGGCTTC TCCCTCTCAG
1201 ACATCTTTGT ACTTCTGTGC CAGCAGTGAT
     GCAGGGACAA GTCAAACAC CTTGTACTTT
1261 GGTGCGGGCA CCCGACTATC GGTGCTAGAG
     GATCTGAGAA ATGTGACTCC ACCCAAGGTC
1321 TCCTTGTTTG AGCCATCAAA AGCAGAGATT
     GCAAACAAAC GAAAGGCTAC CCTCGTGTGC
1381 TTGGCCAGGG GCTTCTTCCC TGACCACGTG
     GAGCTGAGCT GGTGGGTGAA TGGCAAGGAG
1441 GTCCACAGTG GGGTCAGCAC GGACCCTCAG
     GCCTACAAGG AGAGCAATTA TAGCTACTGC
1501 CTGAGCAGCC GCCTGAGGGT CTCTGCTACC
     TTCTGGCACA ATCCTCGAAA CCACTTCCGC
1561 TGCCAAGTGC AGTTCCATGG GCTTTCAGAG
     GAGGACAGT GGCCAGAGGG CTCACCCAAA
1621 CCTGTCACAC AGAACATCAG TGCAGAGGCC
     TGGGGCCGAG CAGACTGTGG GATTACCTCA
1681 GCATCCTATC AACAAGGGGC CTTGTCTGCC
     ACCATCCTCT ATGAGATCCT GCTAGGGAAA
1741 GCCACCCTGT ATGCTGTGCT TGTCAGTACA
     CTGGTGGTGA TGGCTATGGT CAAAAGAAAG
1801 AATTCATGA
```

Another embodiment provides a designed mTCR-38 (α is underlined, P2A is bolded, and β is double underlined) having at least 90%, 95%, 99%, or 100% sequence identity to (SEQ ID NO:71):

```
   1 ATGAAATCCT TTAGTATTTC CCTAGTGGTC
     CTGTGGCTTC AGCTAAACTG GGTGAACAGC
  61 CAACAGAAGG TGCAGCAGAG CCCAGAATCC
     CTCATTGTTC AGAGGGAGG CATGGCCTCT
 121 CTCAACTGCA CTTCCAGTGA TCGTAATGTT
     GACTACTTCT GGTGGTACAG ACAGCACTCT
 181 GGGAAAAGCC CCAAGATGCT GATGTCTATC
     TTCTCCAATG GTGAAAAGGA AGAAGGCAGA
 241 TTCACAGTTC ACCTCAATAA AGCCAGCCTG
     CATACTTCCC TGCACATCAG AGACTCCCAG
 301 CCCAGTGACT CTGCTCTCTA CCTCTGTGCA
     GCAACCCTGA CTGGAGGCTA TAAAGTGGTC
 361 TTTGGAAGTG GGACTCGATT GCTGGTAAGC
     CCTGACATCC AGAACCCAGA ACCTGCTGTG
 421 TACCAGTTAA AAGATCCTCG GTCTCAGGAC
     AGCACCCTCT GCCTGTTCAC CGACTTTGAC
 481 TCCCAAATCA ATGTGCCGAA AACCATGGAA
     TCTGGAACGT TCATCACTGA CAAAACTGTG
 541 CTGGACATGA AAGCTATGGA TTCCAAGAGC
     AATGGGGCCA TTGCCTGGAG CAACCAGACA
 601 AGCTTCACCT GCCAAGATAT CTTCAAAGAG
     ACCAACGCCA CCTACCCCAG TTCAGACGTT
 661 CCCTGTGATG CCACGTTGAC TGAGAAAAGC
     TTTGAAACAG ATATGAACCT AAACTTTCAA
 721 AACCTGTCAG TTATGGGACT CCGAATCCTC
     CTGCTGAAAG TAGCCGGATT TAACCTGCTC
 781 ATGACGCTGA GGCTGTGGTC CAGTGGCAGC
     AGAGCCAAGA GAAGCGGATC CGGCGCCACC
 841 AACTTCAGCC TGCTGAAGCA GGCCGGCGAC
     GTGGAGGAAA ACCCTGGCCC TAGGATGGGC
 901 TCCAGGCTCT TTCTGGTCTT GAGCCTCCTG
     TGTACAAAAC ACATGGAGGC TGCAGTCACC
 961 CAAAGCCCTA GAAACAAGGT GACAGTAACA
     GGAGGAAACG TGACATTGAG CTGTCGCCAG
1021 ACTAATAGCC ACAACTACAT GTACTGGTAT
     CGGCAGGACA CTGGGCATGG GCTGAGGCTG
1081 ATCCATTACT CATATGGTGC TGGCAACCTT
     CAAATAGGAG ATGTCCCTGA TGGGTACAAG
```

-continued

```
1141 GCCACCAGAA CAACGCAAGA AGACTTCTTC

CTCCTGCTGG AATTGGCTTC TCCCTCTCAG

1201 ACATCTTTGT ACTTCTGTGC CAGCAGTGAT

GCTGGGACTA GTCAAAACAC CTTGTACTTT

1261 GGTGCGGGCA CCCGACTATC GGTGCTAGAG

GATCTGAAGA ATGTGACTCC ACCCAAGGTC

1321 TCCTTGTTTG AGCCATCAAA AGCAGAGATT

GCAAACAAAC GAAAGGCTAC CCTCGTGTGC

1381 TTGGCCAGGG GCTTCTTCCC TGACCACGTG

GAGCTGAGCT GGTGGGTGAA TGGCAAGGAG

1441 GTCCACAGTG GGGTCAGCAC GGACCCTCAG

GCCTACAAGG AGAGCAATTA TAGCTACTGC

1501 CTGAGCAGCC GCCTGAGGGT CTCTGCTACC

TTCTGGCACA ATCCTCGAAA CCACTTCCGC

1561 TGCCAAGTGC AGTTCCATGG GCTTTCAGAG

GAGGACAAGT GGCCAGAGGG CTCACCCAAA

1621 CCTGTCACAC AGAACATCAG TGCAGAGGCC

TGGGGCCGAG CAGACTGTGG GATTACCTCA

1681 GCATCCTATC AACAAGGGGT CTTTGTCTGCC

ACCATCCTCT ATGAGATCCT GCTAGGGAAA

1741 GCCACCCTGT ATGCTGTGCT TGTCAGTACA

CTGGTGGTGA TGGCTATGGT CAAAAGAAAG

1801 AATTCATGA
```

B. Genetically Engineered T Cells

Another embodiment provides genetically engineered CD8+ immune cells that express the disclosed mouse TCR genes to produce a TCR that specifically binds to hAFP or a fragment thereof expressed on the surface of a tumor cell. Preferably, the immune cells are human T cells, for example human cytotoxic T cells. The engineered human cytotoxic T cells can be autologous human cytotoxic T cells. TCR genes can be codon optimized.

Another embodiment provides CD4+ immune cells, preferably human CD4+ immune cells, genetically engineered to express the disclosed mouse TCR genes. CD4+ cells include T helper cells, monocytes, macrophages, and dendritic cells. The engineered human CD4+ immune cells can be autologous human T helper cells. The TCR genes can be codon optimized.

The 9 hAFP$_{158}$ specific murine TCRs identified in this study are able to render CD4 T cells the capability of binding Tet$_{158}$ tetramer, suggesting that they are high affinity and independent of CD8 help. The role of CD4 in adoptive cell therapy is not clear. But the production of IL-2 by CD4 TCR-T cells in response to HepG2 tumor cells stimulation may provide the cytokine for maintaining T cell proliferation. In addition, the CD4 TCR-T cells demonstrate a low cytotoxicity against HepG2 tumor cells. Thus, although the CD8 TCR-T may be the major player for killing hAFP+ tumor cells, the CD4 TCR-T can provide the help for T cell proliferation, which can be critical for generating antitumor effect in vivo.

It is believed that murine TCRs may provide increased expression on the surface of a human host cell as compared to human TCR. Murine TCRs can also replace endogenous TCRs on the surface of the human host cell more effectively than exogenous human TCR. However, humanization of the mTCR may be necessary to avoid anti-TCR responses with repeated use of TCR-T cells. Methods of humanizing mTCRs are known in the arts. See for example U.S. Pat. Nos. 5,861,155, and 5,859,205, WO2007/131092, EP0460167 and Davis, et al., Clin Cancer Res., 16:5852-5861 (2010), which are incorporated by reference in their entirety. In one embodiment, the disclosed mTCR genes are humanized before being introduced to a T cell or administered to a human subject.

C. T Cell Hybridomas

Another embodiment provides T cell hybridomas that express the disclosed mTCR polypeptides. For example, the hybridoma can be a result of the fusion of fusing sorted mouse CD8+Tet$_{158}$+ cells with BW-Lyt2.4 cells that lack TCR α and β chains and are selected as described (He., Y. et al., *J Immunol*, 174:3808-3817 (2005)). Methods of making the hybridomas are provided in the Examples.

D. Antibodies

One embodiment provides antibodies that specifically bind the disclosed mTCR proteins, for example SEQ ID NO:2-62. Suitable antibodies can be prepared by one of skill in the art. The antibody or antigen binding fragment therefore, can be an agonist or antagonist of mTCR or simply binds specifically to the mTCR or a polypeptide thereof.

In some embodiments, the disclosed antibodies and antigen binding fragments thereof immunospecifically bind to mTCR or a polypeptide thereof (e.g., any one of SEQ ID NO:2-62). In some embodiments, the antibody binds to an extracellular domain of an mTCR (SEQ ID NOs:41-53).

For example, molecules are provided that can immunospecifically bind to the disclosed mTCR polypeptides:

(I) arrayed on the surface of a cell (especially a live cell); or (II) arrayed on the surface of a cell (especially a live cell) at an endogenous concentration;

Compositions are also provided that can immunospecifically bind to soluble endogenous mTCR polypeptides. In some embodiments the molecules reduce or prevent the soluble mTCR polypeptide from binding or otherwise interacting with its ligand.

The antibodies or antigen binding fragments thereof can be prepared using any suitable methods known in the art such as those discussed in more detail below.

1. Human and Humanized Antibodies

The antibodies that specifically bind to the disclosed mTCR polypeptides can be human or humanized. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

2. Single-Chain Antibodies

The antibodies that specifically bind the disclosed mTCR polypeptides can be single-chain antibodies. Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

3. Monovalent Antibodies

The antibodies that specifically bind to the disclosed mTCR polypeptides can be monovalent antibodies. In vitro methods can be used for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

4. Hybrid Antibodies

The antibodies that specifically bind the disclosed mTCR polypeptides can be hybrid antibodies. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

5. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

The disclosed antibodies and mTCR polypeptides can be conjugated or linked to one or more detectable labels. The disclosed antibodies and mTCR polypeptides can be linked to at least one agent to form a detection conjugate. In order to increase the efficacy of the molecules as diagnostic it is conventional to link or covalently bind or complex at least one desired molecule or moiety. Such a molecule or moiety may be, but is not limited to, at least one reporter molecule. A reporter molecule is defined as any moiety that may be detected using an assay. Non-limiting examples of reporter molecules that have been conjugated to antibodies or polypeptides include enzymes, radiolabels, haptens, fluorescent labels, phosphorescent molecules, chemiluminescent molecules, chromophores, luminescent molecules, photoaffinity molecules, colored particles and/or ligands, such as biotin.

E. Formulations

The disclosed antibodies, fusion proteins, and mTCR polypeptides can be formulated into pharmaceutical compositions. Pharmaceutical compositions containing the antibody, fusion protein, or mTCR polypeptides can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the disclosed compositions are administered locally, for example by injection directly into a site to be treated. Typically, the injection causes an increased localized concentration of the composition which is greater than that which can be achieved by systemic administration. The compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89.

Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. *Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunem, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™ cellulose acetate phthalate (CAP), Eudragit L™, Eudragit S™, and Shellac™. These coatings may be used as mixed films.

3. Formulations for Topical Administration

The disclosed immunomodulatory agents can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The fusion proteins, mTCR polypeptides, and antibodies disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides, antibodies, or mTCR polyepeptidesor nucleic acids encoding them, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Use

In certain embodiments, the disclosed antibodies, mTCR polypeptides and engineered immune cells can be used to detect or treat cancer. A preferred cancer to be detected, diagnosed, or treated includes heptacellular carcinoma or any other cancer the expresses hAFP.

A. Adoptive Transfer

In one embodiment, immune cells are engineered to express the disclosed mTCR. The immune cells are T cells, preferably human T cells. The cells can be autologous or heterologous. The cells are typically transduced in vitro. The transduced cells can optionally be expanded in vitro to obtain a large population transduced cells that can administered to a subject in need thereof. Such subjects typically have or are believed to have a cancer or tumor that expresses hAFP. The T cells can be CD8+ or CD4+. The transduced cells can be administered in one or more doses to the subject.

The adoptive transfer can be combined with other therapies for the treatment of cancer. Such additional therapies include chemotherapy, radiation therapy, and surgery or a combination thereof. The adoptive transfer of TCR-T can be combined with cancer vaccines so that the TCR-T will be further expanded in vivo to reduce the number of transferred TCR-T cells and the associated toxicity.

One embodiment provides a method for reducing tumor burden in a subject in need thereof by administering engineered T cells that express one of the disclosed mTCRs, wherein the engineered mTCR cells inhibit or reduce tumors that express hAFP. The subject can optionally be treated with a cotherapy for cancer. A preferred cancer to be treated is heptacellular carcinoma.

B. Detection or Diagnosis

The disclosed antibodies or mTCR polypeptides can be labeled as discussed above. The labeled polypeptides can be applied to a sample of cancer cells wherein the specific binding of the labeled polypeptides to the sample of cancer cells is indicative of a hAFP specific cancer including heptacellular carcinoma.

The detection of the label can optionally be quantified to determine the number of cancer cells in sample. The sample is typically a liver tissue sample but can include a blood or serum sample.

IV. Compositions and Kits

Also provided are compositions and kits. Such kits can include containers, each with one or more of the various reagents (typically in concentrated form) utilized in the methods, including, for example, one or more binding agents (antibodies), already attached to a marker or optionally with reagents for coupling a binding agent to an antibody (as well as the marker itself), buffers, and/or reagents and instrumentation for the isolation (optionally by microdissection) to support the practice of the invention. A label or indicator describing, or a set of instructions for use of, kit components in a ligand detection method of the present invention, will also be typically included, where the instructions may be associated with a package insert and/or the packaging of the kit or the components thereof.

Additional embodiments provide immunodetection kits for use with the immunodetection methods described herein. As the antibodies or mTCR polypeptides are generally used to detect hAFP, the antibodies and mTCR polypeptides will generally be included in the kit. The immunodetection kits will thus comprise, in suitable container means, a first antibody that binds to an mTCR polypeptide and/or optionally, an immunodetection reagent.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted herein, a number of exemplary labels are known in the art and/or all such labels may be suitably employed in connection with the present invention.

The kits may further comprise a therapeutic agent for the treatment of cancer, such as an an engineered immune cell expressing the disclosed mTCR polypeptides.

EXAMPLES

Example 1: Immunization of AAD Mice with Lv-Prime and Peptide-Boost Elicits High Level of hAFP158-Specific CD8 T Cells that can Recognize and Kill Human HepG2 Tumor Cells Materials and Methods Mice: HLA-A2 transgenic AAD mice (Pichard, V., et al, J Immunother, 31:246-253 (2008)) and NSG mice were purchased from Jackson Laboratory and housed in specific pathogen-free animal facility. Animal protocols were approved by the Institutional Animal Care and Use Committee of Augusta University.

Immunization: Mice were immunized with recombinant lentivector (lv) expressing hAFP or influenza virus M1 protein subcutaneously as described (Morgan, R A. et al., J Immunother, 36:133-151 (2013)). Twelve days later, mice were boosted with $hAFP_{158}$ (FMNKFIYEI) (SEQ ID NO:1) or $M_{158}$ (GILGFVFTL)(SEQ ID NO:72) peptide together with PolyI:C and anti-CD40 antibody as described (Linette, G. P., et al., Blood, 122:863-871 (2013)).

Results

To induce mouse CD8 T cells capable of recognizing human HLA-A2 presented hAFP epitopes, the HLA-A2 transgenic AAD mice were immunized with recombinant hAFP-lv. The AAD mice express a chimeric MHC I molecule of human HLA-A2 α1-α2 domain and the mouse H-2d α3 domain that bind mouse CD8 molecule to help immune priming (Pichard, V., et al, *J Immunother,* 31:246-253 (2008)). It was found that hAFP-lv immunization reproducibly induced a modest level of hAFP$_{158}$ epitope-specific CD8 responses in AAD mice (FIG. 1A-1E). However, detect CD8 responses were not detected against other 3 hAFP epitopes (hAFP$_{137}$, hAFP$_{325}$, and hAFP$_{542}$) previously identified in human (Vora, S. R., et al., *Oncologist,* 14:717-725 (2009)) (data not shown). Immunization with hAFP158 peptide alone did not induce measurable CD8 responses. But boost immunization with hAFP$_{158}$ epitope markedly increased the magnitude of hAFP$_{158}$-specific CD8 responses in the hAFP-lv primed, but not in the hAFP158 peptide primed, mice (FIGS. 1AF-1E). Critically, the mouse CD8 T cells from the immunized mice could produce IFNγ after co-culture with the hAFP+, but not the hAFP−, HepG2 tumor cells (FIG. 1F-1I). This data suggest that the hAFP vaccine-activated mouse CD8 T cells could recognize and respond to hAFP+HepG2 tumor cells. In addition, after overnight co-culture with splenocytes from the immunized mice, the hAFP+HepG2 tumor cells were killed in a dose dependent manner (FIGS. 1J-1M). Together these data suggest that immunization of AAD mice with hAFP-lv prime and hAFP$_{158}$ peptide boost can elicit high level of hAFP$_{158}$-specific CD8 T cells that can recognize and kill hAFP+ human HepG2 tumor cells.

Example 2: Adoptive Transfer of Splenocytes of the AAD Mice Immunized with hAFP-Lv and hAFP158 not Only Prevents, but Also Eradicates Large HepG2 Tumor Xenografts in NSG Mice Materials and Methods Fifteen million total splenocytes (1.5 million of hAFP$_{158}$-specific CD8 T cells) of the naïve or immunized mice were injected into NSG mice, which were then challenged with HepG2 tumor cells. In the therapeutic model, NSG mice were injected with 15 million total splenocytes of the immunized mice when tumor size reaches 2 cm in diameter. The experiment was done twice with similar data.
Results In this adoptive transfer experiment, it was found that the splenocytes from AAD mice immunized with hAFP-lv and hAFP$_{158}$ peptide, but not that from naïve mice, could completely prevent HepG2 tumor cell challenge in NSG mice (FIGS. 2A and 2B). Approximately 10% of the immunized mouse splenocytes produced IFNγ in response to hAFP$_{158}$ peptide. Strikingly adoptive transfer of the splenocytes from the immunized AAD mice could completely eradicate HepG2 tumors as large as 20 mm in diameter (FIG. 2C).

Example 3: Adoptive Transfer of the hAFP$_{158}$-Specific Mouse CD8 T Cells Eradicates Human HepG2 Tumors in NSG Mice Materials and Methods To further identify the immune cells responsible for eradicating the established HepG2 tumor, CD8 T cells from the AAD mice immunized with hAFP-lv and hAFP$_{158}$ peptide were isolated using magnetic CD8 beads (FIG. 3A). The CD8 T cells from the AAD mice immunized with lv expressing influenza virus M1 antigen and M$_{158}$ peptide were also isolated and used as control. Cell lines: HEK293T cells and human liver cancer cell line HepG2 was purchased from ATCC. The HCC cell line of Huh7 (HLA-A11) was a gift of Dr. Ande of Georgia Cancer Center, and the AFP-HepG2 cell was provided by Dr. Jingxiong She of Augusta University. The hAFP expression and HLA type were verified by western blot and immunological staining. Cells were cultured in DMEM media with 10% of FBS.

Immunization: Mice were immunized with recombinant lentivector (lv) expressing hAFP or influenza virus M1 protein subcutaneously as described (Morgan, R A. et al., *J Immunother,* 36:133-151 (2013)). Twelve days later, mice were boosted with hAFP$_{158}$ (FMNKFIYEI)(SEQ ID NO:1) or M158 (GILGFVFTL)(SEQ ID NO:72) peptide together with PolyI:C and anti-CD40 antibody as described (Linette, G. P., et al., *Blood,* 122:863-871 (2013)). Tumor inoculation: Five millions of HepG2 tumor cells were inoculated into the flank of NSG mice. Tumor growth was monitored every other day.
Results It was found that adoptive transfer of CD8 T cells from the hAFP immunized mice could eradicate HepG2 tumors in NSG mice (FIG. 3B). In contrast, the HepG2 tumors continued growing in the NSG mice received the CD8 T cells from the influenza virus M1 antigen immunized mice. Next, the hAFP$_{158}$-specific CD8 T cells were further isolated by Tet$_{158}$ tetramer staining and cell sorting (FIG. 3C). After adoptive transfer, while the Tet$_{158-}$ CD8 T cells did not inhibit HepG2 tumor growth, the Tet$_{158}$+CD8 T cells could eradicate HepG2 tumors in NSG mice (FIG. 3D). Together, the in vitro and in vivo data verify that the mouse CD8 T cells specific for HLA-A2 presented hAFP$_{158}$ epitope can recognize and kill human HCC tumor cells.

Example 4: The T Cell Hybridomas Created from the Tet$_{158+}$ CD8 T Cells Bind to HLA-A2/hAFP$_{158}$ Tetramer and Some Produce IL-2 Response to hAFP+ HepG2 Tumor Cells Materials and Methods T cell hybridoma: T cell hybridomas were created by fusing the sorted mouse CD8+Tet$_{158}$+ cells with BW-Lyt2.4 cells that is lack of TCR α and β chains and selected as described (He, Y., et al., *J Immunol,* 174:3808-3817 (2005)).

Immunological and tetramer staining: Splenocytes were stained with surface marker and anti-Vβ antibody panel (BD Biosciences, San Diego, CA). HLA-A2/hAFP$_{158}$ tetramers (Tet$_{158}$) were kindly provided by NIH Tetramer Core Facility at Emory University.
Results To identify and clone paired TCR α and β chain gene from a single T cells, T cell hybridoma cell lines were established. Prior to generating T cell hybridomas, the TCR Vβ chains were characterized using the anti-Vβ panel antibodies. The data showed that >90% of the Tet$_{158}$+CD8 T cells could be stained with anti-V08.3 antibody (FIG. 11A-B). The other less than 10% of the Tet$_{158}$+CD8 T cells could be stained with antibodies against Vβ2, Vβ5.1/5.2, Vβ4, and Vβ11. Next, a total of 39 T cell hybridoma clones that could be stained by Tet$_{158}$ tetramer were obtained from two cell fusion experiments using sorted Tet$_{158+}$ CD8 T cells (data not shown). Among them, 5 clones could respond to the stimulation of hAFP+HepG2 tumor cells and produce IL-2 (FIG. 4A), while other 34 hybridomas produced no or very low level of IL-2 (data not shown). All hybridomas could be stained by anti-Vβ8.3 antibody (FIG. 4B). Further analysis showed that the T cell hybridomas could bind to Tet$_{158}$ tetramer, but with different mean fluorescent intensity (FIG. 4C), suggesting that their TCR may have different affinity for HLA-A2/hAFP$_{158}$ complex. On the other hand, 4 of the remaining 34 T cell hybridomas consist of Vβ chains that could not be stained with anti-Vβ8.3 antibody (data not shown).

Example 5: Nine Sets of Paired TCR α and β Chain Genes are Identified from 14 T Cell Hybridomas Materials and Methods Identification of the TCRα and β chain genes: Total RNA was isolated from T cell hybridomas. 5-RACE technique (Hong, Y., et al., *Hepatology*, 59:1448-1458 (2014)) was conducted to amplify the TCR α and β chain genes. The cDNA was made with oligo dT primer and then the PolyC was added to the 5 end of cDNA. PCR was conducted by using the 5' pGI primer (CACCGGGIIGGGIIGGGIIGG) (SEQ ID NO:73) and the 3' primers corresponding to the constant (C) region of α chain (GGCATCACAGGGAACG) (SEQ ID NO:74) or β chain (CCAGAAGGTAGCAGA-GACCC) (SEQ ID NO:75). Based on the obtained partial sequence of the TCR α and β variable (V) regions, specific primer corresponding to the V region of α (AT-GAAATCCTTTAGTATTTCCC) (SEQ ID NO:76) or β (ATGGGCTCCAGGCTCTTTCTG) (SEQ ID NO:77) chains were used together with the internal primer of α C-region (GCACATTGATTTGGGAGTC) (SEQ ID NO:78) or β C-region: (GGGTAGCCTTTTGTTTGTTTG) (SEQ ID NO:79) to amplify and verify the V region. Finally, sequences of the TCR α and β chains were obtained and verified.

Results

Figure 16A:
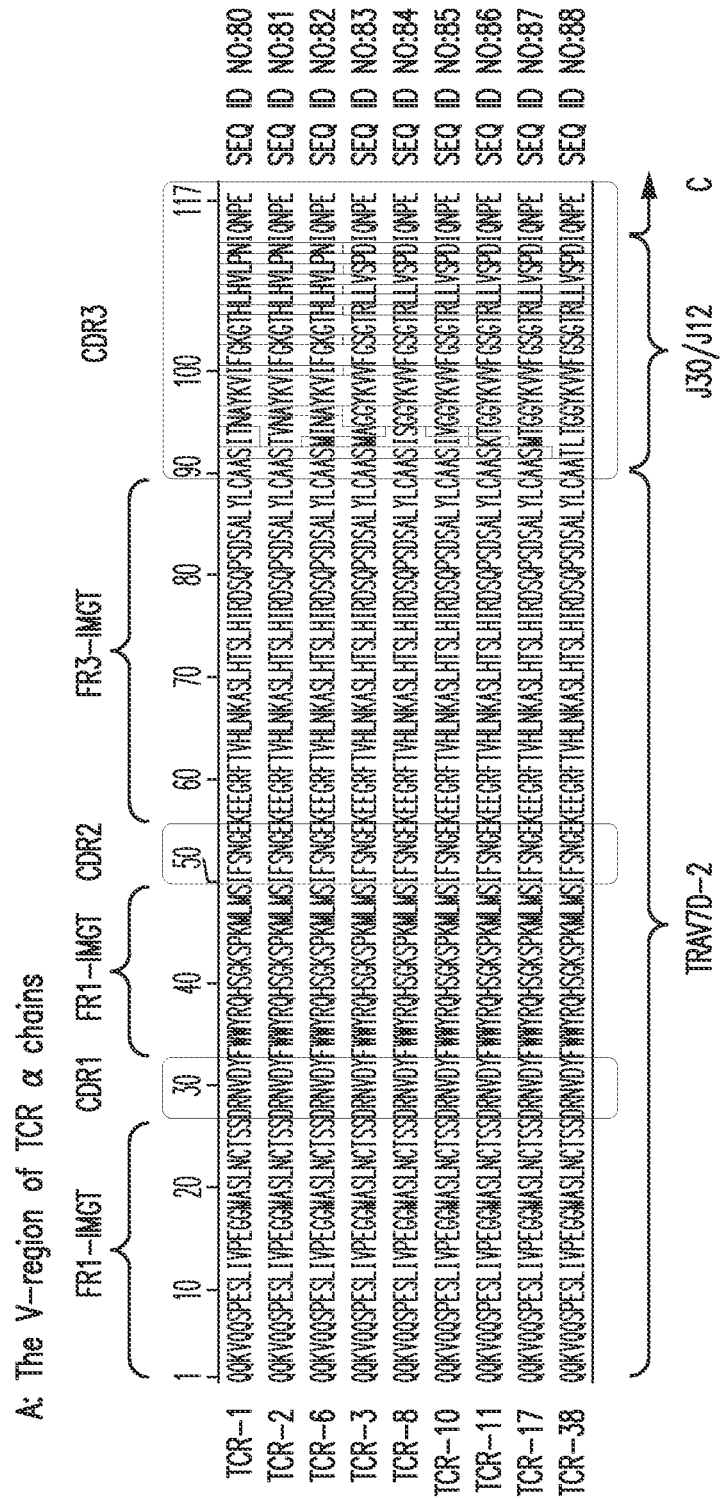
FIG. 16A shows the V-region of TCR α chains and FIG. 16B shows the V-region of TCR β chains.
Figure 16B:
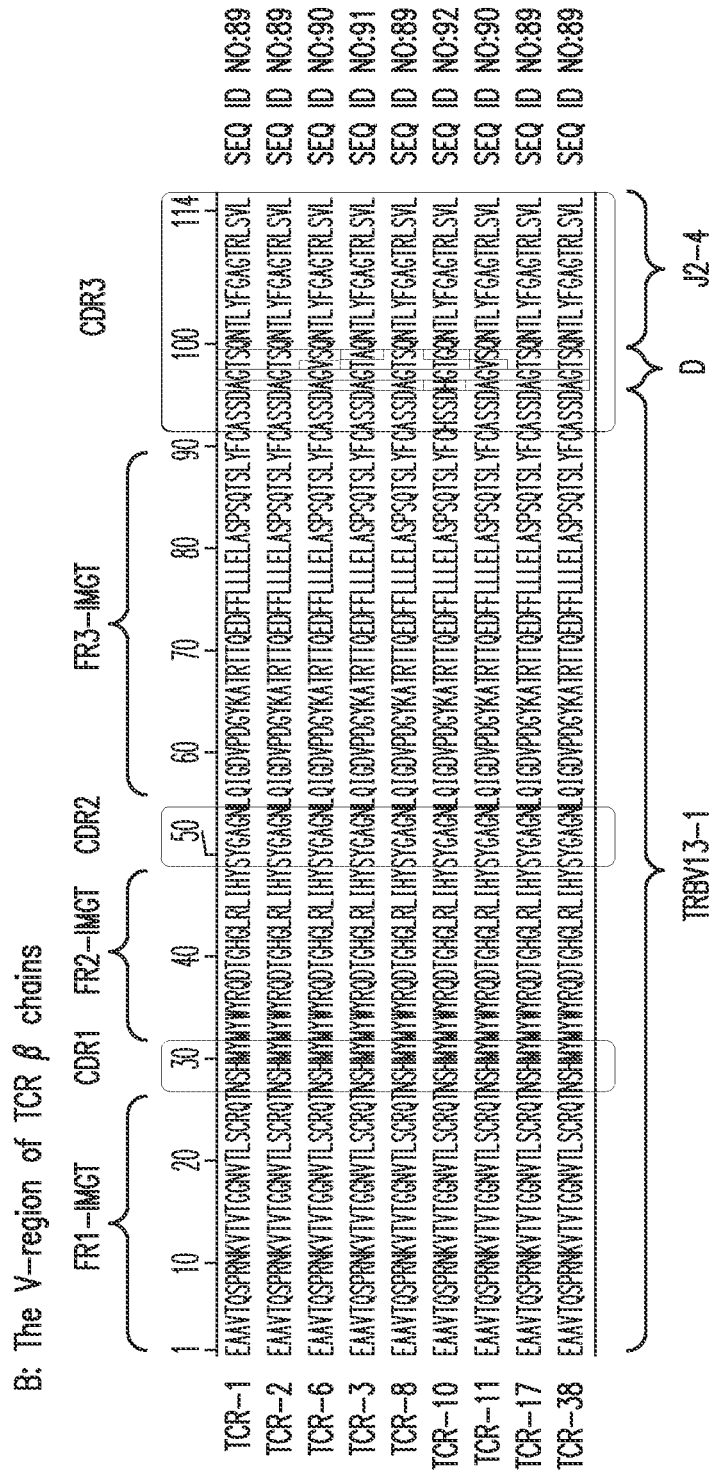

In this experiment, the paired TCRα and β chain genes from the 14 hybridomas capable of producing IL-2 after co-culture with HepG2 tumor cells were amplified and sequenced. The result was summarized in Table 1. Out of 14 hybridomas, 9 unique sets of TCR genes were identified. The sequences of TCR2 (Clone 1G8) and TCR4 (Clone 2F6) are identical, so are the TCR3 (Clone 10A3) and TCR5 (Clone 6D9). TCR6 (Clone 5B3), TCR7 (Clone 5B10), and TCR13 (Clone 11B10) are identical, so are TCR38 (Clone 2C3) and TCR39 (Clone 3E4). The amino acid sequences of α and β chains of TCR1-3, 6, 8, 10, 11, 17, and 38 were then compared to the NCBI and IMGT databank. The sequence data showed that all nine TCR α chains had the same variable region (TRAV7D-2), and that the TCR β chains also shared the same variable region (TRBV13-1), which is consistent with the data from anti-Vβ8.3 antibody staining (FIG. 16). Detail analysis reveals that the sequence of TCR1 and TCR2 is very similar. The β chain of TCR1 and TCR2 are identical and the α-chain of TCR1 and TCR2 had two amino acid differences in the V-J junction. On the other hand, the TCR3 is more divergent from TCR1 and TCR2. Although the β chain of TCR3 is only one amino acid difference from TCR1 and TCR2, the J region of α chain is encoded by a different J gene. While the J gene of TCR1 and TCR2 α chain is TRAJ30, the TCR3 α chain J gene is TRAJ12.

All of the amino acid differences in the 9 TCR genes identified herein are found in the CDR3 region of the α (FIG. 17A) and β (FIG. 17B) chains.

TABLE 1

Summary of the TCR Gene Clones

| Hybridoma # | TCR Clone # | Chains | V | D | J | C |
|---|---|---|---|---|---|---|
| 8D11 | TCR1 | TCRA-1 | Trav7d-2 | | Traj30 | C |
| | | TCRB-1 | Trbv13-1 | 9nts | Trabj2-4 | C2 |
| 1G8 | TCR2 | TCRA-2 | Trav7d-2 | | Traj30 | C |
| | | TCRB-2 | Trbv13-1 | 9nts | Trbj2-4 | C2 |
| 10A3 | TCR3 | TCRA-3 | Trav7d-2 | | Traj12 | C |
| | | TCRB-3 | Trbv13-1 | 9nts | Trbj2-4 | C2 |
| 2F6 | TCR4 | Identical to TCR-2 | | | | |
| 6D9 | TCR5 | Identical to TCR-3 | | | | |
| 5B3 | TCR6 | TCRA-1 | Trav7d-2 | | Traj30 | C |
| | | TCRB-1 | Trbv13-1 | | Trabj2-4 | C2 |
| 5B10 | TCR7 | Identical to TCR-6 | | | | |
| 5G3 | TCR8 | TCRA-8 | Trav7d-2 | | Traj12 | C |
| | | TCRB-8 | Trbv13-1 | | Trabj2-4 | C2 |
| 7H9 | TCR10 | TCRA-10 | Trav7d-2 | | Traj12 | C |
| | | TCRB-10 | Trbv13-1 | | Trbj2-4 | C2 |
| 8E3 | TCR11 | TCRA-11 | Trav7d-2 | | Traj12 | C |
| | | TCRB-11 | Trbv13-1 | | Trabj2-4 | C2 |
| 11b10 | TCR13 | Identical to TCR-6 | | | | |
| 4D2 | TCR17 | TCRA-17 | Trav7d-2 | | Traj12 | C |
| | | TCRB-17 | Trbv13-1 | | Trabj2-4 | C2 |
| 2C3 | TCR38 | TCRA-38 | Trav7d-2 | | Traj12 | C |
| | | TCRB-38 | Trbv13-1 | | Trbj2-4 | C2 |
| 3E4 | TCR39 | Identical to TCR-17 | | | | |

Table 1. The 14 paired TCR alpha and beta chains are summarized. TCR4 and TCR2 are identical. TCR5 and TCR3 are identical. TCR6, TCR7 and TCR13 are identical. TCR38 and TCR39 are identical.
1. Protein sequences of TCRA-1 and TCRA-2 have 2AA difference between V-J junction
2. The TCRA-3 is significantly different from TCRA-1 and TCRA-2. In fact, the J region of TCRA-3 is totally different from TCRA-1 and TCRA-2.
3. Protein sequences of TCRB-1 and TCRB-2 are identical.
4. Protein sequences of TCRB-3 and TCRB-1 are identical except one AA from Serine (116S) to Alanine (116A) between V-D Junction.
5. The D region in TCRB between V-J is 9 nt without obvious homology to any sequence in the databank.

Example 6: Expression of the Paired TCR α and β Chain Genes in Primary Human T Cells Forms Functional TCRs that Bind Tet158 Tetramer Materials and Methods TCR genes and recombinant lv: TCR α and β chains gene were designed and synthesized by using the above identified V-D-J region and C-region. A P2A sequence (Cho, H. I., et al., *Cancer Res*, 69:9012-9019 (2009)) is inserted between α and β chain to separate α and β chains. The entire genes were codon optimized and cloned into lv.

Transduction of human T cells: Human T cells were isolated from buffy coat by negative selection. CD3/CD28 Tetrameric antibody complex (Stemcell Technologies, Vancouver) was then added to activate the cells for 2 days before they were transduced with recombinant lv.

Results

Figure 5A:
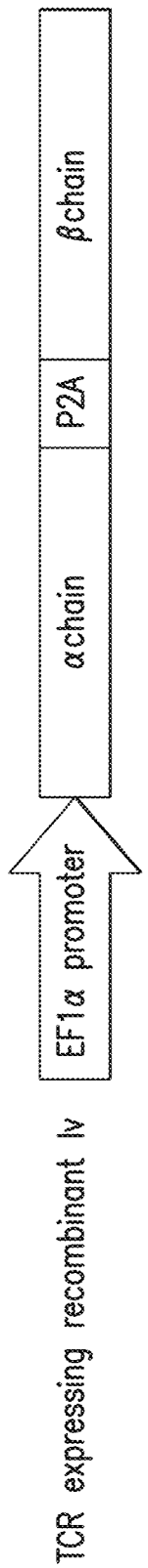
FIG. 5A is a schematic of the recombinant lv expressing TCR genes. The paired TCR α and β chain genes were expressed as a single molecule under the control of EF1α promoter. A P2A sequence was inserted in between to allow generation of equal number of TCR α and β chains.

In this experiment, whether the hAFP-specific TCR genes could engineer human T cells to create TCR redirected T cells (TCR-T) and whether such TCR-T cells would acquire the capability of specifically recognizing and killing hAFP+ tumor cells were investigated. To this end, three TCR genes (TCR1, TCR2, and TCR3) were synthesized and cloned into lv. The P2A sequence was inserted between the TCR α and β genes to generate equal number of TCR α and β chains in target T cells (FIG. 5A). To study whether the TCR α and β chains can form functional TCRs after expression, Jurkat cells were transduced with the TCR-lv and it was found that gene transfer of any of the three sets of TCR genes could effectively render Jurkat cells the capability of binding $Tet_{158}$ tetramer, indicating the TCR gene expression in Jurkat cells can form functional TCR (FIG. 5B). Next, whether these TCR genes could engineer primary human T cells to redirect them to recognize HLA-A2/hAFP158 complex was studied. First, it was found that human T cells of healthy donors could be effectively transduced by recombinant lv after CD3/CD28 activation. Using GFP as reporter protein, at MOI of 10, approximately 60% of human T cells can be transduced by GFP-lv (FIG. 12). Next, transduction of primary human T cells with the TCR genes revealed that approximately 20-30% of them could effectively bind $Tet_{158}$ tetramer (FIG. 5C). Although the T cells from different donors may be transduced with different efficacy, there was no significant transduction difference among the 3 sets of TCR genes. However, the mean fluorescent intensity (MFI) of $Tet_{158}$ tetramer was consistently higher on the TCR3 gene transduced CD8 and CD4 T cells than TCR1 and TCR2 transduced cells, suggesting that TCR3 may have higher affinity for the HLA-A2/$hAFP_{158}$, which is in agreement with the data of $Tet_{158}$ tetramer staining on hybridoma cells (FIG. 4C). Both CD8 and CD4 TCR-T cells could bind $Tet_{158}$ Tetramer, indicating that the TCR binding to HLA-A2/$hAFP_{158}$ is independent of CD8. However, the MFI of $Tet_{158}$ staining on CD8 TCR-T is always higher than that on CD4 TCR-T cells (FIG. 5D), suggesting that CD8 help enhances the binding of the TCR to HLA-A2/$hAFP_{158}$ complex. In addition, the TCR-T cells were stained with anti-TCR Vβ 8.3 or $Tet_{158}$ tetramer. The percent of $Tet_{158}$ Tetramer+ cells is nearly identical to the percent of anti-TCR Vβ8.3+ cells (FIG. 13).

Figure 6A:
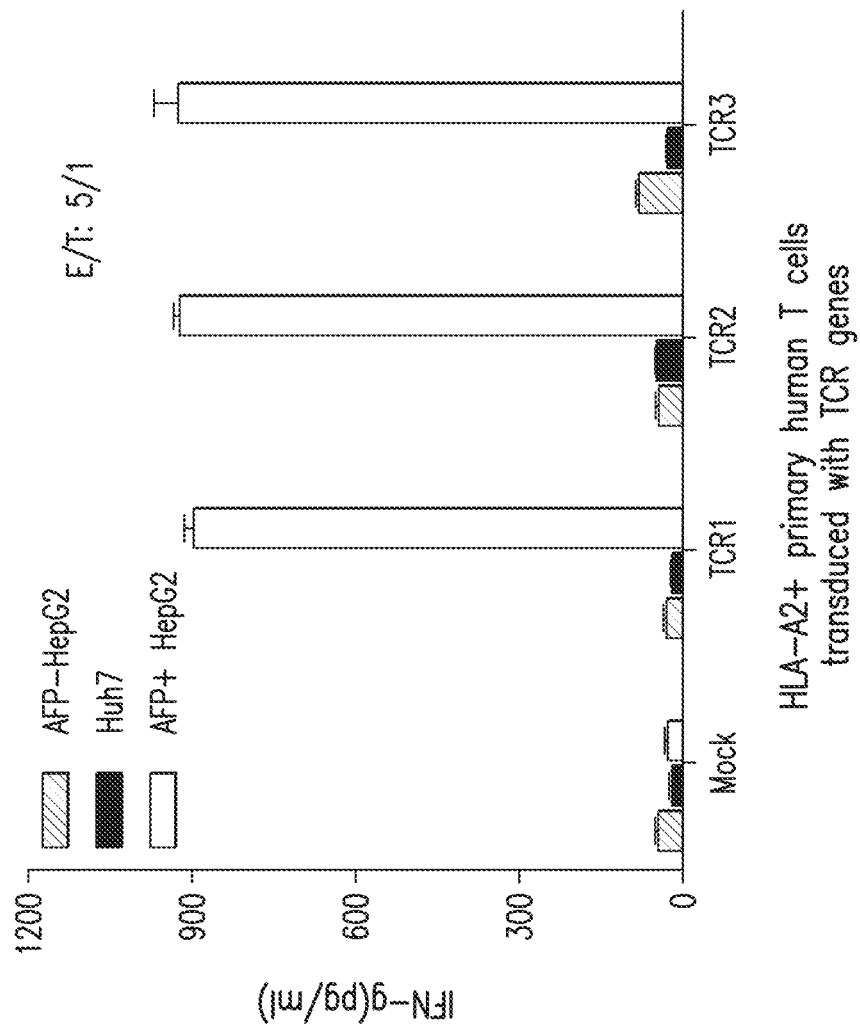
FIG. 6A is a bar graph of IFN-g (pg/ml) from primary human T cells transduced with TCR genes and treated with AFP-HepG2 (hatched bars), Huh7 (black bars) or AFP+HepG2 (white bars).
Figure 8:
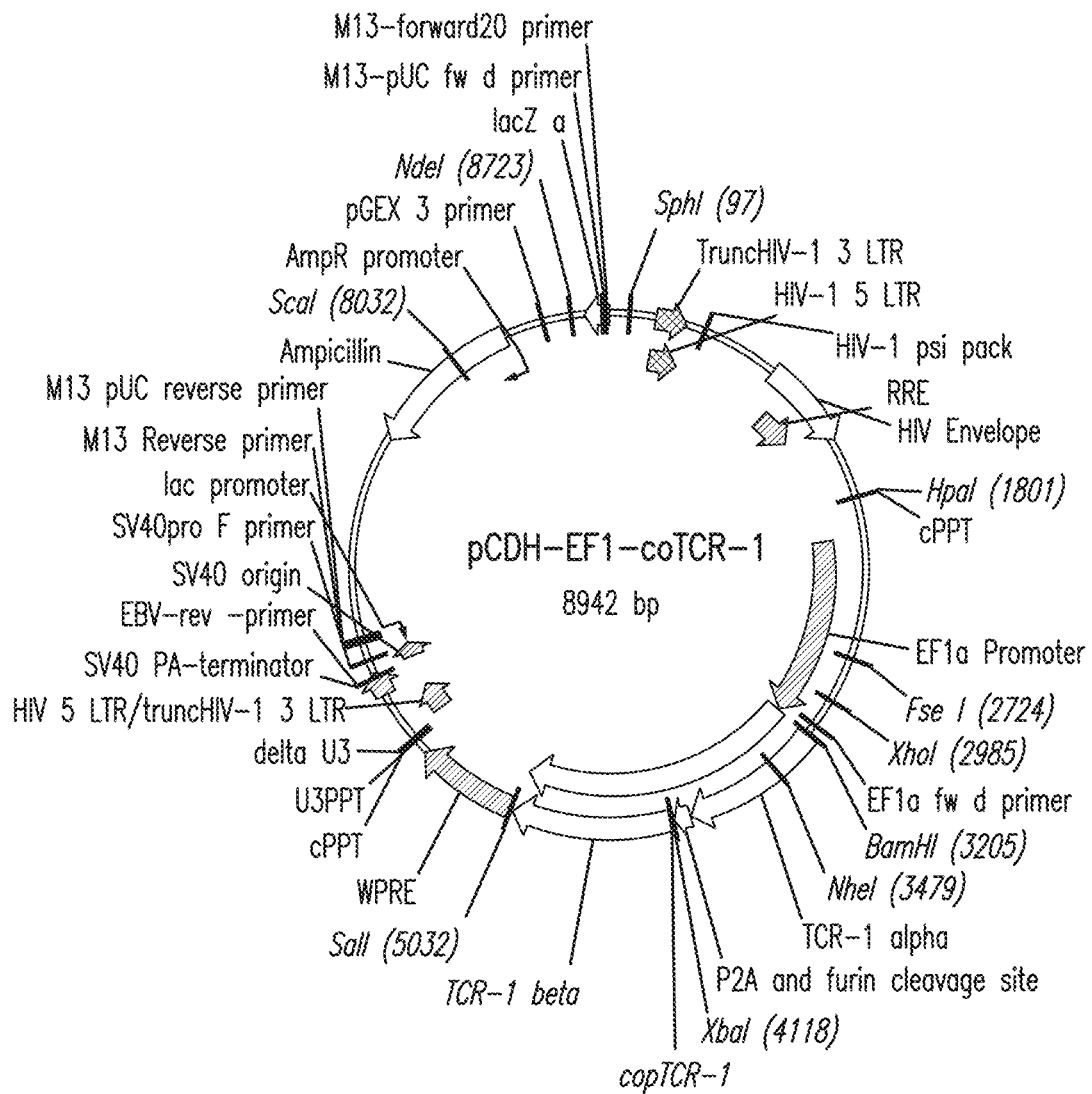
FIG. 8 is a map of TCR-1 expressing lentivector, pCDH-EF1-coTCR-1.
Figure 9:
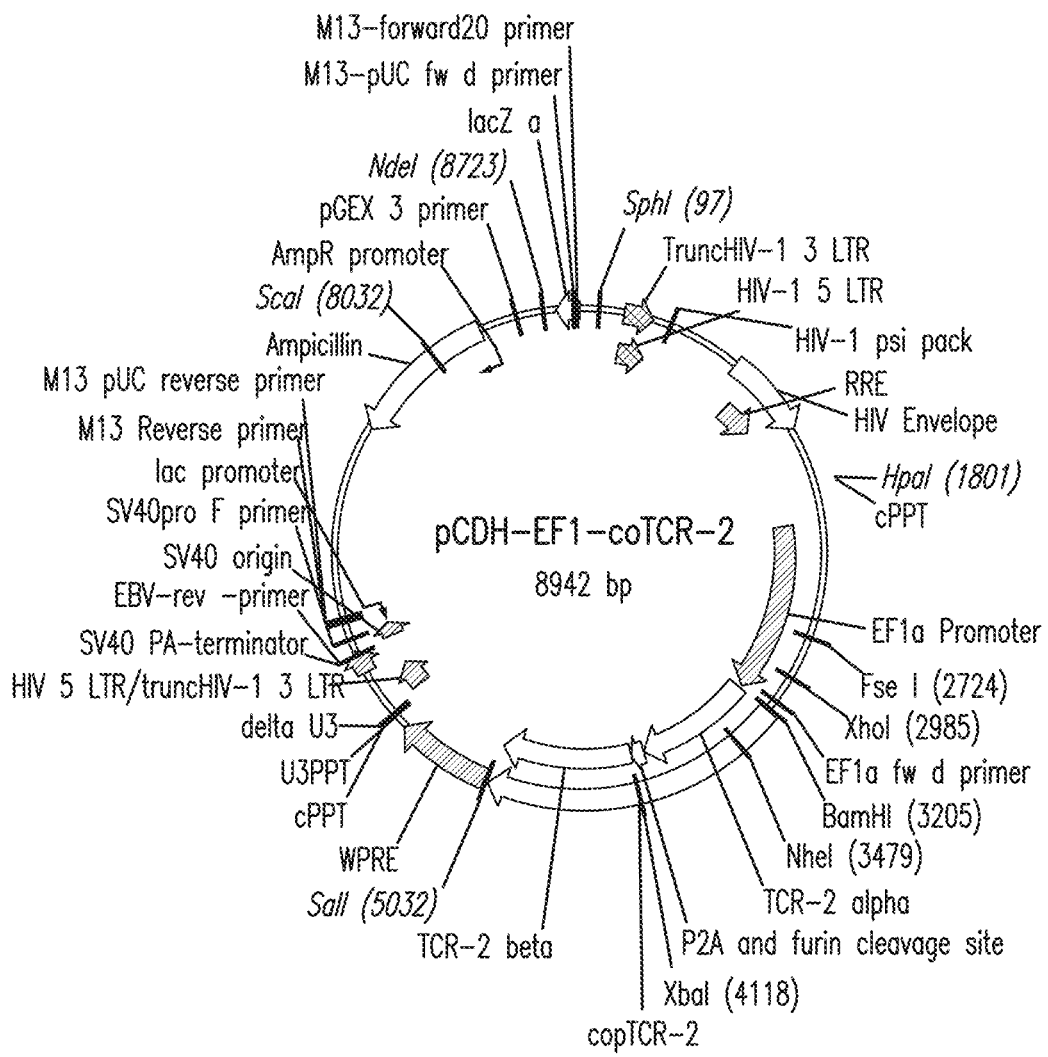
FIG. 9 is a map of TCR-1 expressing lentivector, pCDH-EF1-coTCR-2.
Figure 10:
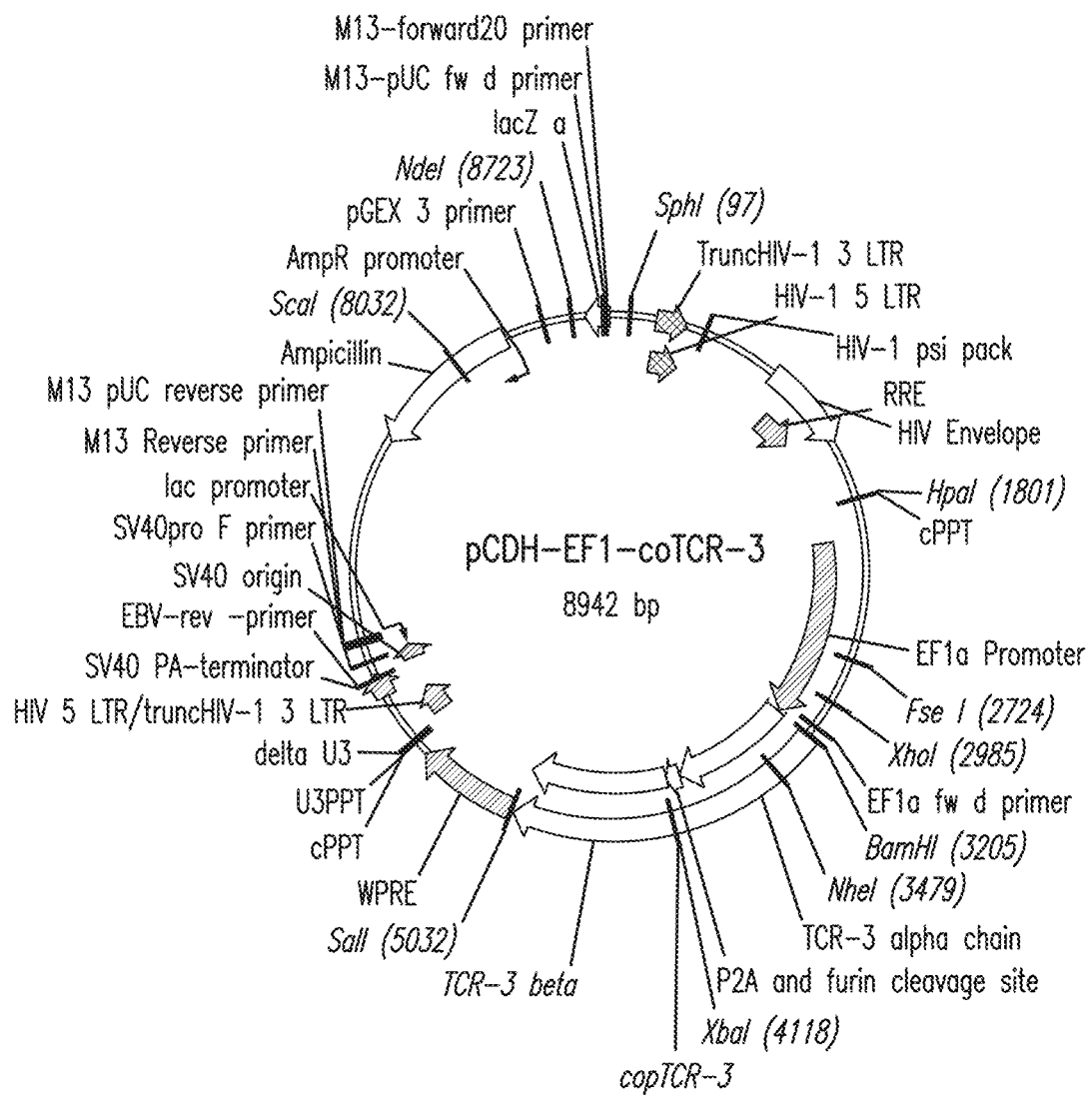
FIG. 10 is a map of TCR-1 expressing lentivector, pCDH-EF1-coTCR-3.
Figure 14A:
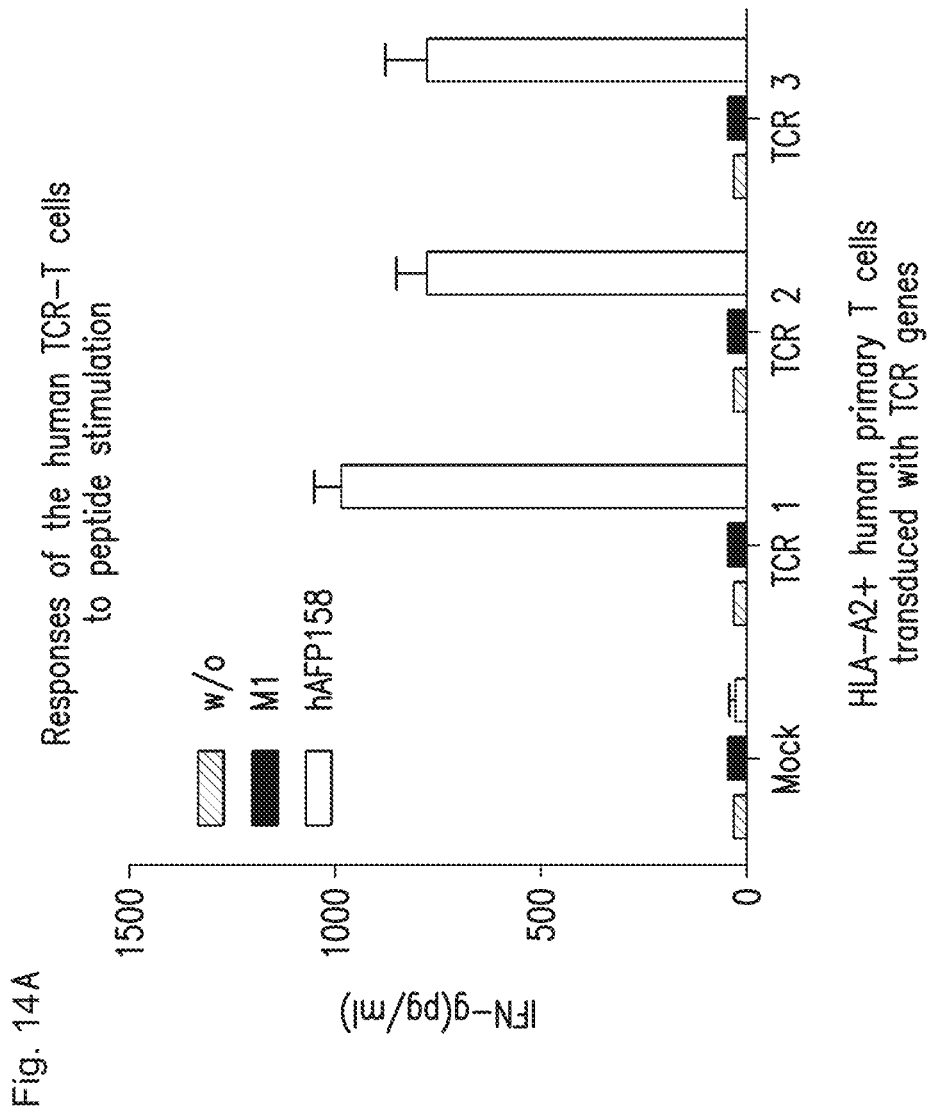

Example 7: Human TCR-T Cells Specifically Activated by HLA-A2 Presented $hAFP_{158}$ Peptide Materials and Methods IFNγ was detected by ELISA after the TCR gene transduced human T cells were co-cultured overnight with HLA-A2+hAFP+ HepG2 cells, HLA-A2+hAFP− HepG2 cells, or HLA-A2-hAFP+ tumor cells.
Results
To study whether the human TCR-T cells could be specifically activated by HLA-A2 presented $hAFP_{158}$ peptide, cytokine production of human TCR-T was measured after stimulation with HLA-A2 mouse splenocytes pulsed with $hAFP_{158}$ peptides. The data showed that human TCR-T cells could be specifically stimulated to produce IFNγ by HLA-A2 cells pulsed with $hAFP_{158}$ peptide. In contrast, no IFNγ was detected in the human TCR-T culture after stimulation with influenza virus M1 peptide. The mock transduced human T cells do not respond to $hAFP_{158}$ peptide stimulation (FIG. 14A). The IFNγ production was mainly from CD8 T cells (FIG. 14B), while the IL2 was also produced by CD4 T cells (FIG. 14C). Next, we found that human TCR-T cells could be activated by HLA-A2+ hAFP+HepG2 tumor cells to produce IFNγ. In contrast, HLA-A2+ hAFP− or HLA-A2− hAFP+ human tumor cells could not activate TCR-T cells (FIG. 6A). Again, the IFNγ production was mainly produced in the CD8 TCR-T cells (FIG. 6B). But both the CD4 (FIG. 6C) and CD8 (FIG. 6B) TCR-T cells are able to produce IL-2. Again, there is no significant difference among the three TCRs. Furthermore, the induction of TCR-T proliferation by HepG2 tumor cells was studied. We found that, after co-culture with the HepG2 tumor cells, the human TCR-T cells, especially the CD8 T cells, underwent significant proliferation (FIG. 6D).

Example 8: Human CD8 TCR-T Cells have Strong and Specific Cytotoxicity Against HLA-A2+hAFP+ Tumor Cells Materials and Methods ELISA of cytokines: ELISA of IFNγ and IL-2 was conducted as instructed by manufacturer (Biolegend, San Diego, CA).
Cytotoxic assay: TCR-T cells were added to growing HepG2 tumor cells. Cytotoxicity assay was conducted using LDH assay as instructed (Promega, Madison, WI).
Prodidium iodide (PI) staining: The dead cells were stained with PI as instructed (BD Biosciences, San Diego, CA).
Results
In this experiment, the cytotoxic activity of human TCR-T cells was studied. Using LDH assay, we first showed that the human TCR-T cells could effectively kill 80% of HepG2 tumor cells within 24 hours of co-culture at E/T ratio of 5. In contrast, the TCR-T cells did not generate significant cytotoxic effect on the AFP− or HLA-A2− tumor cells (FIG. 7A). The cytotoxicity against HepG2 tumor cells was dose dependent (FIG. 7B). Even at E/T ration of 0.5 (the $Tet_{158}$+ cells is ~30%, thus the ratio of $Tet_{158}$ Tetramer+ T cells to target cells was only 0.15), there was a >50% of killing after 24 hours co-culture. By using purified CD8 and CD4 T cells to conduct cytotoxicity assay, we showed that HepG2 tumor cell killing activity was mainly from the CD8 T cells (FIG. 7C-E). However, the CD4 TCR-T cells also had a lower level of cytotoxicity, resulting in 15% of specific killing of HepG2 tumor cells at ratio of 1.5/1 (FIG. 7E). After 24 hours of co-culture, the CD8 TCR-T cells encircled (may be attracted to) the HepG2 tumor cells to form clusters (FIG. 7D). On the other hand, the CD4 TCR-T and mock-transduced T cells did not form obvious clusters. In addition, the PI staining revealed that most of the tumor cells in the cluster are dead cells (FIG. 7F). Consistent with LDH assay, most of the cytotoxic activity was from the CD8 TCR-T cells. The PI staining showed that CD4 TCR-T cells had a lower activity (15%) of killing hepG2 tumor cells, which is in agreement with LDH assay. The mock-transduced human T cells did not induce cell death of HepG2 tumor cells.

Example 9: Adoptive Transfer of Human TCR-T Generates Antitumor Effect Against HepG2 Tumors in NSG Mice Materials and Methods:
In order to study the in vivo antitumor effect of human TCR-T, NSG mice bearing 4 day HepG2 tumors were adoptively transferred with 20 million human TCR-T cells. Tumor growth was monitored by measuring the length, width, and height. Tumor volume was calculated as ½(length×width×height).
Results:
In this experiment, the in vivo antitumor effect of human TCR-T cells was studied. Primary human T cells were transduced with lv and approximately 40% of the total T cells (25% of CD8 T cells and 54% of CD4 T cells) were Tet158+ TCR-T cells before adoptive transfer (FIG. 11A).

We found that adoptive transfer of human TCR-T cells could inhibit HpeG2 tumor outgrowth in NSG mice (FIG. 11B). One of the TCR-T treated-mice developed a tumor, but the tumor was the eradicated by 3 weeks after adoptive transfer (FIG. 11C-D). The kinetics of the transferred human T cells showed that both mock-T and TCR-T cells survived approximately 3-4 weeks in the absence of human IL-2 (FIG. 11E). But compared to mock-T cells, there was a significant increase of the percentage of $Tet_{158}$+ cells among the TCR-T, especially the CD4 TCR-T cells on day 8 after transfer (FIG. 11F), suggesting that there might be an antigen-induced TCR-T expansion.

---

We claim:

1. A method for treating an HLA-A2/Hafp$_{158}$ expressing cancer in a subject in need thereof, the method comprising administering said subject a therapeutically effective amount of CD4 and/or CD8 T cells comprising a recombinant T cell receptor (TCR) comprising a Vα domain and a Vβ domain,
   (a) the Vα domain comprising three complementarity determining regions (CDRs), CDR1, CDR2 and CDR3, wherein CDR1 comprises an amino acid sequence of DRNVDY (residues 47 to 52 of SEQ ID NO:2), wherein CDR2 comprises an amino acid sequence of IFSNGE (residues 70 to 75 of SEQ ID NO:2), and wherein CDR3 comprises an amino acid sequence set forth in SEQ ID NO: 29; and
   (b) the Vβ domain comprising three CDRs, CDR1, CDR2 and CDR3, wherein CDR1 comprises an amino acid sequence of NSHNY (residues 44 to 48 of SEQ ID NO:11), wherein CDR2 comprises an amino acid sequence of SYGAGN (residues 66 to 71 of SEQ ID NO: 11), and wherein CDR3 comprises an amino acid sequence set forth in SEQ ID NO: 37.

2. The method of claim 1, wherein the cancer is hepatocellular carcinoma.

3. The method of claim 1, wherein the T cell is autologous to the subject.

4. The method of claim 1, wherein the TCR is a humanized TCR.

5. The method of claim 1, wherein the T cell is a human cell.

* * * * *

SEQUENCE LISTING

```
<160> NUMBER OF SEQ ID NOS: 105

<210> SEQ ID NO 1
<211> LENGTH: 9
<212> TYPE: PRT
<213> ORGANISM: Homo sapiens

<400> SEQUENCE: 1

Phe Met Asn Lys Phe Ile Tyr Glu Ile
1               5

<210> SEQ ID NO 2
<211> LENGTH: 132
<212> TYPE: PRT
<213> ORGANISM: Artificial Sequence
<220> FEATURE:
<223> OTHER INFORMATION: Synthetic

<400> SEQUENCE: 2

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Thr Asn Ala Tyr Lys Val Ile Phe Gly Lys Gly Thr His Leu His
        115                 120                 125

Val Leu Pro Asn
    130

<210> SEQ ID NO 3
<211> LENGTH: 132
<212> TYPE: PRT
<213> ORGANISM: Artificial Sequence
<220> FEATURE:
<223> OTHER INFORMATION: Synthetic

<400> SEQUENCE: 3

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
```

```
Lys Met Leu Met Ser Ile Phe Ser Asn Gly Glu Lys Glu Glu Gly Arg
 65                  70                  75                  80

Phe Thr Val His Leu Asn Lys Ala Ser Leu His Thr Ser Leu His Ile
                 85                  90                  95

Arg Asp Ser Gln Pro Ser Asp Ser Ala Leu Tyr Leu Cys Ala Ala Ser
                100                 105                 110

Thr Val Asn Ala Tyr Lys Val Ile Phe Gly Lys Gly Thr His Leu His
            115                 120                 125

Val Leu Pro Asn
        130

<210> SEQ ID NO 4
<211> LENGTH: 132
<212> TYPE: PRT
<213> ORGANISM: Artificial Sequence
<220> FEATURE:
<223> OTHER INFORMATION: Synthetic

<400> SEQUENCE: 4

Met Lys Ser Phe Ser Ile Ser Leu Val Val Leu Trp Leu Gln Leu Asn
  1               5                  10                  15

Trp Val Asn Ser Gln Gln Lys Val Gln Gln Ser Pro Glu Ser Leu Ile
             20                  25                  30

Val Pro Glu Gly Gly Met Ala Ser Leu Asn Cys Thr Ser Ser Asp Arg
         35                  40                  45

Asn Val Asp Tyr Phe Trp Trp Tyr Arg Gln His Ser Gly Lys Ser Pro
     50                  55                  60

Lys Met Leu Met Ser Ile Phe Ser Asn Gly Glu Lys Glu Glu Gly Arg
 65                  70                  75                  80

Phe Thr Val His Leu Asn Lys Ala Ser Leu His Thr Ser Leu His Ile
                 85                  90                  95

Arg Asp Ser Gln Pro Ser Asp Ser Ala Leu Tyr Leu Cys Ala Ala Ser
                100                 105                 110

Met Ala Gly Gly Tyr Lys Val Val Phe Gly Ser Gly Thr Arg Leu Leu
            115                 120                 125

Val Ser Pro Asp
        130

<210> SEQ ID NO 5
<211> LENGTH: 132
<212> TYPE: PRT
<213> ORGANISM: Artificial Sequence
<220> FEATURE:
<223> OTHER INFORMATION: Synthetic

<400> SEQUENCE: 5

Met Lys Ser Phe Ser Ile Ser Leu Val Val Leu Trp Leu Gln Leu Asn
  1               5                  10                  15

Trp Val Asn Ser Gln Gln Lys Val Gln Gln Ser Pro Glu Ser Leu Ile
             20                  25                  30

Val Pro Glu Gly Gly Met Ala Ser Leu Asn Cys Thr Ser Ser Asp Arg
         35                  40                  45

Asn Val Asp Tyr Phe Trp Trp Tyr Arg Gln His Ser Gly Lys Ser Pro
     50                  55                  60

Lys Met Leu Met Ser Ile Phe Ser Asn Gly Glu Lys Glu Glu Gly Arg
 65                  70                  75                  80
```

```
Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Ile Asn Ala Tyr Lys Val Ile Phe Gly Lys Gly Thr His Leu His
        115                 120                 125

Val Leu Pro Asn
    130

<210> SEQ ID NO 6
<211> LENGTH: 132
<212> TYPE: PRT
<213> ORGANISM: Artificial Sequence
<220> FEATURE:
<223> OTHER INFORMATION: Synthetic

<400> SEQUENCE: 6

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Ser Gly Gly Tyr Lys Val Val Phe Gly Ser Gly Thr Arg Leu Leu
        115                 120                 125

Val Ser Pro Asp
    130

<210> SEQ ID NO 7
<211> LENGTH: 132
<212> TYPE: PRT
<213> ORGANISM: Artificial Sequence
<220> FEATURE:
<223> OTHER INFORMATION: Synthetic

<400> SEQUENCE: 7

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110
```

Ile Val Gly Gly Tyr Lys Val Val Phe Gly Ser Gly Thr Arg Leu Leu
            115                 120                 125

Val Ser Pro Asp
    130

<210> SEQ ID NO 8
<211> LENGTH: 132
<212> TYPE: PRT
<213> ORGANISM: Artificial Sequence
<220> FEATURE:
<223> OTHER INFORMATION: Synthetic

<400> SEQUENCE: 8

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Lys Thr Gly Gly Tyr Lys Val Val Phe Gly Ser Gly Thr Arg Leu Leu
        115                 120                 125

Val Ser Pro Asp
    130

<210> SEQ ID NO 9
<211> LENGTH: 132
<212> TYPE: PRT
<213> ORGANISM: Artificial Sequence
<220> FEATURE:
<223> OTHER INFORMATION: Synthetic

<400> SEQUENCE: 9

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Thr Gly Gly Tyr Lys Val Val Phe Gly Ser Gly Thr Arg Leu Leu
        115                 120                 125

Val Ser Pro Asp

-continued

```
                                130

<210> SEQ ID NO 10
<211> LENGTH: 132
<212> TYPE: PRT
<213> ORGANISM: Artificial Sequence
<220> FEATURE:
<223> OTHER INFORMATION: Synthetic

<400> SEQUENCE: 10

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Thr
            100                 105                 110

Leu Thr Gly Gly Tyr Lys Val Val Phe Gly Ser Gly Thr Arg Leu Leu
        115                 120                 125

Val Ser Pro Asp
        130

<210> SEQ ID NO 11
<211> LENGTH: 131
<212> TYPE: PRT
<213> ORGANISM: Artificial Sequence
<220> FEATURE:
<223> OTHER INFORMATION: Synthetic

<400> SEQUENCE: 11

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ser Asp
            100                 105                 110

Ala Gly Thr Ser Gln Asn Thr Leu Tyr Phe Gly Ala Gly Thr Arg Leu
        115                 120                 125

Ser Val Leu
        130

<210> SEQ ID NO 12
<211> LENGTH: 131
```

<212> TYPE: PRT
<213> ORGANISM: Artificial Sequence
<220> FEATURE:
<223> OTHER INFORMATION: Synthetic

<400> SEQUENCE: 12

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ser Asp
            100                 105                 110

Ala Gly Thr Ala Gln Asn Thr Leu Tyr Phe Gly Ala Gly Thr Arg Leu
        115                 120                 125

Ser Val Leu
    130

<210> SEQ ID NO 13
<211> LENGTH: 131
<212> TYPE: PRT
<213> ORGANISM: Artificial Sequence
<220> FEATURE:
<223> OTHER INFORMATION: Synthetic

<400> SEQUENCE: 13

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ser Asp
            100                 105                 110

Ala Gly Val Ser Gln Asn Thr Leu Tyr Phe Gly Ala Gly Thr Arg Leu
        115                 120                 125

Ser Val Leu
    130

<210> SEQ ID NO 14
<211> LENGTH: 131
<212> TYPE: PRT
<213> ORGANISM: Artificial Sequence
<220> FEATURE:
<223> OTHER INFORMATION: Synthetic

```
<400> SEQUENCE: 14

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ser Asp
            100                 105                 110

His Gly Thr Gly Gln Asn Thr Leu Tyr Phe Gly Ala Gly Thr Arg Leu
        115                 120                 125

Ser Val Leu
    130

<210> SEQ ID NO 15
<211> LENGTH: 268
<212> TYPE: PRT
<213> ORGANISM: Artificial Sequence
<220> FEATURE:
<223> OTHER INFORMATION: Synthetic

<400> SEQUENCE: 15

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Thr Asn Ala Tyr Lys Val Ile Phe Gly Lys Gly Thr His Leu His
        115                 120                 125

Val Leu Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
```

-continued

```
                210                 215                 220
Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
                245                 250                 255

Phe Asn Leu Leu Met Thr Leu Arg Leu Trp Ser Ser
                260                 265

<210> SEQ ID NO 16
<211> LENGTH: 268
<212> TYPE: PRT
<213> ORGANISM: Artificial Sequence
<220> FEATURE:
<223> OTHER INFORMATION: Synthetic

<400> SEQUENCE: 16

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
                20                  25                  30

Val Pro Glu Gly Gly Met Ala Ser Leu Asn Cys Thr Ser Ser Asp Arg
            35                  40                  45

Asn Val Asp Tyr Phe Trp Trp Tyr Arg Gln His Ser Gly Lys Ser Pro
        50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Thr Val Asn Ala Tyr Lys Val Ile Phe Gly Lys Gly Thr His Leu His
        115                 120                 125

Val Leu Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
                245                 250                 255

Phe Asn Leu Leu Met Thr Leu Arg Leu Trp Ser Ser
                260                 265

<210> SEQ ID NO 17
<211> LENGTH: 268
<212> TYPE: PRT
<213> ORGANISM: Artificial Sequence
<220> FEATURE:
<223> OTHER INFORMATION: Synthetic
```

<400> SEQUENCE: 17

```
Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Ala Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 18
<211> LENGTH: 268
<212> TYPE: PRT
<213> ORGANISM: Artificial Sequence
<220> FEATURE:
<223> OTHER INFORMATION: Synthetic

<400> SEQUENCE: 18

```
Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80
```

```
Phe Thr Val His Leu Asn Lys Ala Ser Leu His Thr Ser Leu His Ile
                85                  90                  95
Arg Asp Ser Gln Pro Ser Asp Ser Ala Leu Tyr Leu Cys Ala Ala Ser
            100                 105                 110
Met Ile Asn Ala Tyr Lys Val Ile Phe Gly Lys Gly Thr His Leu His
        115                 120                 125
Val Leu Pro Asn Ile Gln Asn Pro Glu Pro Ala Val Tyr Gln Leu Lys
    130                 135                 140
Asp Pro Arg Ser Gln Asp Ser Thr Leu Cys Leu Phe Thr Asp Phe Asp
145                 150                 155                 160
Ser Gln Ile Asn Val Pro Lys Thr Met Glu Ser Gly Thr Phe Ile Thr
                165                 170                 175
Asp Lys Thr Val Leu Asp Met Lys Ala Met Asp Ser Lys Ser Asn Gly
            180                 185                 190
Ala Ile Ala Trp Ser Asn Gln Thr Ser Phe Thr Cys Gln Asp Ile Phe
        195                 200                 205
Lys Glu Thr Asn Ala Thr Tyr Pro Ser Ser Asp Val Pro Cys Asp Ala
    210                 215                 220
Thr Leu Thr Glu Lys Ser Phe Glu Thr Asp Met Asn Leu Asn Phe Gln
225                 230                 235                 240
Asn Leu Ser Val Met Gly Leu Arg Ile Leu Leu Leu Lys Val Ala Gly
                245                 250                 255
Phe Asn Leu Leu Met Thr Leu Arg Leu Trp Ser Ser
            260                 265

<210> SEQ ID NO 19
<211> LENGTH: 268
<212> TYPE: PRT
<213> ORGANISM: Artificial Sequence
<220> FEATURE:
<223> OTHER INFORMATION: Synthetic

<400> SEQUENCE: 19

Met Lys Ser Phe Ser Ile Ser Leu Val Val Leu Trp Leu Gln Leu Asn
1               5                   10                  15
Trp Val Asn Ser Gln Gln Lys Val Gln Gln Ser Pro Glu Ser Leu Ile
            20                  25                  30
Val Pro Glu Gly Gly Met Ala Ser Leu Asn Cys Thr Ser Ser Asp Arg
        35                  40                  45
Asn Val Asp Tyr Phe Trp Trp Tyr Arg Gln His Ser Gly Lys Ser Pro
    50                  55                  60
Lys Met Leu Met Ser Ile Phe Ser Asn Gly Glu Lys Glu Glu Gly Arg
65                  70                  75                  80
Phe Thr Val His Leu Asn Lys Ala Ser Leu His Thr Ser Leu His Ile
                85                  90                  95
Arg Asp Ser Gln Pro Ser Asp Ser Ala Leu Tyr Leu Cys Ala Ala Ser
            100                 105                 110
Ile Ser Gly Gly Tyr Lys Val Val Phe Gly Ser Gly Thr Arg Leu Leu
        115                 120                 125
Val Ser Pro Asp Ile Gln Asn Pro Glu Pro Ala Val Tyr Gln Leu Lys
    130                 135                 140
Asp Pro Arg Ser Gln Asp Ser Thr Leu Cys Leu Phe Thr Asp Phe Asp
145                 150                 155                 160
Ser Gln Ile Asn Val Pro Lys Thr Met Glu Ser Gly Thr Phe Ile Thr
                165                 170                 175
```

```
Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
            245                 250                 255

Phe Asn Leu Leu Met Thr Leu Arg Leu Trp Ser Ser
            260                 265

<210> SEQ ID NO 20
<211> LENGTH: 268
<212> TYPE: PRT
<213> ORGANISM: Artificial Sequence
<220> FEATURE:
<223> OTHER INFORMATION: Synthetic

<400> SEQUENCE: 20

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Val Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
            245                 250                 255

Phe Asn Leu Leu Met Thr Leu Arg Leu Trp Ser Ser
            260                 265
```

<210> SEQ ID NO 21
<211> LENGTH: 268
<212> TYPE: PRT
<213> ORGANISM: Artificial Sequence
<220> FEATURE:
<223> OTHER INFORMATION: Synthetic

<400> SEQUENCE: 21

```
Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Lys Thr Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
                245                 250                 255

Phe Asn Leu Leu Met Thr Leu Arg Leu Trp Ser Ser
            260                 265
```

<210> SEQ ID NO 22
<211> LENGTH: 268
<212> TYPE: PRT
<213> ORGANISM: Artificial Sequence
<220> FEATURE:
<223> OTHER INFORMATION: Synthetic

<400> SEQUENCE: 22

```
Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45
```

```
Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
                100                 105                 110

Met Thr Gly Gly Tyr Lys Val Val Phe Gly Ser Gly Thr Arg Leu Leu
                115                 120                 125

Val Ser Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
                180                 185                 190

Ala Ile Ala Trp Ser Asn Gln Thr Ser Phe Thr Cys Gln Asp Ile Phe
                195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
                260                 265

<210> SEQ ID NO 23
<211> LENGTH: 268
<212> TYPE: PRT
<213> ORGANISM: Artificial Sequence
<220> FEATURE:
<223> OTHER INFORMATION: Synthetic

<400> SEQUENCE: 23

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
                20                  25                  30

Val Pro Glu Gly Gly Met Ala Ser Leu Asn Cys Thr Ser Ser Asp Arg
                35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Thr
                100                 105                 110

Leu Thr Gly Gly Tyr Lys Val Val Phe Gly Ser Gly Thr Arg Leu Leu
                115                 120                 125

Val Ser Pro Asp Ile Gln Asn Pro Glu Pro Ala Val Tyr Gln Leu Lys
    130                 135                 140
```

```
Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
                260                 265
```

<210> SEQ ID NO 24
<211> LENGTH: 304
<212> TYPE: PRT
<213> ORGANISM: Artificial Sequence
<220> FEATURE:
<223> OTHER INFORMATION: Synthetic

<400> SEQUENCE: 24

```
Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
    50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Ser Asp
                100                 105                 110

Ala Gly Thr Ser Gln Asn Thr Leu Tyr Phe Gly Ala Gly Thr Arg Leu
            115                 120                 125

Ser Val Leu Glu Asp Leu Arg Asn Val Thr Pro Pro Lys Val Ser Leu
130                 135                 140

Phe Glu Pro Ser Lys Ala Glu Ile Ala Asn Lys Arg Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240
```

```
Pro Lys Pro Val Thr Gln Asn Ile Ser Ala Glu Ala Trp Gly Arg Ala
            245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
290                 295                 300
```

<210> SEQ ID NO 25
<211> LENGTH: 304
<212> TYPE: PRT
<213> ORGANISM: Artificial Sequence
<220> FEATURE:
<223> OTHER INFORMATION: Synthetic

<400> SEQUENCE: 25

```
Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
            35                  40                  45

Met Tyr Trp Tyr Arg Gln Asp Thr Gly His Gly Leu Arg Leu Ile His
50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
            85                  90                  95

Leu Ala Ser Pro Ser Gln Thr Ser Leu Tyr Phe Cys Ala Ser Ser Asp
            100                 105                 110

Ala Gly Thr Ala Gln Asn Thr Leu Tyr Phe Gly Ala Gly Thr Arg Leu
            115                 120                 125

Ser Val Leu Glu Asp Leu Arg Asn Val Thr Pro Pro Lys Val Ser Leu
130                 135                 140

Phe Glu Pro Ser Lys Ala Glu Ile Ala Asn Lys Arg Lys Ala Thr Leu
145                 150                 155                 160

Val Cys Leu Ala Arg Gly Phe Phe Pro Asp His Val Glu Leu Ser Trp
            165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
            245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
290                 295                 300
```

<210> SEQ ID NO 26
<211> LENGTH: 304
<212> TYPE: PRT
<213> ORGANISM: Artificial Sequence
<220> FEATURE:
<223> OTHER INFORMATION: Synthetic

<400> SEQUENCE: 26

Met Gly Ser Arg Leu Phe Leu Val Leu Ser Leu Leu Cys Thr Lys His
1               5                   10                  15

Met Glu Ala Ala Val Thr Gln Ser Pro Arg Asn Lys Val Thr Val Thr
            20                  25                  30

Gly Gly Asn Val Thr Leu Ser Cys Arg Gln Thr Asn Ser His Asn Tyr
        35                  40                  45

Met Tyr Trp Tyr Arg Gln Asp Thr Gly His Gly Leu Arg Leu Ile His
50                  55                  60

Tyr Ser Tyr Gly Ala Gly Asn Leu Gln Ile Gly Asp Val Pro Asp Gly
65                  70                  75                  80

Tyr Lys Ala Thr Arg Thr Thr Gln Glu Asp Phe Phe Leu Leu Leu Glu
                85                  90                  95

Leu Ala Ser Pro Ser Gln Thr Ser Leu Tyr Phe Cys Ala Ser Cys Asp
            100                 105                 110

Ala Gly Val Ser Gln Asn Thr Leu Tyr Phe Gly Ala Gly Thr Arg Leu
        115                 120                 125

Ser Val Leu Glu Asp Leu Arg Asn Val Thr Pro Pro Lys Val Ser Leu
    130                 135                 140

Phe Glu Pro Ser Lys Ala Glu Ile Ala Asn Lys Arg Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

<210> SEQ ID NO 27
<211> LENGTH: 304
<212> TYPE: PRT
<213> ORGANISM: Artificial Sequence
<220> FEATURE:
<223> OTHER INFORMATION: Synthetic

<400> SEQUENCE: 27

Met Gly Ser Arg Leu Phe Leu Val Leu Ser Leu Leu Cys Thr Lys His

-continued

```
              1               5                   10                  15
            Met Glu Ala Ala Val Thr Gln Ser Pro Arg Asn Lys Val Thr Val Thr
                            20                  25                  30
            Gly Gly Asn Val Thr Leu Ser Cys Arg Gln Thr Asn Ser His Asn Tyr
                            35                  40                  45
            Met Tyr Trp Tyr Arg Gln Asp Thr Gly His Gly Leu Arg Leu Ile His
                    50                  55                  60
            Tyr Ser Tyr Gly Ala Gly Asn Leu Gln Ile Gly Asp Val Pro Asp Gly
            65                  70                  75                  80
            Tyr Lys Ala Thr Arg Thr Thr Gln Glu Asp Phe Phe Leu Leu Leu Glu
                            85                  90                  95
            Leu Ala Ser Pro Ser Gln Thr Ser Leu Tyr Phe Cys Ala Ser Ser Asp
                            100                 105                 110
            His Gly Thr Gly Gln Asn Thr Leu Tyr Phe Gly Ala Gly Thr Arg Leu
                            115                 120                 125
            Ser Val Leu Glu Asp Leu Arg Asn Val Thr Pro Pro Lys Val Ser Leu
                            130                 135                 140
            Phe Glu Pro Ser Lys Ala Glu Ile Ala Asn Lys Arg Lys Ala Thr Leu
            145                 150                 155                 160
            Val Cys Leu Ala Arg Gly Phe Phe Pro Asp His Val Glu Leu Ser Trp
                            165                 170                 175
            Trp Val Asn Gly Lys Glu Val His Ser Gly Val Ser Thr Asp Pro Gln
                            180                 185                 190
            Ala Tyr Lys Glu Ser Asn Tyr Ser Tyr Cys Leu Ser Ser Arg Leu Arg
                            195                 200                 205
            Val Ser Ala Thr Phe Trp His Asn Pro Arg Asn His Phe Arg Cys Gln
                            210                 215                 220
            Val Gln Phe His Gly Leu Ser Glu Glu Asp Lys Trp Pro Glu Gly Ser
            225                 230                 235                 240
            Pro Lys Pro Val Thr Gln Asn Ile Ser Ala Glu Ala Trp Gly Arg Ala
                            245                 250                 255
            Asp Cys Gly Ile Thr Ser Ala Ser Tyr Gln Gln Gly Val Leu Ser Ala
                            260                 265                 270
            Thr Ile Leu Tyr Glu Ile Leu Leu Gly Lys Ala Thr Leu Tyr Ala Val
                            275                 280                 285
            Leu Val Ser Thr Leu Val Val Met Ala Met Val Lys Arg Lys Asn Ser
                            290                 295                 300

<210> SEQ ID NO 28
<211> LENGTH: 28
<212> TYPE: PRT
<213> ORGANISM: Artificial Sequence
<220> FEATURE:
<223> OTHER INFORMATION: Synthetic

<400> SEQUENCE: 28

Ala Ala Ser Ile Thr Asn Ala Tyr Lys Val Ile Phe Gly Lys Gly Thr
            1               5                   10                  15

His Leu His Val Leu Pro Asn Ile Gln Asn Pro Glu
                            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic
```

<400> SEQUENCE: 29

Ala Ala Ser Thr Val Asn Ala Tyr Lys Val Ile Phe Gly Lys Gly Thr
1               5                   10                  15

His Leu His Val Leu Pro Asn Ile Gln Asn Pro Glu
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic

<400> SEQUENCE: 30

Ala Ala Ser Met Ala Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 31
<211> LENGTH: 28
<212> TYPE: PRT
<213> ORGANISM: Artificial Sequence
<220> FEATURE:
<223> OTHER INFORMATION: Synthetic

<400> SEQUENCE: 31

Ala Ala Ser Met Ile Asn Ala Tyr Lys Val Ile Phe Gly Lys Gly Thr
1               5                   10                  15

His Leu His Val Leu Pro Asn Ile Gln Asn Pro Glu
            20                  25

<210> SEQ ID NO 32
<211> LENGTH: 28
<212> TYPE: PRT
<213> ORGANISM: Artificial Sequence
<220> FEATURE:
<223> OTHER INFORMATION: Synthetic

<400> SEQUENCE: 32

Ala Ala Ser Ile Ser Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 33
<211> LENGTH: 28
<212> TYPE: PRT
<213> ORGANISM: Artificial Sequence
<220> FEATURE:
<223> OTHER INFORMATION: Synthetic

<400> SEQUENCE: 33

Ala Ala Ser Ile Val Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 34
<211> LENGTH: 28
<212> TYPE: PRT
<213> ORGANISM: Artificial Sequence
<220> FEATURE:

<223> OTHER INFORMATION: Synthetic

<400> SEQUENCE: 34

Ala Ala Ser Lys Thr Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 35
<211> LENGTH: 28
<212> TYPE: PRT
<213> ORGANISM: Artificial Sequence
<220> FEATURE:
<223> OTHER INFORMATION: Synthetic

<400> SEQUENCE: 35

Ala Ala Ser Met Thr Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic

<400> SEQUENCE: 36

Ala Ala Thr Leu Thr Gly Gly Tyr Lys Val Val Phe Gly Ser Gly Thr
1               5                   10                  15

Arg Leu Leu Val Ser Pro Asp Ile Gln Asn Pro Glu
            20                  25

<210> SEQ ID NO 37
<211> LENGTH: 23
<212> TYPE: PRT
<213> ORGANISM: Artificial Sequence
<220> FEATURE:
<223> OTHER INFORMATION: Synthetic

<400> SEQUENCE: 37

Ala Ser Ser Asp Ala Gly Thr Ser Gln Asn Thr Leu Tyr Phe Gly Ala
1               5                   10                  15

Gly Thr Arg Leu Ser Val Leu
            20

<210> SEQ ID NO 38
<211> LENGTH: 23
<212> TYPE: PRT
<213> ORGANISM: Artificial Sequence
<220> FEATURE:
<223> OTHER INFORMATION: Synthetic

<400> SEQUENCE: 38

Ala Ser Ser Asp Ala Gly Thr Ala Gln Asn Thr Leu Tyr Phe Gly Ala
1               5                   10                  15

Gly Thr Arg Leu Ser Val Leu
            20

<210> SEQ ID NO 39
<211> LENGTH: 23
<212> TYPE: PRT
<213> ORGANISM: Artificial Sequence

```
<220> FEATURE:
<223> OTHER INFORMATION: Synthetic

<400> SEQUENCE: 39

Ala Ser Ser Asp Ala Gly Val Ser Gln Asn Thr Leu Tyr Phe Gly Ala
1               5                   10                  15

Gly Thr Arg Leu Ser Val Leu
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic

<400> SEQUENCE: 40

Ala Ser Ser Asp His Gly Thr Gly Gln Asn Thr Leu Tyr Phe Gly Ala
1               5                   10                  15

Gly Thr Arg Leu Ser Val Leu
            20

<210> SEQ ID NO 41
<211> LENGTH: 222
<212> TYPE: PRT
<213> ORGANISM: Artificial Sequence
<220> FEATURE:
<223> OTHER INFORMATION: Synthetic

<400> SEQUENCE: 41

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Ile Thr Asn Ala
                85                  90                  95

Tyr Lys Val Ile Phe Gly Lys Gly Thr His Leu His Val Leu Pro Asn
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
    130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
    210                 215                 220
```

<210> SEQ ID NO 42
<211> LENGTH: 222
<212> TYPE: PRT
<213> ORGANISM: Artificial Sequence
<220> FEATURE:
<223> OTHER INFORMATION: Synthetic

<400> SEQUENCE: 42

```
Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Thr Val Asn Ala
                85                  90                  95

Tyr Lys Val Ile Phe Gly Lys Gly Thr His Leu His Val Leu Pro Asn
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
210                 215                 220
```

<210> SEQ ID NO 43
<211> LENGTH: 222
<212> TYPE: PRT
<213> ORGANISM: Artificial Sequence
<220> FEATURE:
<223> OTHER INFORMATION: Synthetic

<400> SEQUENCE: 43

```
Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Ala Gly Gly
                85                  90                  95
```

Tyr Lys Val Val Phe Gly Ser Gly Thr Arg Leu Leu Val Ser Pro Asp
            100                 105                 110

Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
            130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
                180                 185                 190

Ala Thr Tyr Pro Ser Ser Asp Val Pro Cys Asp Ala Thr Leu Thr Glu
                195                 200                 205

Lys Ser Phe Glu Thr Asp Met Asn Leu Asn Phe Gln Asn Leu
                210                 215                 220

<210> SEQ ID NO 44
<211> LENGTH: 222
<212> TYPE: PRT
<213> ORGANISM: Artificial Sequence
<220> FEATURE:
<223> OTHER INFORMATION: Synthetic

<400> SEQUENCE: 44

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Ile Asn Ala
                85                  90                  95

Tyr Lys Val Ile Phe Gly Lys Gly Thr His Leu His Val Leu Pro Asn
            100                 105                 110

Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
            130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
                180                 185                 190

Ala Thr Tyr Pro Ser Ser Asp Val Pro Cys Asp Ala Thr Leu Thr Glu
                195                 200                 205

Lys Ser Phe Glu Thr Asp Met Asn Leu Asn Phe Gln Asn Leu
                210                 215                 220

<210> SEQ ID NO 45

<211> LENGTH: 222
<212> TYPE: PRT
<213> ORGANISM: Artificial Sequence
<220> FEATURE:
<223> OTHER INFORMATION: Synthetic

<400> SEQUENCE: 45

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Ile Ser Gly Gly
                85                  90                  95

Tyr Lys Val Val Phe Gly Ser Gly Thr Arg Leu Leu Val Ser Pro Asp
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
    130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
    210                 215                 220

<210> SEQ ID NO 46
<211> LENGTH: 222
<212> TYPE: PRT
<213> ORGANISM: Artificial Sequence
<220> FEATURE:
<223> OTHER INFORMATION: Synthetic

<400> SEQUENCE: 46

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Ile Val Gly Gly
                85                  90                  95

Tyr Lys Val Val Phe Gly Ser Gly Thr Arg Leu Leu Val Ser Pro Asp

```
            100                 105                 110
Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
        130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
                180                 185                 190

Ala Thr Tyr Pro Ser Ser Asp Val Pro Cys Asp Ala Thr Leu Thr Glu
            195                 200                 205

Lys Ser Phe Glu Thr Asp Met Asn Leu Asn Phe Gln Asn Leu
        210                 215                 220

<210> SEQ ID NO 47
<211> LENGTH: 222
<212> TYPE: PRT
<213> ORGANISM: Artificial Sequence
<220> FEATURE:
<223> OTHER INFORMATION: Synthetic

<400> SEQUENCE: 47

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Lys Thr Gly Gly
                85                  90                  95

Tyr Lys Val Val Phe Gly Ser Gly Thr Arg Leu Leu Val Ser Pro Asp
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
    130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
    210                 215                 220

<210> SEQ ID NO 48
<211> LENGTH: 222
<212> TYPE: PRT
```

```
<213> ORGANISM: Artificial Sequence
<220> FEATURE:
<223> OTHER INFORMATION: Synthetic

<400> SEQUENCE: 48

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Thr Gly Gly
                85                  90                  95

Tyr Lys Val Val Phe Gly Ser Gly Thr Arg Leu Leu Val Ser Pro Asp
                100                 105                 110

Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
    210                 215                 220

<210> SEQ ID NO 49
<211> LENGTH: 222
<212> TYPE: PRT
<213> ORGANISM: Artificial Sequence
<220> FEATURE:
<223> OTHER INFORMATION: Synthetic

<400> SEQUENCE: 49

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Thr Leu Thr Gly Gly
                85                  90                  95

Tyr Lys Val Val Phe Gly Ser Gly Thr Arg Leu Leu Val Ser Pro Asp
                100                 105                 110
```

```
Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
        130                 135                 140

Val Pro Lys Thr Met Glu Ser Gly Thr Phe Ile Thr Asp Lys Thr Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
        195                 200                 205

Lys Ser Phe Glu Thr Asp Met Asn Leu Asn Phe Gln Asn Leu
210                 215                 220
```

<210> SEQ ID NO 50
<211> LENGTH: 259
<212> TYPE: PRT
<213> ORGANISM: Artificial Sequence
<220> FEATURE:
<223> OTHER INFORMATION: Synthetic

<400> SEQUENCE: 50

```
Glu Ala Ala Val Thr Gln Ser Pro Arg Asn Lys Val Thr Val Thr Gly
1               5                   10                  15

Gly Asn Val Thr Leu Ser Cys Arg Gln Thr Asn Ser His Asn Tyr Met
            20                  25                  30

Tyr Trp Tyr Arg Gln Asp Thr Gly His Gly Leu Arg Leu Ile His Tyr
        35                  40                  45

Ser Tyr Gly Ala Gly Asn Leu Gln Ile Gly Asp Val Pro Asp Gly Tyr
    50                  55                  60

Lys Ala Thr Arg Thr Thr Gln Glu Asp Phe Phe Leu Leu Leu Glu Leu
65                  70                  75                  80

Ala Ser Pro Ser Gln Thr Ser Leu Tyr Phe Cys Ala Ser Ser Asp Ala
                85                  90                  95

Gly Thr Ser Gln Asn Thr Leu Tyr Phe Gly Ala Gly Thr Arg Leu Ser
            100                 105                 110

Val Leu Glu Asp Leu Arg Asn Val Thr Pro Pro Lys Val Ser Leu Phe
        115                 120                 125

Glu Pro Ser Lys Ala Glu Ile Ala Asn Lys Arg Lys Ala Thr Leu Val
    130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Ser Thr Asp Pro Gln Ala
                165                 170                 175

Tyr Lys Glu Ser Asn Tyr Ser Tyr Cys Leu Ser Ser Arg Leu Arg Val
            180                 185                 190

Ser Ala Thr Phe Trp His Asn Pro Arg Asn His Phe Arg Cys Gln Val
        195                 200                 205

Gln Phe His Gly Leu Ser Glu Glu Asp Lys Trp Pro Glu Gly Ser Pro
    210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr Gln Gln Gly Val Leu Ser Ala Thr
                245                 250                 255
```

Ile Leu Tyr

<210> SEQ ID NO 51
<211> LENGTH: 260
<212> TYPE: PRT
<213> ORGANISM: Artificial Sequence
<220> FEATURE:
<223> OTHER INFORMATION: Synthetic

<400> SEQUENCE: 51

Val Thr Gln Ser Pro Arg Asn Lys Val Thr Val Thr Gly Gly Asn Val
1               5                   10                  15

Thr Leu Ser Cys Arg Gln Thr Asn Ser His Asn Tyr Met Tyr Trp Tyr
            20                  25                  30

Arg Gln Asp Thr Gly His Gly Leu Arg Leu Ile His Tyr Ser Tyr Gly
        35                  40                  45

Ala Gly Asn Leu Gln Ile Gly Asp Val Pro Asp Gly Tyr Lys Ala Thr
    50                  55                  60

Arg Thr Thr Gln Glu Asp Phe Phe Leu Leu Glu Leu Ala Ser Pro
65                  70                  75                  80

Ser Gln Thr Ser Leu Tyr Phe Cys Ala Ser Ser Asp Ala Gly Thr Ala
            85                  90                  95

Gln Asn Thr Leu Tyr Phe Gly Ala Gly Thr Arg Leu Ser Val Leu Glu
            100                 105                 110

Asp Leu Arg Asn Val Thr Pro Pro Lys Val Ser Leu Phe Glu Pro Ser
        115                 120                 125

Lys Ala Glu Ile Ala Asn Lys Arg Lys Ala Thr Leu Val Cys Leu Ala
130                 135                 140

Arg Gly Phe Phe Pro Asp His Val Glu Leu Ser Trp Trp Val Asn Gly
145                 150                 155                 160

Lys Glu Val His Ser Gly Val Ser Thr Asp Pro Gln Ala Tyr Lys Glu
            165                 170                 175

Ser Asn Tyr Ser Tyr Cys Leu Ser Ser Arg Leu Arg Val Ser Ala Thr
            180                 185                 190

Phe Trp His Asn Pro Arg Asn His Phe Arg Cys Gln Val Gln Phe His
    195                 200                 205

Gly Leu Ser Glu Glu Asp Lys Trp Pro Glu Gly Ser Pro Lys Pro Val
210                 215                 220

Thr Gln Asn Ile Ser Ala Glu Ala Trp Gly Arg Ala Asp Cys Gly Ile
225                 230                 235                 240

Thr Ser Ala Ser Tyr Gln Gln Gly Val Leu Ser Ala Thr Ile Leu Tyr
            245                 250                 255

Glu Ile Leu Leu
            260

<210> SEQ ID NO 52
<211> LENGTH: 259
<212> TYPE: PRT
<213> ORGANISM: Artificial Sequence
<220> FEATURE:
<223> OTHER INFORMATION: Synthetic

<400> SEQUENCE: 52

Glu Ala Ala Val Thr Gln Ser Pro Arg Asn Lys Val Thr Val Thr Gly
1               5                   10                  15

Gly Asn Val Thr Leu Ser Cys Arg Gln Thr Asn Ser His Asn Tyr Met
            20                  25                  30

```
Tyr Trp Tyr Arg Gln Asp Thr Gly His Gly Leu Arg Leu Ile His Tyr
             35                  40                  45

Ser Tyr Gly Ala Gly Asn Leu Gln Ile Gly Asp Val Pro Asp Gly Tyr
 50                      55                  60

Lys Ala Thr Arg Thr Thr Gln Glu Asp Phe Phe Leu Leu Leu Glu Leu
 65                  70                  75                  80

Ala Ser Pro Ser Gln Thr Ser Leu Tyr Phe Cys Ala Ser Cys Asp Ala
                 85                  90                  95

Gly Val Ser Gln Asn Thr Leu Tyr Phe Gly Ala Gly Thr Arg Leu Ser
                100                 105                 110

Val Leu Glu Asp Leu Arg Asn Val Thr Pro Pro Lys Val Ser Leu Phe
            115                 120                 125

Glu Pro Ser Lys Ala Glu Ile Ala Asn Lys Arg Lys Ala Thr Leu Val
130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Ser Thr Asp Pro Gln Ala
                165                 170                 175

Tyr Lys Glu Ser Asn Tyr Ser Tyr Cys Leu Ser Ser Arg Leu Arg Val
                180                 185                 190

Ser Ala Thr Phe Trp His Asn Pro Arg Asn His Phe Arg Cys Gln Val
            195                 200                 205

Gln Phe His Gly Leu Ser Glu Glu Asp Lys Trp Pro Glu Gly Ser Pro
        210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr Gln Gln Gly Val Leu Ser Ala Thr
                245                 250                 255

Ile Leu Tyr

<210> SEQ ID NO 53
<211> LENGTH: 259
<212> TYPE: PRT
<213> ORGANISM: Artificial Sequence
<220> FEATURE:
<223> OTHER INFORMATION: Synthetic

<400> SEQUENCE: 53

Glu Ala Ala Val Thr Gln Ser Pro Arg Asn Lys Val Thr Val Thr Gly
 1               5                  10                  15

Gly Asn Val Thr Leu Ser Cys Arg Gln Thr Asn Ser His Asn Tyr Met
                20                  25                  30

Tyr Trp Tyr Arg Gln Asp Thr Gly His Gly Leu Arg Leu Ile His Tyr
             35                  40                  45

Ser Tyr Gly Ala Gly Asn Leu Gln Ile Gly Asp Val Pro Asp Gly Tyr
 50                      55                  60

Lys Ala Thr Arg Thr Thr Gln Glu Asp Phe Phe Leu Leu Leu Glu Leu
 65                  70                  75                  80

Ala Ser Pro Ser Gln Thr Ser Leu Tyr Phe Cys Ala Ser Ser Asp His
                 85                  90                  95

Gly Thr Gly Gln Asn Thr Leu Tyr Phe Gly Ala Gly Thr Arg Leu Ser
                100                 105                 110

Val Leu Glu Asp Leu Arg Asn Val Thr Pro Pro Lys Val Ser Leu Phe
            115                 120                 125

Glu Pro Ser Lys Ala Glu Ile Ala Asn Lys Arg Lys Ala Thr Leu Val
```

```
            130                 135                 140
Cys Leu Ala Arg Gly Phe Phe Pro Asp His Val Glu Leu Ser Trp Trp
145                 150                 155                 160

Val Asn Gly Lys Glu Val His Ser Gly Val Ser Thr Asp Pro Gln Ala
                165                 170                 175

Tyr Lys Glu Ser Asn Tyr Ser Tyr Cys Leu Ser Ser Arg Leu Arg Val
                180                 185                 190

Ser Ala Thr Phe Trp His Asn Pro Arg Asn His Phe Arg Cys Gln Val
                195                 200                 205

Gln Phe His Gly Leu Ser Glu Glu Asp Lys Trp Pro Glu Gly Ser Pro
                210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr Gln Gln Gly Val Leu Ser Ala Thr
                245                 250                 255

Ile Leu Tyr

<210> SEQ ID NO 54
<211> LENGTH: 602
<212> TYPE: PRT
<213> ORGANISM: Artificial Sequence
<220> FEATURE:
<223> OTHER INFORMATION: Synthetic

<400> SEQUENCE: 54

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
                20                  25                  30

Val Pro Glu Gly Gly Met Ala Ser Leu Asn Cys Thr Ser Ser Asp Arg
                35                  40                  45

Asn Val Asp Tyr Phe Trp Trp Tyr Arg Gln His Ser Gly Lys Ser Pro
                50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
                100                 105                 110

Ile Thr Asn Ala Tyr Lys Val Ile Phe Gly Lys Gly Thr His Leu His
                115                 120                 125

Val Leu Pro Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
                180                 185                 190

Ala Ile Ala Trp Ser Asn Gln Thr Ser Phe Thr Cys Gln Asp Ile Phe
                195                 200                 205

Lys Glu Thr Asn Ala Thr Tyr Pro Ser Ser Asp Val Pro Cys Asp Ala
                210                 215                 220

Thr Leu Thr Glu Lys Ser Phe Glu Thr Asp Met Asn Leu Asn Phe Gln
225                 230                 235                 240
```

```
Asn Leu Ser Val Met Gly Leu Arg Ile Leu Leu Lys Val Ala Gly
            245                 250                 255

Phe Asn Leu Leu Met Thr Leu Arg Leu Trp Ser Ser Gly Ser Arg Ala
            260                 265                 270

Lys Arg Ser Gly Ser Gly Ala Thr Asn Phe Ser Leu Leu Lys Gln Ala
            275                 280                 285

Gly Asp Val Glu Glu Asn Pro Gly Pro Arg Met Gly Ser Arg Leu Phe
            290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
                340                 345                 350

Asp Thr Gly His Gly Leu Arg Leu Ile His Tyr Ser Tyr Gly Ala Gly
                355                 360                 365

Asn Leu Gln Ile Gly Asp Val Pro Asp Gly Tyr Lys Ala Thr Arg Thr
            370                 375                 380

Thr Gln Glu Asp Phe Phe Leu Leu Glu Leu Ala Ser Pro Ser Gln
385                 390                 395                 400

Thr Ser Leu Tyr Phe Cys Ala Ser Ser Asp Ala Gly Thr Ser Gln Asn
                405                 410                 415

Thr Leu Tyr Phe Gly Ala Gly Thr Arg Leu Ser Val Leu Glu Asp Leu
                420                 425                 430

Arg Asn Val Thr Pro Pro Lys Val Ser Leu Phe Glu Pro Ser Lys Ala
            435                 440                 445

Glu Ile Ala Asn Lys Arg Lys Ala Thr Leu Val Cys Leu Ala Arg Gly
            450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
            515                 520                 525

Ser Glu Glu Asp Lys Trp Pro Glu Gly Ser Pro Lys Pro Val Thr Gln
530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
            595                 600

<210> SEQ ID NO 55
<211> LENGTH: 602
<212> TYPE: PRT
<213> ORGANISM: Artificial Sequence
<220> FEATURE:
<223> OTHER INFORMATION: Synthetic

<400> SEQUENCE: 55
```

```
Met Lys Ser Phe Ser Ile Ser Leu Val Val Leu Trp Leu Gln Leu Asn
1               5                   10                  15

Trp Val Asn Ser Gln Lys Val Gln Gln Ser Pro Glu Ser Leu Ile
            20                  25                  30

Val Pro Glu Gly Gly Met Ala Ser Leu Asn Cys Thr Ser Ser Asp Arg
            35                  40                  45

Asn Val Asp Tyr Phe Trp Trp Tyr Arg Gln His Ser Gly Lys Ser Pro
50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
                100                 105                 110

Thr Val Asn Ala Tyr Lys Val Ile Phe Gly Lys Gly Thr His Leu His
            115                 120                 125

Val Leu Pro Asn Ile Gln Asn Pro Glu Pro Ala Val Tyr Gln Leu Lys
        130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
        210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser Gly Ser Arg Ala
            260                 265                 270

Lys Arg Ser Gly Ser Gly Ala Thr Asn Phe Ser Leu Leu Lys Gln Ala
        275                 280                 285

Gly Asp Val Glu Glu Asn Pro Gly Pro Arg Met Gly Ser Arg Leu Phe
    290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
            340                 345                 350

Asp Thr Gly His Gly Leu Arg Leu Ile His Tyr Ser Tyr Gly Ala Gly
            355                 360                 365

Asn Leu Gln Ile Gly Asp Val Pro Asp Gly Tyr Lys Ala Thr Arg Thr
        370                 375                 380

Thr Gln Glu Asp Phe Phe Leu Leu Leu Glu Leu Ala Ser Pro Ser Gln
385                 390                 395                 400

Thr Ser Leu Tyr Phe Cys Ala Ser Ser Asp Ala Gly Thr Ser Gln Asn
                405                 410                 415
```

```
Thr Leu Tyr Phe Gly Ala Gly Thr Arg Leu Ser Val Leu Glu Asp Leu
            420                 425                 430

Arg Asn Val Thr Pro Pro Lys Val Ser Leu Phe Glu Pro Ser Lys Ala
        435                 440                 445

Glu Ile Ala Asn Lys Arg Lys Ala Thr Leu Val Cys Leu Ala Arg Gly
    450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
        515                 520                 525

Ser Glu Glu Asp Lys Trp Pro Glu Gly Ser Pro Lys Pro Val Thr Gln
    530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
        595                 600

<210> SEQ ID NO 56
<211> LENGTH: 602
<212> TYPE: PRT
<213> ORGANISM: Artificial Sequence
<220> FEATURE:
<223> OTHER INFORMATION: Synthetic

<400> SEQUENCE: 56

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Ala Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175
```

```
Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
                245                 250                 255

Phe Asn Leu Leu Met Thr Leu Arg Leu Trp Ser Ser Gly Ser Arg Ala
            260                 265                 270

Lys Arg Ser Gly Ser Gly Ala Thr Asn Phe Ser Leu Leu Lys Gln Ala
        275                 280                 285

Gly Asp Val Glu Glu Asn Pro Gly Pro Arg Met Gly Ser Arg Leu Phe
    290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
            340                 345                 350

Asp Thr Gly His Gly Leu Arg Leu Ile His Tyr Ser Tyr Gly Ala Gly
        355                 360                 365

Asn Leu Gln Ile Gly Asp Val Pro Asp Gly Tyr Lys Ala Thr Arg Thr
    370                 375                 380

Thr Gln Glu Asp Phe Phe Leu Leu Glu Leu Ala Ser Pro Ser Gln
385                 390                 395                 400

Thr Ser Leu Tyr Phe Cys Ala Ser Ser Asp Ala Gly Thr Ala Gln Asn
                405                 410                 415

Thr Leu Tyr Phe Gly Ala Gly Thr Arg Leu Ser Val Leu Glu Asp Leu
            420                 425                 430

Arg Asn Val Thr Pro Pro Lys Val Ser Leu Phe Glu Pro Ser Lys Ala
        435                 440                 445

Glu Ile Ala Asn Lys Arg Lys Ala Thr Leu Val Cys Leu Ala Arg Gly
    450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
        515                 520                 525

Ser Glu Glu Asp Lys Trp Pro Glu Gly Ser Pro Lys Pro Val Thr Gln
    530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
```

595             600

<210> SEQ ID NO 57
<211> LENGTH: 602
<212> TYPE: PRT
<213> ORGANISM: Artificial Sequence
<220> FEATURE:
<223> OTHER INFORMATION: Synthetic

<400> SEQUENCE: 57

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Ile Asn Ala Tyr Lys Val Ile Phe Gly Lys Gly Thr His Leu His
        115                 120                 125

Val Leu Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser Gly Ser Arg Ala
            260                 265                 270

Lys Arg Ser Gly Ser Gly Ala Thr Asn Phe Ser Leu Leu Lys Gln Ala
        275                 280                 285

Gly Asp Val Glu Glu Asn Pro Gly Pro Arg Met Gly Ser Arg Leu Phe
    290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
            340                 345                 350

Asp Thr Gly His Gly Leu Arg Leu Ile His Tyr Ser Tyr Gly Ala Gly

```
                355                 360                 365
Asn Leu Gln Ile Gly Asp Val Pro Asp Gly Tyr Lys Ala Thr Arg Thr
            370                 375                 380

Thr Gln Glu Asp Phe Phe Leu Leu Glu Leu Ala Ser Pro Ser Gln
385                 390                 395                 400

Thr Ser Leu Tyr Phe Cys Ala Ser Ser Asp Ala Gly Val Ser Gln Asn
                405                 410                 415

Thr Leu Tyr Phe Gly Ala Gly Thr Arg Leu Ser Val Leu Glu Asp Leu
            420                 425                 430

Arg Asn Val Thr Pro Pro Lys Val Ser Leu Phe Glu Pro Ser Lys Ala
                435                 440                 445

Glu Ile Ala Asn Lys Arg Lys Ala Thr Leu Val Cys Leu Ala Arg Gly
            450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
                515                 520                 525

Ser Glu Glu Asp Lys Trp Pro Glu Gly Ser Pro Lys Pro Val Thr Gln
            530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
        595                 600

<210> SEQ ID NO 58
<211> LENGTH: 602
<212> TYPE: PRT
<213> ORGANISM: Artificial Sequence
<220> FEATURE:
<223> OTHER INFORMATION: Synthetic

<400> SEQUENCE: 58

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
                20                  25                  30

Val Pro Glu Gly Gly Met Ala Ser Leu Asn Cys Thr Ser Ser Asp Arg
            35                  40                  45

Asn Val Asp Tyr Phe Trp Trp Tyr Arg Gln His Ser Gly Lys Ser Pro
        50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Ser Gly Gly Tyr Lys Val Val Phe Gly Ser Gly Thr Arg Leu Leu
```

-continued

```
            115                 120                 125
Val Ser Pro Asp Ile Gln Asn Pro Glu Pro Ala Val Tyr Gln Leu Lys
            130                 135                 140
Asp Pro Arg Ser Gln Asp Ser Thr Leu Cys Leu Phe Thr Asp Phe Asp
145                 150                 155                 160
Ser Gln Ile Asn Val Pro Lys Thr Met Glu Ser Gly Thr Phe Ile Thr
                    165                 170                 175
Asp Lys Thr Val Leu Asp Met Lys Ala Met Asp Ser Lys Ser Asn Gly
                180                 185                 190
Ala Ile Ala Trp Ser Asn Gln Thr Ser Phe Thr Cys Gln Asp Ile Phe
            195                 200                 205
Lys Glu Thr Asn Ala Thr Tyr Pro Ser Ser Asp Val Pro Cys Asp Ala
        210                 215                 220
Thr Leu Thr Glu Lys Ser Phe Glu Thr Asp Met Asn Leu Asn Phe Gln
225                 230                 235                 240
Asn Leu Ser Val Met Gly Leu Arg Ile Leu Leu Leu Lys Val Ala Gly
                    245                 250                 255
Phe Asn Leu Leu Met Thr Leu Arg Leu Trp Ser Ser Gly Ser Arg Ala
                260                 265                 270
Lys Arg Ser Gly Ser Gly Ala Thr Asn Phe Ser Leu Leu Lys Gln Ala
            275                 280                 285
Gly Asp Val Glu Glu Asn Pro Gly Pro Arg Met Gly Ser Arg Leu Phe
        290                 295                 300
Leu Val Leu Ser Leu Leu Cys Thr Lys His Met Glu Ala Ala Val Thr
305                 310                 315                 320
Gln Ser Pro Arg Asn Lys Val Thr Val Thr Gly Gly Asn Val Thr Leu
                    325                 330                 335
Ser Cys Arg Gln Thr Asn Ser His Asn Tyr Met Tyr Trp Tyr Arg Gln
                340                 345                 350
Asp Thr Gly His Gly Leu Arg Leu Ile His Tyr Ser Tyr Gly Ala Gly
            355                 360                 365
Asn Leu Gln Ile Gly Asp Val Pro Asp Gly Tyr Lys Ala Thr Arg Thr
        370                 375                 380
Thr Gln Glu Asp Phe Phe Leu Leu Leu Glu Leu Ala Ser Pro Ser Gln
385                 390                 395                 400
Thr Ser Leu Tyr Phe Cys Ala Ser Ser Asp Ala Gly Thr Ser Gln Asn
                    405                 410                 415
Thr Leu Tyr Phe Gly Ala Gly Thr Arg Leu Ser Val Leu Glu Asp Leu
                420                 425                 430
Arg Asn Val Thr Pro Pro Lys Val Ser Leu Phe Glu Pro Ser Lys Ala
            435                 440                 445
Glu Ile Ala Asn Lys Arg Lys Ala Thr Leu Val Cys Leu Ala Arg Gly
        450                 455                 460
Phe Phe Pro Asp His Val Glu Leu Ser Trp Trp Val Asn Gly Lys Glu
465                 470                 475                 480
Val His Ser Gly Val Ser Thr Asp Pro Gln Ala Tyr Lys Glu Ser Asn
                    485                 490                 495
Tyr Ser Tyr Cys Leu Ser Ser Arg Leu Arg Val Ser Ala Thr Phe Trp
                500                 505                 510
His Asn Pro Arg Asn His Phe Arg Cys Gln Val Gln Phe His Gly Leu
            515                 520                 525
Ser Glu Glu Asp Lys Trp Pro Glu Gly Ser Pro Lys Pro Val Thr Gln
        530                 535                 540
```

```
Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
            565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
        595                 600

<210> SEQ ID NO 59
<211> LENGTH: 602
<212> TYPE: PRT
<213> ORGANISM: Artificial Sequence
<220> FEATURE:
<223> OTHER INFORMATION: Synthetic

<400> SEQUENCE: 59

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Ile Val Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser Gly Ser Arg Ala
            260                 265                 270

Lys Arg Ser Gly Ser Gly Ala Thr Asn Phe Ser Leu Leu Lys Gln Ala
        275                 280                 285

Gly Asp Val Glu Glu Asn Pro Gly Pro Arg Met Gly Ser Arg Leu Phe
    290                 295                 300
```

```
Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
            325                 330                 335

Ser Cys Arg Gln Thr Asn Ser His Asn Tyr Met Tyr Trp Tyr Arg Gln
            340                 345                 350

Asp Thr Gly His Gly Leu Arg Leu Ile His Tyr Ser Tyr Gly Ala Gly
        355                 360                 365

Asn Leu Gln Ile Gly Asp Val Pro Asp Gly Tyr Lys Ala Thr Arg Thr
370                 375                 380

Thr Gln Glu Asp Phe Phe Leu Leu Glu Leu Ala Ser Pro Ser Gln
385                 390                 395                 400

Thr Ser Leu Tyr Phe Cys Ala Ser Ser Asp His Gly Thr Gly Gln Asn
                405                 410                 415

Thr Leu Tyr Phe Gly Ala Gly Thr Arg Leu Ser Val Leu Glu Asp Leu
            420                 425                 430

Arg Asn Val Thr Pro Pro Lys Val Ser Leu Phe Glu Pro Ser Lys Ala
            435                 440                 445

Glu Ile Ala Asn Lys Arg Lys Ala Thr Leu Val Cys Leu Ala Arg Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
            485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
            515                 520                 525

Ser Glu Glu Asp Lys Trp Pro Glu Gly Ser Pro Lys Pro Val Thr Gln
            530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
            595                 600

<210> SEQ ID NO 60
<211> LENGTH: 602
<212> TYPE: PRT
<213> ORGANISM: Artificial Sequence
<220> FEATURE:
<223> OTHER INFORMATION: Synthetic

<400> SEQUENCE: 60

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
        35                  40                  45

Asn Val Asp Tyr Phe Trp Trp Tyr Arg Gln His Ser Gly Lys Ser Pro
    50                  55                  60
```

```
Lys Met Leu Met Ser Ile Phe Ser Asn Gly Glu Lys Glu Gly Arg
65                  70                  75                  80

Phe Thr Val His Leu Asn Lys Ala Ser Leu His Thr Ser Leu His Ile
            85                  90                  95

Arg Asp Ser Gln Pro Ser Asp Ser Ala Leu Tyr Leu Cys Ala Ala Ser
            100                 105                 110

Lys Thr Gly Gly Tyr Lys Val Val Phe Gly Ser Gly Thr Arg Leu Leu
            115                 120                 125

Val Ser Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser Gly Ser Arg Ala
                260                 265                 270

Lys Arg Ser Gly Ser Gly Ala Thr Asn Phe Ser Leu Leu Lys Gln Ala
            275                 280                 285

Gly Asp Val Glu Glu Asn Pro Gly Pro Arg Met Gly Ser Arg Leu Phe
290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
            325                 330                 335

Ser Cys Arg Gln Thr Asn Ser His Asn Tyr Met Tyr Trp Tyr Arg Gln
            340                 345                 350

Asp Thr Gly His Gly Leu Arg Leu Ile His Tyr Ser Tyr Gly Ala Gly
            355                 360                 365

Asn Leu Gln Ile Gly Asp Val Pro Asp Gly Tyr Lys Ala Thr Arg Thr
            370                 375                 380

Thr Gln Glu Asp Phe Phe Leu Leu Leu Glu Leu Ala Ser Pro Ser Gln
385                 390                 395                 400

Thr Ser Leu Tyr Phe Cys Ala Ser Ser Asp Ala Gly Thr Ser Gln Asn
                405                 410                 415

Thr Leu Tyr Phe Gly Ala Gly Thr Arg Leu Ser Val Leu Glu Asp Leu
                420                 425                 430

Arg Asn Val Thr Pro Pro Lys Val Ser Leu Phe Glu Pro Ser Lys Ala
            435                 440                 445

Glu Ile Ala Asn Lys Arg Lys Ala Thr Leu Val Cys Leu Ala Arg Gly
            450                 455                 460

Phe Phe Pro Asp His Val Glu Leu Ser Trp Trp Val Asn Gly Lys Glu
465                 470                 475                 480
```

-continued

```
Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
        515                 520                 525

Ser Glu Glu Asp Lys Trp Pro Glu Gly Ser Pro Lys Pro Val Thr Gln
    530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
        595                 600

<210> SEQ ID NO 61
<211> LENGTH: 602
<212> TYPE: PRT
<213> ORGANISM: Artificial Sequence
<220> FEATURE:
<223> OTHER INFORMATION: Synthetic

<400> SEQUENCE: 61

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
                20                  25                  30

Val Pro Glu Gly Gly Met Ala Ser Leu Asn Cys Thr Ser Ser Asp Arg
            35                  40                  45

Asn Val Asp Tyr Phe Trp Trp Tyr Arg Gln His Ser Gly Lys Ser Pro
        50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Ser
            100                 105                 110

Met Thr Gly Gly Tyr Lys Val Val Phe Gly Ser Gly Thr Arg Leu Leu
        115                 120                 125

Val Ser Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240
```

Asn Leu Ser Val Met Gly Leu Arg Ile Leu Leu Lys Val Ala Gly
            245                 250                 255

Phe Asn Leu Leu Met Thr Leu Arg Leu Trp Ser Ser Gly Ser Arg Ala
        260                 265                 270

Lys Arg Ser Gly Ser Gly Ala Thr Asn Phe Ser Leu Leu Lys Gln Ala
        275                 280                 285

Gly Asp Val Glu Glu Asn Pro Gly Pro Arg Met Gly Ser Arg Leu Phe
    290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
                340                 345                 350

Asp Thr Gly His Gly Leu Arg Leu Ile His Tyr Ser Tyr Gly Ala Gly
            355                 360                 365

Asn Leu Gln Ile Gly Asp Val Pro Asp Gly Tyr Lys Ala Thr Arg Thr
    370                 375                 380

Thr Gln Glu Asp Phe Phe Leu Leu Leu Glu Leu Ala Ser Pro Ser Gln
385                 390                 395                 400

Thr Ser Leu Tyr Phe Cys Ala Ser Ser Asp Ala Gly Thr Ser Gln Asn
                405                 410                 415

Thr Leu Tyr Phe Gly Ala Gly Thr Arg Leu Ser Val Leu Glu Asp Leu
            420                 425                 430

Arg Asn Val Thr Pro Pro Lys Val Ser Leu Phe Glu Pro Ser Lys Ala
    435                 440                 445

Glu Ile Ala Asn Lys Arg Lys Ala Thr Leu Val Cys Leu Ala Arg Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Ala Tyr Lys Glu Ser Asn
                485                 490                 495

Tyr Ser Tyr Cys Leu Ser Ser Arg Leu Arg Val Ser Ala Thr Phe Trp
            500                 505                 510

His Asn Pro Arg Asn His Phe Arg Cys Gln Val Gln Phe His Gly Leu
    515                 520                 525

Ser Glu Glu Asp Lys Trp Pro Glu Gly Ser Pro Lys Pro Val Thr Gln
530                 535                 540

Asn Ile Ser Ala Glu Ala Trp Gly Arg Ala Asp Cys Gly Ile Thr Ser
545                 550                 555                 560

Ala Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Thr Leu Val
            580                 585                 590

Val Met Ala Met Val Lys Arg Lys Asn Ser
    595                 600

<210> SEQ ID NO 62
<211> LENGTH: 602
<212> TYPE: PRT
<213> ORGANISM: Artificial Sequence
<220> FEATURE:
<223> OTHER INFORMATION: Synthetic

<400> SEQUENCE: 62

-continued

```
Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
            20                  25                  30

Val Pro Glu Gly Gly Met Ala Ser Leu Asn Cys Thr Ser Ser Asp Arg
            35                  40                  45

Asn Val Asp Tyr Phe Trp Trp Tyr Arg Gln His Ser Gly Lys Ser Pro
            50                  55                  60

Lys Met Leu Met Ser Ile Phe Ser Asn Gly Glu Lys Glu Glu Gly Arg
65                  70                  75                  80

Phe Thr Val His Leu Asn Lys Ala Ser Leu His Thr Ser Leu His Ile
                85                  90                  95

Arg Asp Ser Gln Pro Ser Asp Ser Ala Leu Tyr Leu Cys Ala Ala Thr
                100                 105                 110

Leu Thr Gly Gly Tyr Lys Val Val Phe Gly Ser Gly Thr Arg Leu Leu
                115                 120                 125

Val Ser Pro Asp Ile Gln Asn Pro Glu Pro Ala Val Tyr Gln Leu Lys
            130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
                180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser Gly Ser Arg Ala
                260                 265                 270

Lys Arg Ser Gly Ser Gly Ala Thr Asn Phe Ser Leu Leu Lys Gln Ala
            275                 280                 285

Gly Asp Val Glu Glu Asn Pro Gly Pro Arg Met Gly Ser Arg Leu Phe
            290                 295                 300

Leu Val Leu Ser Leu Leu Cys Thr Lys His Met Glu Ala Ala Val Thr
305                 310                 315                 320

Gln Ser Pro Arg Asn Lys Val Thr Val Thr Gly Gly Asn Val Thr Leu
                325                 330                 335

Ser Cys Arg Gln Thr Asn Ser His Asn Tyr Met Tyr Trp Tyr Arg Gln
                340                 345                 350

Asp Thr Gly His Gly Leu Arg Leu Ile His Tyr Ser Tyr Gly Ala Gly
                355                 360                 365

Asn Leu Gln Ile Gly Asp Val Pro Asp Gly Tyr Lys Ala Thr Arg Thr
            370                 375                 380

Thr Gln Glu Asp Phe Phe Leu Leu Leu Glu Leu Ala Ser Pro Ser Gln
385                 390                 395                 400

Thr Ser Leu Tyr Phe Cys Ala Ser Ser Asp Ala Gly Thr Ser Gln Asn
                405                 410                 415

Thr Leu Tyr Phe Gly Ala Gly Thr Arg Leu Ser Val Leu Glu Asp Leu
```

```
                420             425             430
Arg Asn Val Thr Pro Pro Lys Val Ser Leu Phe Glu Pro Ser Lys Ala
            435             440             445

Glu Ile Ala Asn Lys Arg Lys Ala Thr Leu Val Cys Leu Ala Arg Gly
450             455             460

Phe Phe Pro Asp His Val Glu Leu Ser Trp Trp Val Asn Gly Lys Glu
465             470             475             480

Val His Ser Gly Val Ser Thr Asp Pro Gln Ala Tyr Lys Glu Ser Asn
            485             490             495

Tyr Ser Tyr Cys Leu Ser Ser Arg Leu Arg Val Ser Ala Thr Phe Trp
            500             505             510

His Asn Pro Arg Asn His Phe Arg Cys Gln Val Gln Phe His Gly Leu
            515             520             525

Ser Glu Glu Asp Lys Trp Pro Glu Gly Ser Pro Lys Pro Val Thr Gln
            530             535             540

Asn Ile Ser Ala Glu Ala Trp Gly Arg Ala Asp Cys Gly Ile Thr Ser
545             550             555             560

Ala Ser Tyr Gln Gln Gly Val Leu Ser Ala Thr Ile Leu Tyr Glu Ile
            565             570             575

Leu Leu Gly Lys Ala Thr Leu Tyr Ala Val Leu Val Ser Thr Leu Val
            580             585             590

Val Met Ala Met Val Lys Arg Lys Asn Ser
            595             600
```

<210> SEQ ID NO 63
<211> LENGTH: 1809
<212> TYPE: DNA
<213> ORGANISM: Artificial Sequence
<220> FEATURE:
<223> OTHER INFORMATION: Synthetic

<400> SEQUENCE: 63

```
atgaaatctt ttagcatctc cctggtcgtc ctgtggctgc agctgaattg ggtgaatagt      60
cagcagaagg tccagcagtc ccccgagtcc ctgatcgtgc ctgagggcgg catggcctct     120
ctgaactgca ccagctccga ccggaatgtg gattatttct ggtggtacag acagcactct     180
ggcaagagcc caaagatgct gatgtccatc ttctctaacg gcgagaagga ggagggccgg     240
tttacagtgc acctgaataa ggctagcctg cacacctccc tgcacatcag agactcccag     300
ccctccgatt ctgccctgta tctgtgcgcc gcctctatca aaacgccta caaagtgatc     360
ttcggcaagg gaacccacct gcacgtgctg cctaacatcc agaatccaga gcccgccgtg     420
tatcagctga aggacccacg gagccaggat agcaccctgt gcctgttcac gactttgat     480
agccagatca atgtgcctaa gacaatggag tccggcacct ttatcacaga caagaccgtg     540
ctggatatga aggccatgga cagcaagtcc aacggcgcca tcgcctggtc taatcagaca     600
agcttcacct gccaggatat ctttaaggag acaaacgcca cctacccatc tagcgacgtg     660
ccctgtgatg ccacccctgac agagaagagc ttcgagacag acatgaacct gaatttttcag     720
aacctgtccg tgatgggcct gagaatcctg ctgctgaagg tggccggctt caatctgctg     780
atgacactgc gcctgtggtc ctctggctct agggcaaagc ggagcggcag cggagcaacc     840
aacttcagcc tgctgaagca ggccggcgat gtggaggaga tcctggcccc acggatgggc     900
tctagactgt ttctggtgct gagcctgctg tgcacaaagc acatggaggc agcagtgacc     960
cagtccccac ggaacaaggt gaccgtgaca ggcggcaatg tgacactgag ctgtagacag    1020
```

| | |
|---|---|
| accaactccc acaattacat gtattggtac cggcaggata ccggacacgg cctgagactg | 1080 |
| atccactata gctacggcgc cggcaatctg cagatcggcg acgtgccaga tggctataag | 1140 |
| gccacaagga ccacacagga ggacttcttt ctgctgctgg agctggcctc ccctctcag | 1200 |
| acctctctgt atttctgcgc cagctccgat gccggcacaa gccagaacac cctgtacttt | 1260 |
| ggagcaggaa caaggctgtc cgtgctggag gacctgcgca atgtgacccc ccctaaggtg | 1320 |
| tccctgttcg agccttctaa ggccgagatc gccaacaaga ggaaggccac cctggtgtgc | 1380 |
| ctggcaaggg gcttctttcc agatcacgtg gagctgtcct ggtgggtgaa tggcaaggag | 1440 |
| gtgcactctg gcgtgagcac agaccccag gcctacaagg agtccaacta ttcttactgc | 1500 |
| ctgtctagcc ggctgagagt gagcgccacc ttttggcaca accccaggaa tcacttccgc | 1560 |
| tgtcaggtgc agtttcacgg cctgtccgag gaggataagt ggcctgaggg ctctcccaag | 1620 |
| cctgtgacac agaacatcag cgccgaggca tggggaaggg cagactgtgg catcaccagc | 1680 |
| gcctcctatc agcagggcgt gctgagcgcc acaatcctgt acgagatcct gctgggcaag | 1740 |
| gccaccctgt atgctgtgct ggtgtcaact ctggtggtca tggctatggt gaaacggaaa | 1800 |
| aactcctaa | 1809 |

<210> SEQ ID NO 64
<211> LENGTH: 1809
<212> TYPE: DNA
<213> ORGANISM: Artificial Sequence
<220> FEATURE:
<223> OTHER INFORMATION: Synthetic

<400> SEQUENCE: 64

| | |
|---|---|
| atgaaatctt ttagcatctc cctggtcgtc ctgtggctgc agctgaattg ggtgaatagt | 60 |
| cagcagaagg tccagcagtc ccccgagtcc ctgatcgtgc ctgagggcgg catggcctct | 120 |
| ctgaactgca ccagctccga ccggaatgtg gattatttct ggtggtacag acagcactct | 180 |
| ggcaagagcc caaagatgct gatgtccatc ttctctaacg gcgagaagga ggagggccgg | 240 |
| tttacagtgc acctgaataa ggctagcctg cacacctccc tgcacatcag agactcccag | 300 |
| ccctccgatt ctgccctgta tctgtgcgcc gcctctaccg tgaacgccta caaagtgatc | 360 |
| ttcggcaagg gaacccacct gcacgtgctg cctaacatcc agaatccaga gcccgccgtg | 420 |
| tatcagctga aggacccacg gagccaggat agcaccctgt gcctgttcac cgactttgat | 480 |
| agccagatca atgtgcctaa gacaatggag tccggcacct ttatcacaga caagaccgtg | 540 |
| ctggatatga aggccatgga cagcaagtcc aacggcgcca tcgcctggtc taatcagaca | 600 |
| agcttcacct gccaggatat ctttaaggag acaaacgcca cctacccatc tagcgacgtg | 660 |
| ccctgtgatg ccaccctgac agagaagagc ttcgagacag acatgaacct gaattttcag | 720 |
| aacctgtccg tgatgggcct gagaatcctg ctgctgaagg tggccggctt caatctgctg | 780 |
| atgacactgc gcctgtggtc ctctggctct agggcaaagc ggagcggcag cggagcaacc | 840 |
| aacttcagcc tgctgaagca ggccggcgat gtggaggaga tcctggccc acggatgggc | 900 |
| tctagactgt ttctggtgct gagcctgctg tgcacaaagc acatggaggc agcagtgacc | 960 |
| cagtcccac ggaacaaggt gaccgtgaca ggcggcaatg tgacactgag ctgtagacag | 1020 |
| accaactccc acaattacat gtattggtac cggcaggata ccggacacgg cctgagactg | 1080 |
| atccactata gctacggcgc cggcaatctg cagatcggcg acgtgccaga tggctataag | 1140 |
| gccacaagga ccacacagga ggacttcttt ctgctgctgg agctggcctc ccctctcag | 1200 |
| acctctctgt atttctgcgc cagctccgat gccggcacaa gccagaacac cctgtacttt | 1260 |

| | |
|---|---|
| ggagcaggaa caaggctgtc cgtgctggag gacctgcgca atgtgacccc ccctaaggtg | 1320 |
| tccctgttcg agccttctaa ggccgagatc gccaacaaga ggaaggccac cctggtgtgc | 1380 |
| ctggcaaggg gcttctttcc agatcacgtg gagctgtcct ggtgggtgaa tggcaaggag | 1440 |
| gtgcactctg gcgtgagcac agaccccag gcctacaagg agtccaacta ttcttactgc | 1500 |
| ctgtctagcc ggctgagagt gagcgccacc ttttggcaca accccaggaa tcacttccgc | 1560 |
| tgtcaggtgc agtttcacgg cctgtccgag gaggataagt ggcctgaggg ctctcccaag | 1620 |
| cctgtgacac agaacatcag cgccgaggca tggggaaggg cagactgtgg catcaccagc | 1680 |
| gcctcctatc agcagggcgt gctgagcgcc acaatcctgt acgagatcct gctgggcaag | 1740 |
| gccaccctgt atgctgtgct ggtgtcaact ctggtggtca tggctatggt gaaacggaaa | 1800 |
| aactcctaa | 1809 |

<210> SEQ ID NO 65
<211> LENGTH: 1809
<212> TYPE: DNA
<213> ORGANISM: Artificial Sequence
<220> FEATURE:
<223> OTHER INFORMATION: Synthetic

<400> SEQUENCE: 65

| | |
|---|---|
| atgaaatctt ttagcatctc cctggtcgtc ctgtggctgc agctgaattg ggtgaatagt | 60 |
| cagcagaagg tccagcagtc ccccgagtcc ctgatcgtgc ctgagggcgg catggcctct | 120 |
| ctgaactgca ccagctccga ccggaatgtg gattatttct ggtggtacag acagcactct | 180 |
| ggcaagagcc caaagatgct gatgtccatc ttctctaacg gcgagaagga ggagggccgg | 240 |
| tttacagtgc acctgaataa ggctagcctg cacacctccc tgcacatcag agactcccag | 300 |
| ccctccgatt ctgccctgta tctgtgcgcc gcctctatgg ccggcggcta caaagtggtg | 360 |
| ttcggcagcg gaacccggct gctggtgagc cctgacatcc agaatccaga gcccgccgtg | 420 |
| tatcagctga aggacccacg gagccaggat agcaccctgt gcctgttcac cgactttgat | 480 |
| agccagatca atgtgcctaa gacaatggag tccggcacct ttatcacaga caagaccgtg | 540 |
| ctggatatga aggccatgga cagcaagtcc aacgcgcca tcgcctggtc taatcagaca | 600 |
| agcttcacct gccaggatat ctttaaggag acaaacgcca cctacccatc tagcgacgtg | 660 |
| ccctgtgatg ccaccctgac agagaagagc ttcgagacag acatgaacct gaattttcag | 720 |
| aacctgtccg tgatgggcct gagaatcctg ctgctgaagg tggccggctt caatctgctg | 780 |
| atgacactgc gcctgtggtc ctctggctct agggcaaagc ggagcggcag cggagcaacc | 840 |
| aacttcagcc tgctgaagca ggccggcgat gtggaggaga tcctggcccc acggatgggc | 900 |
| tctagactgt ttctggtgct gagcctgctg tgcacaaagc acatggaggc agcagtgacc | 960 |
| cagtccccac ggaacaaggt gaccgtgaca ggcggcaatg tgacactgag ctgtagacag | 1020 |
| accaactccc acaattacat gtattggtac cggcaggata ccggacacgg cctgagactg | 1080 |
| atccactata gctacggcgc cggcaatctg cagatcggcg acgtgccaga tggctataag | 1140 |
| gccacaagga ccacacagga ggacttcttt ctgctgctgg agctggcctc ccctctcag | 1200 |
| acctctctgt atttctgcgc cagctccgat gccggcacag cccagaacac cctgtacttt | 1260 |
| ggagcaggaa caaggctgtc cgtgctggag gacctgcgca atgtgacccc ccctaaggtg | 1320 |
| tccctgttcg agccttctaa ggccgagatc gccaacaaga ggaaggccac cctggtgtgc | 1380 |
| ctggcaaggg gcttctttcc agatcacgtg gagctgtcct ggtgggtgaa tggcaaggag | 1440 |

```
gtgcactctg gcgtgagcac agacccccag gcctacaagg agtccaacta ttcttactgc    1500
ctgtctagcc ggctgagagt gagcgccacc ttttggcaca accccaggaa tcacttccgc    1560
tgtcaggtgc agtttcacgg cctgtccgag gaggataagt ggcctgaggg ctctcccaag    1620
cctgtgacac agaacatcag cgccgaggca tggggaaggg cagactgtgg catcaccagc    1680
gcctcctatc agcagggcgt gctgagcgcc acaatcctgt acgagatcct gctgggcaag    1740
gccaccctgt atgctgtgct ggtgtcaact ctggtggtca tggctatggt gaaacggaaa    1800
aactcctaa                                                            1809

<210> SEQ ID NO 66
<211> LENGTH: 1809
<212> TYPE: DNA
<213> ORGANISM: Artificial Sequence
<220> FEATURE:
<223> OTHER INFORMATION: Synthetic

<400> SEQUENCE: 66
atgaagtcct tctctatcag cctggtggtg ctgtggctgc agctgaactg ggtgaatagc      60
cagcagaagg tgcagcagtc tcctgagagc ctgatcgtgc cagagggcgg catggcctcc     120
ctgaactgca ccagctccga ccggaatgtg gattattttt ggtggtacag acagcactcc     180
ggcaagtctc ccaagatgct gatgagcatc ttctccaacg gcgagaagga ggagggccgg     240
tttacagtgc acctgaataa ggcctctctg cacaccagcc tgcacatcag agactcccag     300
ccttccgatt ctgccctgta tctgtgcgcc gcctctatga tcaatgccta caaagtgatc     360
ttcggcaagg gcacacacct gcacgtgctg cccaacatcc agaatccaga gcccgccgtg     420
tatcagctga aggaccctcg gtctcaggat agcaccctgt gcctgttcac cgactttgat     480
agccagatca tgtgccaaa gaccatggag tccggcacct ttatcacaga caagaccgtg     540
ctggatatga aggccatgga cagcaagtcc aacggcgcca tcgcctggtc caatcagaca     600
tctttcacct gccaggatat ctttaaggag acaaacgcca cctacccatc tagcgacgtg     660
ccctgtgatg ccaccctgac agagaagagc ttcgagaccg acatgaacct gaattttcag     720
aacctgtccg tgatgggcct gagaatcctg ctgctgaagg tggccggctt caatctgctg     780
atgacactgc gcctgtggtc ctctggctct agggcaaagc ggagcggcag cggagcaacc     840
aacttcagcc tgctgaagca ggccggcgat gtggaggaga tcctggccc acggatgggc     900 tccagactgt ttctggtgct gtctctgctg tgcacaaagc acatggaggc agcagtgacc     960
cagagcccac ggaacaaggt gaccgtgaca ggcggcaatg tgacactgtc ttgtagacag    1020
accaacagcc acaattacat gtattggtac cggcaggata ccggacacgg cctgagactg    1080
atccactatt cctacggagc aggaaacctg cagatcggcg acgtgcctga tggctacaag    1140
gccacaagaa ccacacagga ggacttcttt ctgctgctgg agctggcctc cccatctcag    1200
acctctctgt atttctgcgc aagctccgat gcaggcgtga ccagaacac actgtacttt    1260 ggagcaggaa ccaggctgag cgtgctggag gacctgcgca atgtgacacc ccctaaggtg    1320
agcctgttcg agccctccaa ggccgagatc gccaacaaga ggaaggccac cctggtgtgc    1380
ctggcaaggg gcttctttcc tgatcacgtg gagctgagct ggtgggtgaa tggcaaggag    1440
gtgcactccg gcgtgtctac agacccacag gcctataagg agagcaacta ttcctactgc    1500
ctgtctagcc ggctgagagt gtccgccacc ttttggcaca acccaaggaa tcacttccgc    1560
tgtcaggtgc agtttcacgg cctgagcgag gaggataagt ggccagaggg ctccccaaag    1620
cctgtgaccc agaatatctc tgccgaggca tggggaaggg cagactgtgg aatcacaagc    1680
```

| | |
|---|---|
| gcctcctacc agcagggcgt gctgtccgcc accatcctgt atgagatcct gctgggcaag | 1740 |
| gccacactgt acgccgtgct ggtgtccacc ctggtggtca tggccatggt gaagcgcaag | 1800 |
| aactcttga | 1809 |

<210> SEQ ID NO 67
<211> LENGTH: 1809
<212> TYPE: DNA
<213> ORGANISM: Artificial Sequence
<220> FEATURE:
<223> OTHER INFORMATION: Synthetic

<400> SEQUENCE: 67

| | |
|---|---|
| atgaagtcct tctctatcag cctggtggtg ctgtggctgc agctgaactg ggtgaattct | 60 |
| cagcagaagg tgcagcagtc ccctgagtct ctgatcgtgc cagagggcgg catggcctcc | 120 |
| ctgaactgca ccagctccga ccggaatgtg gattattttt ggtggtacag acagcacagc | 180 |
| ggcaagtccc ccaagatgct gatgtctatc ttcagcaacg gcgagaagga ggagggccgg | 240 |
| tttacagtgc acctgaataa ggcctccctg cacacctctc tgcacatcag agacagccag | 300 |
| ccttccgatt ctgccctgta tctgtgcgca gcaagcatct ccggaggata caaggtggtg | 360 |
| ttcggcagcg gaacaaggct gctggtgtcc cccgatatcc agaatccaga gcccgccgtg | 420 |
| tatcagctga aggaccctcg ctcccaggat agcaccctgt gcctgttcac cgactttgat | 480 |
| tcccagatca acgtgccaaa gaccatggag tctggcacct ttatcacaga caagaccgtg | 540 |
| ctggatatga aggccatgga ctctaagagc aacggcgcca tcgcctggag caatcagaca | 600 |
| tccttcacct gccaggatat ctttaaggag acaaatgcca cctacccatc tagcgacgtg | 660 |
| ccctgtgatg ccacccctga cagagaagtct ttcgagaccg acatgaacct gaattttcag | 720 |
| aacctgagcg tgatgggcct gagaatcctg ctgctgaagg tggccggctt caatctgctg | 780 |
| atgacactga gctgtggtc ctctggctcc agggcaaagc ggagcggctc tggagccacc | 840 |
| aacttctctc tgctgaagca ggcaggcgac gtggaggaga tcctggacc acggatgggc | 900 |
| tctagactgt ttctggtgct gagcctgctg tgcacaaagc acatggaggc agcagtgacc | 960 |
| cagagcccac ggaacaaggt gaccgtgaca ggcggcaatg tgacactgtc ctgtagacag | 1020 |
| accaactctc acaattacat gtattggtac cggcaggata ccggccacgg cctgagactg | 1080 |
| atccactatt cctacggagc aggaaacctg cagatcggcg acgtgcctga tggctacaag | 1140 |
| gccacaagga ccacacagga ggacttcttt ctgctgctgg agctggccag cccatcccag | 1200 |
| accagcctgt atttctgcgc cagctccgat gccggcacat cccagaacac cctgtacttt | 1260 |
| ggagcaggaa caaggctgag cgtgctggag gacctgcgca atgtgacccc ccctaaggtg | 1320 |
| tctctgttcg agcccagcaa ggccgagatc gccaacaaga ggaaggccac cctggtgtgc | 1380 |
| ctggcaaggg gcttctttcc tgatcacgtg agctgagct ggtgggtgaa tggcaaggag | 1440 |
| gtgcacagcg gcgtgtccac agacccacag gcctataagg agtctaacta tagctactgc | 1500 |
| ctgtctagcc ggctgagagt gtccgccacc ttttggcaca acccaaggaa tcacttccgc | 1560 |
| tgtcaggtgc agtttcacgg cctgtccgag gaggataagt ggccagaggg ctctccaaag | 1620 |
| cctgtgaccc agaatatcag cgccgaggca tgggaaggg cagactgtgg catcacatct | 1680 |
| gccagctacc agcagggcgt gctgtccgcc accatcctgt atgagatcct gctgggcaag | 1740 |
| gccacactgt acgccgtgct ggtgagcacc ctggtggtca tggccatggt gaagagaaag | 1800 |
| aactcctga | 1809 |

<210> SEQ ID NO 68
<211> LENGTH: 1809
<212> TYPE: DNA
<213> ORGANISM: Artificial Sequence
<220> FEATURE:
<223> OTHER INFORMATION: Synthetic

<400> SEQUENCE: 68

| | | | | | |
|---|---|---|---|---|---|
| atgaagtcct | tctctatcag | cctggtggtg | ctgtggctgc | agctgaactg | ggtgaatagc | 60 |
| cagcagaagg | tgcagcagtc | tcctgagagc | ctgatcgtgc | cagagggcgg | catggcctcc | 120 |
| ctgaactgca | ccagctccga | ccggaatgtg | gattattttt | ggtggtacag | acagcactcc | 180 |
| ggcaagtctc | ccaagatgct | gatgagcatc | ttctccaacg | gcgagaagga | ggagggccgg | 240 |
| tttacagtgc | acctgaataa | ggcctctctg | cacaccagcc | tgcacatcag | agactcccag | 300 |
| ccttccgatt | ctgccctgta | tctgtgcgcc | gcctctatcg | tgggcggcta | caaggtggtg | 360 |
| ttcggctccg | gcacaaggct | gctggtgtct | cccgatatcc | agaatccaga | gcccgccgtg | 420 |
| tatcagctga | aggaccctcg | ctctcaggat | agcaccctgt | gcctgttcac | cgactttgat | 480 |
| tctcagatca | acgtgccaaa | gaccatggag | agcggcacct | ttatcacaga | caagaccgtg | 540 |
| ctggatatga | aggccatgga | cagcaagtcc | aacgccgcca | tcgcctggtc | caatcagaca | 600 |
| tctttcacct | gccaggatat | ctttaaggag | acaaatgcca | cctacccatc | tagcgacgtg | 660 |
| ccctgtgatg | ccaccctgac | agagaagagc | ttcgagaccg | acatgaacct | gaattttcag | 720 |
| aacctgtccg | tgatgggcct | gagaatcctg | ctgctgaagg | tggccggctt | caatctgctg | 780 |
| atgacactgc | gcctgtggtc | ctctggctct | agggcaaagc | ggagcggcag | cggagcaacc | 840 |
| aacttcagcc | tgctgaagca | ggcaggcgac | gtggaggaga | tcctggaccc | acggatgggc | 900 |
| agcagactgt | ttctggtgct | gtccctgctg | tgcacaaagc | acatggaggc | agcagtgacc | 960 |
| cagagcccac | ggaacaaggt | gaccgtgaca | ggcggcaatg | tgacactgtc | ttgtagacag | 1020 |
| accaacagcc | acaattacat | gtattggtac | cggcaggata | ccggccacgg | cctgagactg | 1080 |
| atccactatt | cctacggagc | aggaaacctg | cagatcggcg | acgtgcctga | tgctacaagg | 1140 |
| gccacaagga | ccacacagga | ggacttcttt | ctgctgctgg | agctggcctc | cccatctcag | 1200 |
| accagcctgt | atttctgcgc | cagctccgat | cacggcacag | gccagaacac | cctgtacttt | 1260 |
| ggagcaggaa | caaggctgtc | cgtgctggag | gacctgcgca | atgtgacccc | cctaaggtg | 1320 |
| agcctgttcg | agccctccaa | ggccgagatc | gccaacaaga | ggaaggccac | cctggtgtgc | 1380 |
| ctggcaaggg | gcttctttcc | tgatcacgtg | gagctgagct | ggtgggtgaa | tggcaaggag | 1440 |
| gtgcactccg | gcgtgtctac | agacccacag | gcctataagg | agagcaacta | ttcctactgc | 1500 |
| ctgtctagcc | ggctgagagt | gtccgccacc | ttttggcaca | cccaaggaa | tcacttccgc | 1560 |
| tgtcaggtgc | agtttcacgg | cctgtctgag | gaggataagt | ggccagaggg | cagcccaaag | 1620 |
| cctgtgaccc | agaatatctc | cgccgaggca | tggggaaggg | cagactgtgg | aatcacaagc | 1680 |
| gcctcctacc | agcagggcgt | gctgagcgcc | accatcctgt | atgagatcct | gctgggcaag | 1740 |
| gccacactgt | acgccgtgct | ggtgtccacc | ctggtggtca | tggccatggt | gaagagaaag | 1800 |
| aactcttga | | | | | | 1809 |

<210> SEQ ID NO 69
<211> LENGTH: 1809
<212> TYPE: DNA
<213> ORGANISM: Artificial Sequence
<220> FEATURE:
<223> OTHER INFORMATION: Synthetic

<400> SEQUENCE: 69

```
atgaagtcct tctctatcag cctggtggtg ctgtggctgc agctgaactg ggtgaatagc      60
cagcagaagg tgcagcagtc tcctgagagc ctgatcgtgc agagggcgg catggcctcc     120
ctgaactgca ccagctccga ccggaatgtg gattatttt ggtggtacag acagcactcc     180
ggcaagtctc ccaagatgct gatgagcatc ttctccaacg gcgagaagga ggagggccgg     240
tttacagtgc acctgaataa ggcctctctg cacaccagcc tgcacatcag agacagccag     300
ccttccgatt ctgccctgta tctgtgcgcc gcctccaaga caggcggcta caaggtggtg     360
ttcggctccg gaaccaggct gctggtgtct cccgatatcc agaatccaga gcccgccgtg     420
tatcagctga aggaccctcg ctctcaggat agcaccctgt gcctgttcac cgactttgat     480
tctcagatca acgtgccaaa gacaatggag agcggcacct ttatcacaga caagaccgtg     540
ctggatatga aggccatgga cagcaagtcc aacggcgcca tcgcctggtc caatcagaca     600
tctttcacct gccaggatat ctttaaggag acaaatgcca cctacccatc tagcgacgtg     660
ccctgtgatg ccaccctgac agagaagtct ttcgagaccg acatgaacct gaattttcag     720
aacctgagcg tgatgggcct gagaatcctg ctgctgaagg tggccggctt caatctgctg     780
atgacactga ggctgtggtc ctctggctcc agggcaaagc ggagcggcag cggagcaacc     840
aacttctctc tgctgaagca ggcaggcgac gtggaggaga tcctggacc acggatgggc     900
agcagactgt ttctggtgct gtccctgctg tgcacaaagc acatggaggc agcagtgacc     960
cagagcccac ggaacaaggt gaccgtgaca ggcggcaatg tgacactgtc ttgtagacag    1020
accaacagcc acaattacat gtattggtac cggcaggata ccggccacgg cctgagactg    1080
atccactatt cctacggagc aggaaacctg cagatcggcg acgtgcctga tggctacaag    1140
gccacaagga ccacacagga ggacttctt ctgctgctgg agctggcctc cccatctcag    1200
acctccctgt atttctgcgc cagctccgat gccggcacat tcagaacac cctgtacttt    1260
ggagcaggaa caaggctgag cgtgctggag gacctgcgca atgtgacccc ccctaaggtg    1320
agcctgttcg agccctccaa ggccgagatc gccaacaaga ggaaggccac cctggtgtgc    1380
ctggcaaggg gcttctttcc tgatcacgtg agctgagct ggtgggtgaa tggcaaggag    1440
gtgcactccg gcgtgtctac agaccccaca gcctataagg agagcaacta ttcctactgc    1500
ctgtctagcc ggctgagagt gtccgccacc ttttggcaca acccaaggaa tcacttccgc    1560
tgtcaggtgc agtttcacgg cctgtctgag gaggataagt ggccagaggg cagcccaaag    1620
cctgtgaccc agaatatctc cgccgaggca tggggaaggg cagactgtgg aatcacaagc    1680
gcctcctacc agcagggcgt gctgagcgcc accatcctgt atgagatcct gctgggcaag    1740
gccacactgt acgccgtgct ggtgagcacc ctggtggtca tggccatggt gaagagaaag    1800
aactcctga                                                              1809
```

<210> SEQ ID NO 70
<211> LENGTH: 1809
<212> TYPE: DNA
<213> ORGANISM: Artificial Sequence
<220> FEATURE:
<223> OTHER INFORMATION: Synthetic

<400> SEQUENCE: 70

```
atgaaatcct ttagtatttc cctagtggtc ctgtggcttc agctaaactg ggtgaacagc      60
caacagaagg tgcagcagag cccagaatcc ctcattgttc agagggagg catggcctct     120
```

```
ctcaactgca cttccagtga tcgtaatgtt gactacttct ggtggtacag acagcactct    180
gggaaaagcc ccaagatgct gatgtctatc ttctccaatg gtgaaaagga agaaggcaga    240
ttcacagttc acctcaataa agccagcctg catacttccc tgcacatcag agactcccag    300
cccagtgact ctgctctcta cctctgtgca gcaagcatga ctggaggcta taaagtggtc    360
tttggaagtg ggactcgatt gctggtaagc cctgacatcc agaacccaga acctgctgtg    420
taccagttaa agatcctcg gtctcaggac agcaccctct gcctgttcac cgactttgac    480
tcccaaatca atgtgccgaa aaccatggaa tctggaacgt tcatcactga caaaactgtg    540
ctggacatga agctatgga ttccaagagc aatggggcca ttgcctggag caaccagaca    600
agcttcacct gccaagatat cttcaaagag accaacgcca cctaccccag ttcagacgtt    660
ccctgtgatg ccacgttgac tgagaaaagc tttgaaacag atatgaacct aaactttcaa    720
aacctgtcag ttatgggact ccgaatcctc ctgctgaaag tagccggatt taacctgctc    780
atgacgctga ggctgtggtc cagtggcagc agagccaaga aagcggatc cggcgccacc    840 aacttcagcc tgctgaagca ggccggcgac gtggaggaaa accctggccc taggatgggc    900
tccaggctct ttctggtctt gagcctcctg tgtacaaaac acatggaggc tgcagtcacc    960
caaagcccta gaaacaaggt gacagtaaca ggaggaaacg tgacattgag ctgtcgccag    1020
actaatagcc acaactacat gtactggtat cggcaggaca ctgggcatgg gctgaggctg    1080
atccattact catatggtgc tggcaacctt caaataggga tgtccctga tgggtacaag    1140 gccaccagaa caacgcaaga agacttcttc ctcctgctgg aattggcttc tccctctcag    1200
acatctttgt acttctgtgc cagcagtgat gcagggacaa gtcaaaacac cttgtacttt    1260
ggtgcgggca cccgactatc ggtgctagag gatctgagaa atgtgactcc acccaaggtc    1320
tccttgtttg agccatcaaa agcagagatt gcaaacaaac gaaaggctac cctcgtgtgc    1380
ttggccaggg gcttcttccc tgaccacgtg gagctgagct ggtgggtgaa tggcaaggag    1440
gtccacagtg gggtcagcac ggaccctcag gcctacaagg agagcaatta tagctactgc    1500
ctgagcagcc gcctgagggt ctctgctacc ttctggcaca atcctcgaaa ccacttccgc    1560
tgccaagtgc agttccatgg ctttcagag gaggacaagt ggcagagggg ctcacccaaa    1620
cctgtcacac agaacatcag tgcagaggcc tggggccgag cagactgtgg gattacctca    1680
gcatcctatc aacaagggt cttgtctgcc accatcctct atgagatcct gctagggaaa    1740 gccacccctgt atgctgtgct tgtcagtaca ctggtggtga tggctatggt caaaagaaag    1800
aattcatga                                                           1809
```

<210> SEQ ID NO 71
<211> LENGTH: 1809
<212> TYPE: DNA
<213> ORGANISM: Artificial Sequence
<220> FEATURE:
<223> OTHER INFORMATION: Synthetic

<400> SEQUENCE: 71

```
atgaaatcct ttagtatttc cctagtggtc ctgtggcttc agctaaactg ggtgaacagc     60
caacagaagg tgcagcagag cccagaatcc ctcattgttc cagagggagg catggcctct    120
ctcaactgca cttccagtga tcgtaatgtt gactacttct ggtggtacag acagcactct    180
gggaaaagcc ccaagatgct gatgtctatc ttctccaatg gtgaaaagga agaaggcaga    240
ttcacagttc acctcaataa agccagcctg catacttccc tgcacatcag agactcccag    300
cccagtgact ctgctctcta cctctgtgca gcaaccctga ctggaggcta taaagtggtc    360
```

```
tttggaagtg ggactcgatt gctggtaagc cctgacatcc agaacccaga acctgctgtg      420
taccagttaa aagatcctcg gtctcaggac agcaccctct gcctgttcac cgactttgac      480
tcccaaatca atgtgccgaa accatggaa tctggaacgt tcatcactga caaaactgtg       540
ctggacatga aagctatgga ttccaagagc aatggggcca ttgcctggag caaccagaca      600
agcttcacct gccaagatat cttcaaagag accaacgcca cctacccag ttcagacgtt       660 ccctgtgatg ccacgttgac tgagaaaagc tttgaaacag atatgaacct aaactttcaa      720
aacctgtcag ttatgggact ccgaatcctc ctgctgaaag tagccggatt taacctgctc      780
atgacgctga ggctgtggtc cagtggcagc agagccaaga gaagcggatc cggcgccacc      840
aacttcagcc tgctgaagca ggccggcgac gtggaggaaa accctggccc taggatgggc      900
tccaggctct ttctggtctt gagcctcctg tgtacaaaac acatggaggc tgcagtcacc      960
caaagcccta gaaacaaggt gacagtaaca ggaggaaacg tgacattgag ctgtcgccag     1020
actaatagcc acaactacat gtactggtat cggcaggaca ctgggcatgg gctgaggctg     1080
atccattact catatggtgc tggcaacctt caaataggag atgtccctga tgggtacaag     1140
gccaccagaa caacgcaaga agacttcttc ctcctgctgg aattggcttc tccctctcag     1200
acatctttgt acttctgtgc cagcagtgat gctgggacta gtcaaaacac cttgtacttt     1260
ggtgcgggca cccgactatc ggtgctagag gatctgagaa atgtgactcc acccaaggtc     1320
tccttgtttg agccatcaaa agcagagatt gcaaacaaac gaaaggctac cctcgtgtgc     1380
ttggccaggg gcttcttccc tgaccacgtg gagctgagct ggtgggtgaa tggcaaggag     1440
gtccacagtg gggtcagcac ggaccctcag gcctacaagg agagcaatta tagctactgc     1500
ctgagcagcc gcctgaggt ctctgctacc ttctggcaca atcctcgaaa ccacttccgc      1560
tgccaagtgc agttccatgg gctttcagag gaggacaagt ggccagaggg ctcacccaaa     1620
cctgtcacac agaacatcag tgcagaggcc tggggccgag cagactgtgg gattacctca     1680
gcatcctatc aacaagggt cttgtctgcc accatcctct atgagatcct gctagggaaa      1740
gccaccctgt atgctgtgct tgtcagtaca ctggtggtga tggctatggt caaaagaaag     1800
aattcatga                                                             1809
```

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Gly Ile Leu Gly Phe Val Phe Thr Leu
1               5

<210> SEQ ID NO 73
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: n= I
<220> FEATURE:
<221> NAME/KEY: misc_feature
<222> LOCATION: (13)..(14)
<223> OTHER INFORMATION: n= I

```
<220> FEATURE:
<221> NAME/KEY: misc_feature
<222> LOCATION: (18)..(19)
<223> OTHER INFORMATION: n= I

<400> SEQUENCE: 73
caccgggnng ggnngggnng g                                              21

<210> SEQ ID NO 74
<211> LENGTH: 16
<212> TYPE: DNA
<213> ORGANISM: Artificial Sequence
<220> FEATURE:
<223> OTHER INFORMATION: Synthetic

<400> SEQUENCE: 74
ggcatcacag ggaacg                                                    16

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ccagaaggta gcagagaccc                                                20

<210> SEQ ID NO 76
<211> LENGTH: 22
<212> TYPE: DNA
<213> ORGANISM: Artificial Sequence
<220> FEATURE:
<223> OTHER INFORMATION: Synthetic

<400> SEQUENCE: 76
atgaaatcct ttagtatttc cc                                             22

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
atgggctcca ggctctttct g                                              21

<210> SEQ ID NO 78
<211> LENGTH: 19
<212> TYPE: DNA
<213> ORGANISM: Artificial Sequence
<220> FEATURE:
<223> OTHER INFORMATION: Synthetic

<400> SEQUENCE: 78
gcacattgat ttgggagtc                                                 19

<210> SEQ ID NO 79
<211> LENGTH: 21
<212> TYPE: DNA
<213> ORGANISM: Artificial Sequence
<220> FEATURE:
<223> OTHER INFORMATION: Synthetic

<400> SEQUENCE: 79
```
gggtagcctt ttgtttgttt g                                                21

<210> SEQ ID NO 80
<211> LENGTH: 117
<212> TYPE: PRT
<213> ORGANISM: Artificial Sequence
<220> FEATURE:
<223> OTHER INFORMATION: Synthetic

<400> SEQUENCE: 80

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Ile Thr Asn Ala
                85                  90                  95

Tyr Lys Val Ile Phe Gly Lys Gly Thr His Leu His Val Leu Pro Asn
            100                 105                 110

Ile Gln Asn Pro Glu
        115

<210> SEQ ID NO 81
<211> LENGTH: 117
<212> TYPE: PRT
<213> ORGANISM: Artificial Sequence
<220> FEATURE:
<223> OTHER INFORMATION: Synthetic

<400> SEQUENCE: 81

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Thr Val Asn Ala
                85                  90                  95

Tyr Lys Val Ile Phe Gly Lys Gly Thr His Leu His Val Leu Pro Asn
            100                 105                 110

Ile Gln Asn Pro Glu
        115

<210> SEQ ID NO 82
<211> LENGTH: 117
<212> TYPE: PRT
<213> ORGANISM: Artificial Sequence
<220> FEATURE:
<223> OTHER INFORMATION: Synthetic

<400> SEQUENCE: 82

-continued

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Gly Arg Phe Thr Val His
        50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Ile Asn Ala
                85                  90                  95

Tyr Lys Val Ile Phe Gly Lys Gly Thr His Leu His Val Leu Pro Asn
                100                 105                 110

Ile Gln Asn Pro Glu
        115

<210> SEQ ID NO 83
<211> LENGTH: 117
<212> TYPE: PRT
<213> ORGANISM: Artificial Sequence
<220> FEATURE:
<223> OTHER INFORMATION: Synthetic

<400> SEQUENCE: 83

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Gly Arg Phe Thr Val His
        50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Ala Gly Gly
                85                  90                  95

Tyr Lys Val Val Phe Gly Ser Gly Thr Arg Leu Leu Val Ser Pro Asp
                100                 105                 110

Ile Gln Asn Pro Glu
        115

<210> SEQ ID NO 84
<211> LENGTH: 117
<212> TYPE: PRT
<213> ORGANISM: Artificial Sequence
<220> FEATURE:
<223> OTHER INFORMATION: Synthetic

<400> SEQUENCE: 84

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Gly Arg Phe Thr Val His

```
                50                  55                  60
Leu Asn Lys Ala Ser Leu His Thr Ser Leu His Ile Arg Asp Ser Gln
 65                  70                  75                  80

Pro Ser Asp Ser Ala Leu Tyr Leu Cys Ala Ala Ser Ile Ser Gly Gly
                    85                  90                  95

Tyr Lys Val Val Phe Gly Ser Gly Thr Arg Leu Leu Val Ser Pro Asp
                100                 105                 110

Ile Gln Asn Pro Glu
            115

<210> SEQ ID NO 85
<211> LENGTH: 117
<212> TYPE: PRT
<213> ORGANISM: Artificial Sequence
<220> FEATURE:
<223> OTHER INFORMATION: Synthetic

<400> SEQUENCE: 85

Gln Gln Lys Val Gln Gln Ser Pro Glu Ser Leu Ile Val Pro Glu Gly
 1               5                  10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Gly Arg Phe Thr Val His
        50                  55                  60

Leu Asn Lys Ala Ser Leu His Thr Ser Leu His Ile Arg Asp Ser Gln
 65                  70                  75                  80

Pro Ser Asp Ser Ala Leu Tyr Leu Cys Ala Ala Ser Ile Val Gly Gly
                    85                  90                  95

Tyr Lys Val Val Phe Gly Ser Gly Thr Arg Leu Leu Val Ser Pro Asp
                100                 105                 110

Ile Gln Asn Pro Glu
            115

<210> SEQ ID NO 86
<211> LENGTH: 117
<212> TYPE: PRT
<213> ORGANISM: Artificial Sequence
<220> FEATURE:
<223> OTHER INFORMATION: Synthetic

<400> SEQUENCE: 86

Gln Gln Lys Val Gln Gln Ser Pro Glu Ser Leu Ile Val Pro Glu Gly
 1               5                  10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Gly Arg Phe Thr Val His
        50                  55                  60

Leu Asn Lys Ala Ser Leu His Thr Ser Leu His Ile Arg Asp Ser Gln
 65                  70                  75                  80

Pro Ser Asp Ser Ala Leu Tyr Leu Cys Ala Ala Ser Lys Thr Gly Gly
                    85                  90                  95

Tyr Lys Val Val Phe Gly Ser Gly Thr Arg Leu Leu Val Ser Pro Asp
                100                 105                 110
```

Ile Gln Asn Pro Glu
        115

<210> SEQ ID NO 87
<211> LENGTH: 117
<212> TYPE: PRT
<213> ORGANISM: Artificial Sequence
<220> FEATURE:
<223> OTHER INFORMATION: Synthetic

<400> SEQUENCE: 87

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Glu Gly Arg Phe Thr Val His
        50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Ser Met Thr Gly Gly
                85                  90                  95

Tyr Lys Val Val Phe Gly Ser Gly Thr Arg Leu Leu Val Ser Pro Asp
                100                 105                 110

Ile Gln Asn Pro Glu
        115

<210> SEQ ID NO 88
<211> LENGTH: 117
<212> TYPE: PRT
<213> ORGANISM: Artificial Sequence
<220> FEATURE:
<223> OTHER INFORMATION: Synthetic

<400> SEQUENCE: 88

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
                20                  25                  30

Phe Trp Trp Tyr Arg Gln His Ser Gly Lys Ser Pro Lys Met Leu Met
            35                  40                  45

Ser Ile Phe Ser Asn Gly Glu Lys Glu Glu Gly Arg Phe Thr Val His
        50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Thr Leu Thr Gly Gly
                85                  90                  95

Tyr Lys Val Val Phe Gly Ser Gly Thr Arg Leu Leu Val Ser Pro Asp
                100                 105                 110

Ile Gln Asn Pro Glu
        115

<210> SEQ ID NO 89
<211> LENGTH: 114
<212> TYPE: PRT
<213> ORGANISM: Artificial Sequence
<220> FEATURE:
<223> OTHER INFORMATION: Synthetic -continued

```
<400> SEQUENCE: 89

Glu Ala Ala Val Thr Gln Ser Pro Arg Asn Lys Val Thr Val Thr Gly
1               5                   10                  15

Gly Asn Val Thr Leu Ser Cys Arg Gln Thr Asn Ser His Asn Tyr Met
            20                  25                  30

Tyr Trp Tyr Arg Gln Asp Thr Gly His Gly Leu Arg Leu Ile His Tyr
        35                  40                  45

Ser Tyr Gly Ala Gly Asn Leu Gln Ile Gly Asp Val Pro Asp Gly Tyr
    50                  55                  60

Lys Ala Thr Arg Thr Thr Gln Glu Asp Phe Phe Leu Leu Leu Glu Leu
65                  70                  75                  80

Ala Ser Pro Ser Gln Thr Ser Leu Tyr Phe Cys Ala Ser Ser Asp Ala
                85                  90                  95

Gly Thr Ser Gln Asn Thr Leu Tyr Phe Gly Ala Gly Thr Arg Leu Ser
            100                 105                 110

Val Leu

<210> SEQ ID NO 90
<211> LENGTH: 114
<212> TYPE: PRT
<213> ORGANISM: Artificial Sequence
<220> FEATURE:
<223> OTHER INFORMATION: Synthetic

<400> SEQUENCE: 90

Glu Ala Ala Val Thr Gln Ser Pro Arg Asn Lys Val Thr Val Thr Gly
1               5                   10                  15

Gly Asn Val Thr Leu Ser Cys Arg Gln Thr Asn Ser His Asn Tyr Met
            20                  25                  30

Tyr Trp Tyr Arg Gln Asp Thr Gly His Gly Leu Arg Leu Ile His Tyr
        35                  40                  45

Ser Tyr Gly Ala Gly Asn Leu Gln Ile Gly Asp Val Pro Asp Gly Tyr
    50                  55                  60

Lys Ala Thr Arg Thr Thr Gln Glu Asp Phe Phe Leu Leu Leu Glu Leu
65                  70                  75                  80

Ala Ser Pro Ser Gln Thr Ser Leu Tyr Phe Cys Ala Ser Ser Asp Ala
                85                  90                  95

Gly Val Ser Gln Asn Thr Leu Tyr Phe Gly Ala Gly Thr Arg Leu Ser
            100                 105                 110

Val Leu

<210> SEQ ID NO 91
<211> LENGTH: 114
<212> TYPE: PRT
<213> ORGANISM: Artificial Sequence
<220> FEATURE:
<223> OTHER INFORMATION: Synthetic

<400> SEQUENCE: 91

Glu Ala Ala Val Thr Gln Ser Pro Arg Asn Lys Val Thr Val Thr Gly
1               5                   10                  15

Gly Asn Val Thr Leu Ser Cys Arg Gln Thr Asn Ser His Asn Tyr Met
            20                  25                  30

Tyr Trp Tyr Arg Gln Asp Thr Gly His Gly Leu Arg Leu Ile His Tyr
        35                  40                  45

Ser Tyr Gly Ala Gly Asn Leu Gln Ile Gly Asp Val Pro Asp Gly Tyr
    50                  55                  60
```

```
Lys Ala Thr Arg Thr Thr Gln Glu Asp Phe Phe Leu Leu Leu Glu Leu
 65                  70                  75                  80

Ala Ser Pro Ser Gln Thr Ser Leu Tyr Phe Cys Ala Ser Ser Asp Ala
                 85                  90                  95

Gly Thr Ala Gln Asn Thr Leu Tyr Phe Gly Ala Gly Thr Arg Leu Ser
            100                 105                 110

Val Leu

<210> SEQ ID NO 92
<211> LENGTH: 114
<212> TYPE: PRT
<213> ORGANISM: Artificial Sequence
<220> FEATURE:
<223> OTHER INFORMATION: Synthetic

<400> SEQUENCE: 92

Glu Ala Ala Val Thr Gln Ser Pro Arg Asn Lys Val Thr Val Thr Gly
 1               5                  10                  15

Gly Asn Val Thr Leu Ser Cys Arg Gln Thr Asn Ser His Asn Tyr Met
                 20                  25                  30

Tyr Trp Tyr Arg Gln Asp Thr Gly His Gly Leu Arg Leu Ile His Tyr
             35                  40                  45

Ser Tyr Gly Ala Gly Asn Leu Gln Ile Gly Asp Val Pro Asp Gly Tyr
 50                  55                  60

Lys Ala Thr Arg Thr Thr Gln Glu Asp Phe Phe Leu Leu Leu Glu Leu
 65                  70                  75                  80

Ala Ser Pro Ser Gln Thr Ser Leu Tyr Phe Cys Ala Ser Ser Asp His
                 85                  90                  95

Gly Thr Gly Gln Asn Thr Leu Tyr Phe Gly Ala Gly Thr Arg Leu Ser
            100                 105                 110

Val Leu

<210> SEQ ID NO 93
<211> LENGTH: 40
<212> TYPE: PRT
<213> ORGANISM: Artificial Sequence
<220> FEATURE:
<223> OTHER INFORMATION: Synthetic

<400> SEQUENCE: 93

Pro Ser Asp Ser Ala Leu Tyr Leu Cys Ala Ala Ser Ile Thr Asn Ala
 1               5                  10                  15

Tyr Lys Val Ile Phe Gly Lys Gly Thr His Leu His Val Leu Pro Asn
                 20                  25                  30

Ile Gln Asn Pro Glu Pro Ala Val
             35                  40

<210> SEQ ID NO 94
<211> LENGTH: 40
<212> TYPE: PRT
<213> ORGANISM: Artificial Sequence
<220> FEATURE:
<223> OTHER INFORMATION: Synthetic

<400> SEQUENCE: 94

Pro Ser Asp Ser Ala Leu Tyr Leu Cys Ala Ala Ser Thr Val Asn Ala
 1               5                  10                  15

Tyr Lys Val Ile Phe Gly Lys Gly Thr His Leu His Val Leu Pro Asn
                 20                  25
```

Ile Gln Asn Pro Glu Pro Ala Val
        35                  40

<210> SEQ ID NO 95
<211> LENGTH: 40
<212> TYPE: PRT
<213> ORGANISM: Artificial Sequence
<220> FEATURE:
<223> OTHER INFORMATION: Synthetic

<400> SEQUENCE: 95

Pro Ser Asp Ser Ala Leu Tyr Leu Cys Ala Ala Ser Met Ile Asn Ala
1               5                   10                  15

Tyr Lys Val Ile Phe Gly Lys Gly Thr His Leu His Val Leu Pro Asn
            20                  25                  30

Ile Gln Asn Pro Glu Pro Ala Val
        35                  40

<210> SEQ ID NO 96
<211> LENGTH: 40
<212> TYPE: PRT
<213> ORGANISM: Artificial Sequence
<220> FEATURE:
<223> OTHER INFORMATION: Synthetic

<400> SEQUENCE: 96

Pro Ser Asp Ser Ala Leu Tyr Leu Cys Ala Ala Ser Met Ala Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 97
<211> LENGTH: 40
<212> TYPE: PRT
<213> ORGANISM: Artificial Sequence
<220> FEATURE:
<223> OTHER INFORMATION: Synthetic

<400> SEQUENCE: 97

Pro Ser Asp Ser Ala Leu Tyr Leu Cys Ala Ala Ser Ile Ser Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 98
<211> LENGTH: 40
<212> TYPE: PRT
<213> ORGANISM: Artificial Sequence
<220> FEATURE:
<223> OTHER INFORMATION: Synthetic

<400> SEQUENCE: 98

Pro Ser Asp Ser Ala Leu Tyr Leu Cys Ala Ala Ser Ile Val Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 99
<211> LENGTH: 40
<212> TYPE: PRT
<213> ORGANISM: Artificial Sequence
<220> FEATURE:
<223> OTHER INFORMATION: Synthetic

<400> SEQUENCE: 99

Pro Ser Asp Ser Ala Leu Tyr Leu Cys Ala Ala Ser Lys Thr Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 100
<211> LENGTH: 40
<212> TYPE: PRT
<213> ORGANISM: Artificial Sequence
<220> FEATURE:
<223> OTHER INFORMATION: Synthetic

<400> SEQUENCE: 100

Pro Ser Asp Ser Ala Leu Tyr Leu Cys Ala Ala Ser Met Thr Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 101
<211> LENGTH: 40
<212> TYPE: PRT
<213> ORGANISM: Artificial Sequence
<220> FEATURE:
<223> OTHER INFORMATION: Synthetic

<400> SEQUENCE: 101

Pro Ser Asp Ser Ala Leu Tyr Leu Cys Ala Ala Thr Leu Thr Gly Gly
1               5                   10                  15

Tyr Lys Val Val Phe Gly Ser Gly Thr Arg Leu Leu Val Ser Pro Asp
            20                  25                  30

Ile Gln Asn Pro Glu Pro Ala Val
        35                  40

<210> SEQ ID NO 102
<211> LENGTH: 40
<212> TYPE: PRT
<213> ORGANISM: Artificial Sequence
<220> FEATURE:
<223> OTHER INFORMATION: Synthetic

<400> SEQUENCE: 102

Ser Gln Thr Ser Leu Tyr Phe Cys Ala Ser Ser Asp Ala Gly Thr Ser
1               5                   10                  15

Gln Asn Thr Leu Tyr Phe Gly Ala Gly Thr Arg Leu Ser Val Leu Glu
            20                  25                  30

Asp Leu Arg Asn Val Thr Pro Pro
        35                  40

<210> SEQ ID NO 103

```
<211> LENGTH: 40
<212> TYPE: PRT
<213> ORGANISM: Artificial Sequence
<220> FEATURE:
<223> OTHER INFORMATION: Synthetic

<400> SEQUENCE: 103

Ser Gln Thr Ser Leu Tyr Phe Cys Ala Ser Ser Asp Ala Gly Val Ser
1               5                   10                  15

Gln Asn Thr Leu Tyr Phe Gly Ala Gly Thr Arg Leu Ser Val Leu Glu
            20                  25                  30

Asp Leu Arg Asn Val Thr Pro Pro
        35                  40

<210> SEQ ID NO 104
<211> LENGTH: 40
<212> TYPE: PRT
<213> ORGANISM: Artificial Sequence
<220> FEATURE:
<223> OTHER INFORMATION: Synthetic

<400> SEQUENCE: 104

Ser Gln Thr Ser Leu Tyr Phe Cys Ala Ser Ser Asp Ala Gly Thr Ala
1               5                   10                  15

Gln Asn Thr Leu Tyr Phe Gly Ala Gly Thr Arg Leu Ser Val Leu Glu
            20                  25                  30

Asp Leu Arg Asn Val Thr Pro Pro
        35                  40

<210> SEQ ID NO 105
<211> LENGTH: 40
<212> TYPE: PRT
<213> ORGANISM: Artificial Sequence
<220> FEATURE:
<223> OTHER INFORMATION: Synthetic

<400> SEQUENCE: 105

Ser Gln Thr Ser Leu Tyr Phe Cys Ala Ser Ser Asp His Gly Thr Gly
1               5                   10                  15

Gln Asn Thr Leu Tyr Phe Gly Ala Gly Thr Arg Leu Ser Val Leu Glu
            20                  25                  30

Asp Leu Arg Asn Val Thr Pro Pro
        35                  40
```